US008868317B2

(12) United States Patent
Aoki

(10) Patent No.: US 8,868,317 B2
(45) Date of Patent: Oct. 21, 2014

(54) FUEL INJECTION AMOUNT CONTROL APPARATUS FOR AN INTERNAL COMBUSTION ENGINE

(75) Inventor: Keiichiro Aoki, Sunto-gun (JP)

(73) Assignee: Toyota Jidosha Kabushiki Kaisha, Aichi (JP)

(*) Notice: Subject to any disclaimer, the term of this patent is extended or adjusted under 35 U.S.C. 154(b) by 6 days.

(21) Appl. No.: 13/816,412

(22) PCT Filed: Aug. 12, 2010

(86) PCT No.: PCT/JP2010/063727
§ 371 (c)(1),
(2), (4) Date: Feb. 11, 2013

(87) PCT Pub. No.: WO2012/020500
PCT Pub. Date: Feb. 16, 2012

(65) Prior Publication Data
US 2013/0138329 A1 May 30, 2013

(51) Int. Cl.
B60T 7/12 (2006.01)
F02D 41/00 (2006.01)
F02D 41/30 (2006.01)
F02D 41/14 (2006.01)
G01N 27/407 (2006.01)

(52) U.S. Cl.
CPC .... *F02D 41/3005* (2013.01); *F02D 2200/0611* (2013.01); *F02D 41/0025* (2013.01); *F02D 41/1441* (2013.01); *G01N 27/4072* (2013.01); *F02D 41/1448* (2013.01); *F02D 41/1454* (2013.01); *F02D 41/0085* (2013.01); *G01N 27/4075* (2013.01)
USPC ........................... 701/103; 123/1 A; 123/494

(58) Field of Classification Search
CPC ..... F02B 1/04; F02D 41/182; F02D 41/0002; F02D 2041/30; F02D 41/30

USPC .......... 701/103–105, 114, 115; 123/1 A, 494, 123/434, 436, 673, 674, 679, 690
See application file for complete search history.

(56) References Cited

U.S. PATENT DOCUMENTS 5,249,453 A   10/1993   Usami et al.
5,289,717 A   3/1994    Ishida
(Continued)

FOREIGN PATENT DOCUMENTS

JP   04-060134 A   2/1992
JP   04-080653 A   3/1992
(Continued)

OTHER PUBLICATIONS

International Search Report of PCT/JP2010/063727 dated Sep. 14, 2010.

*Primary Examiner* — John Kwon
(74) *Attorney, Agent, or Firm* — Sughrue Mion, PLLC

(57) ABSTRACT

A fuel injection amount control apparatus of an embodiment according to the present invention comprises an air-fuel ratio sensor 56 which is disposed between an exhaust gas aggregated portion HK and a three-way catalyst 43, and which outputs an output value corresponding to an amount of oxygen and an amount of unburnt substances contained in an exhaust gas that has reached an exhaust-gas-side electrode layer via a porous layer (diffusion resistance layer). This control apparatus obtains an actual detected air-fuel ratio by correcting the output value of the air-fuel ratio sensor 56 based on an alcohol concentration of a fuel detected by the alcohol concentration sensor 59 and an air-fuel ratio imbalance indicating value representing a degree of a non-uniformity among cylinder-by-cylinder air-fuel ratios. The control apparatus feedback controls on a fuel amount in such a manner that the actual detected air-fuel ratio coincides with a target value.

15 Claims, 21 Drawing Sheets

(56) References Cited

U.S. PATENT DOCUMENTS

| | | |
|---|---|---|
| 8,370,043 B2 * | 2/2013 | Kidokoro et al. ............... 701/99 |
| 8,600,647 B2 * | 12/2013 | Demura ........................ 701/109 |
| 2009/0125214 A1 | 5/2009 | Yoshikawa |
| 2010/0168986 A1 | 7/2010 | Iwazaki et al. |
| 2010/0191444 A1 | 7/2010 | Aoki |
| 2011/0288739 A1 * | 11/2011 | Kidokoro et al. ............... 701/99 |
| 2012/0006307 A1 * | 1/2012 | Demura ........................ 123/674 |
| 2012/0173115 A1 | 7/2012 | Sawada et al. |

FOREIGN PATENT DOCUMENTS

| | | |
|---|---|---|
| JP | 04-204246 A | 7/1992 |
| JP | 2009-013967 A | 1/2009 |
| JP | 2009-030455 A | 2/2009 |
| JP | 2009-074388 A | 4/2009 |
| JP | 2009-115012 A | 5/2009 |
| JP | 2011-520727 A | 7/2011 |
| WO | 2011/001539 A1 | 1/2011 |

* cited by examiner

FUEL INJECTION AMOUNT CONTROL APPARATUS FOR AN INTERNAL COMBUSTION ENGINE

CROSS REFERENCE TO RELATED APPLICATIONS

This application is a National Stage of International Application No. PCT/JP2010/063727 filed Aug. 12, 2010, the contents of all of which are incorporated herein by reference in their entirety.

TECHNICAL FIELD

The present invention relates to a fuel injection amount control apparatus for a multi-cylinder internal combustion engine.

BACKGROUND ART

Conventionally, there has been widely known an air-fuel ratio control apparatus, which includes a three-way catalyst (43) disposed in an exhaust passage of an internal combustion engine, and an air-fuel ratio sensor (56) disposed upstream of the three-way catalyst (43), as shown in FIG. 1.

This air-fuel ratio control apparatus calculates an air-fuel ratio feedback amount (quantity) based on the output of the air-fuel ratio sensor (56) in such a manner that an air-fuel ratio (an air-fuel ratio of the engine, and thus, an air-fuel ratio of an exhaust gas) of an air-fuel mixture supplied to the engine coincides with a target air-fuel ratio, and feedback-controls the air-fuel ratio of the engine based on the air-fuel ratio feedback amount. The air-fuel ratio feedback amount used in such an air-fuel ratio control apparatus is a control amount commonly used for all of the cylinders. The target air-fuel ratio is set at a base (reference) air-fuel ratio which is within a window of the three way catalyst (43). The base air-fuel ratio is typically equal to a stoichiometric air-fuel ratio. The base air-fuel ratio may be changed to an air-fuel ratio in the vicinity of the stoichiometric air-fuel ratio base on an intake air amount of the engine, a deterioration degree of the three way catalyst (43), and so on.

Incidentally, in general, such an air-fuel ratio control apparatus is applied to an internal combustion engine using an electronic-control-fuel-injection apparatus. The internal combustion engine has at least one fuel injection valve (33) at each of cylinders or at each of intake ports communicating with the respective cylinders. Accordingly, when the characteristic/property of the fuel injection valve of a certain (specific) cylinder changes so as to inject fuel in an amount excessively larger than an injection amount to be injected according to an instruction (instructed fuel injection amount), only an air-fuel ratio of an air-fuel mixture supplied to that certain cylinder (the air-fuel ratio of the certain cylinder) greatly changes toward the rich side. That is, the degree of air-fuel ratio non-uniformity among the cylinders (inter-cylinder air-fuel ratio variation; inter-cylinder air-fuel ratio imbalance) increases. In other words, there arises an imbalance among "cylinder-by-cylinder air-fuel ratios", each of which is the air-fuel ratio of the air-fuel mixture supplied to each of the cylinders.

It should be noted that, hereinafter, a cylinder corresponding to the fuel injection valve having the characteristic to inject the fuel in an amount excessively larger or excessively smaller than the instructed fuel injection amount is also referred to as an imbalanced cylinder, and each of the remaining cylinders (a cylinder corresponding to the fuel injection valve having the characteristic to inject the fuel in an amount equal to the instructed fuel injection amount) is also referred to as an un-imbalanced cylinder (or a normal cylinder).

When the characteristic/property of the fuel injection valve of the certain (specific) cylinder changes so as to inject fuel in the amount excessively larger than the instruction injection amount, an average of the air-fuel ratio of the air-fuel mixture supplied to the entire engine becomes richer than the target air-fuel ratio which is set at the base air-fuel ratio. Accordingly, by means of the air-fuel ratio feedback amount commonly used for all of the cylinders, the air-fuel ratio of the above-mentioned certain cylinder is changed toward the lean side so as to come closer to the base air-fuel ratio, and, at the same time, the air-fuel ratios of the remaining cylinders are changed toward the lean side so as to deviate more greatly from the base air-fuel ratio. As a result, the average (air-fuel ratio of the exhaust gas) of the air-fuel ratio of the air-fuel mixture supplied to the entire engine becomes equal to an air-fuel ratio in the vicinity of the base air-fuel ratio.

However, the air-fuel ratio of the certain cylinder is still in the rich side in relation to the base air-fuel ratio, and the air-fuel ratios of the remaining cylinders are in the lean side in relation to the base air-fuel ratio. Consequently, an amount of emissions (an amount of unburned combustibles(substances) and/or an amount of nitrogen oxides) discharged from each of the cylinders increase, as compared to the case in which each of the air-fuel ratios of the cylinders is equal to the base air-fuel ratio.

Therefore, even when the average of the air-fuel ratio of the mixture supplied to the engine is equal to the base air-fuel ratio, the increased emissions cannot be removed by the three-way catalyst. Consequently, the amount of emissions may increase.

Accordingly, in order to prevent the emissions from increasing, it is important to detect a state in which the degree of the non-uniformity among the cylinder-by-cylinder air-fuel ratios becomes excessively large (i.e., the non-uniformity of the air-fuel ratio among the cylinders becomes excessively large, that is, generation of an inter-cylinder air-fuel ratio imbalance state), and to take some measures against the imbalance state. It should be noted that, the inter-cylinder air-fuel ratio imbalance also occurs, for example, in a case where the characteristic of the fuel injection valve of a certain cylinder changes to inject fuel in an amount excessively smaller than the instructed fuel injection amount.

One of conventional fuel injection amount control apparatuses obtains a trace/trajectory length of the output value (output signal) of the upstream air-fuel ratio sensor (56). Further, the control apparatus compares the trace length with a "reference value which changes in accordance with an engine rotational speed", and determines whether or not the inter-cylinder air-fuel ratio imbalance state has occurred based on the result of the comparison (see, for example, patent literature No. 1).

Meanwhile, when the non-uniformity among the cylinder-by-cylinder air-fuel ratios occurs, there may be a case in which a true average of the air-fuel ratio of the engine is controlled so as to become an air-fuel ratio larger than the base air-fuel ratio (leaner than the base air-fuel ratio) by means of the feedback control (main feedback control) to have an air-fuel ratio represented by the output value of the air-fuel ratio sensor (56) coincide with the "target air-fuel ratio which is set at the base air-fuel ratio such as the stoichiometric air-fuel ratio." The reason for this will next be described.

The fuel supplied to the engine is a chemical compound of carbon and hydrogen. Accordingly, the unburnt substances such as "carbon hydride HC, carbon monoxide CO, and hydrogen $H_2$" are generated as intermediate products, when the air-fuel ratio of the mixture to be combusted is richer than the stoichiometric air-fuel ratio. In this case, as the air-fuel ratio of the mixture for the combustion becomes richer in relation to the stoichiometric air-fuel ratio and deviates more greatly from the stoichiometric air-fuel ratio, a probability that the intermediate products meet and bind to the oxygen molecules during the combustion becomes drastically smaller. Consequently, as shown in FIG. 2, an amount of the unburnt substances (HC, CO, and $H_2$) drastically (e.g., in a quadratic function fashion) increases, as the air-fuel ratio of the mixture supplied to the cylinder becomes richer.

It is now assumed that a non-uniformity among the cylinder-by-cylinder air-fuel ratios occurs where only the air-fuel ratio of a certain cylinder greatly deviates toward the rich side. Under this assumption, the air-fuel ratio (air-fuel ratio of the certain cylinder) of the air-fuel mixture supplied to that certain cylinder changes to a much richer (smaller) air-fuel ratio, compared to the air-fuel ratios (air-fuel ratios of the remaining cylinders) of the air-fuel mixtures supplied to the remaining cylinders. At this time, a great amount of unburnt substances (HC, CO, and $H_2$) are discharged from that certain cylinder. Accordingly, even when the average of the air-fuel ratio of the mixtures supplied to the engine coincides with a "certain (specific) air-fuel ratio", a total amount of hydrogen discharged from the engine when the degree of the non-uniformity among the cylinder-by-cylinder air-fuel ratios becomes large is significantly larger than a total amount of hydrogen discharged from the engine when the non-uniformity among the cylinder-by-cylinder air-fuel ratios is not occurring.

In the mean time, the air-fuel ratio sensor (56) comprises a porous layer (e.g., a diffusion resistance layer, or a protective layer) that makes a "gas (gas after oxygen equilibrium) which is in a state where the unburnt substances and oxygen have chemically achieved equilibrium" reach the air-fuel ratio detection element. The air-fuel ratio sensor (56) outputs a value corresponding to "an amount of oxygen (oxygen partial pressure, oxygen concentration) or an amount of unburnt substance (unburnt substance partial pressure, unburnt substance concentration)" that has reached an exhaust-gas-side electrode layer (surface of the air-fuel ratio detection element) of the air-fuel ratio sensor (56) after passing through the diffusion resistance layer.

Meanwhile, hydrogen $H_2$ is a small molecule, compared with carbon hydride HC, carbon monoxide CO, and the like. Accordingly, hydrogen $H_2$ rapidly diffuses through the porous layer of the air-fuel ratio sensor (56), compared to the other unburnt substances (HC, CO). That is, a preferential diffusion of hydrogen $H_2$ occurs in the porous layer.

Due to the preferential diffusion of hydrogen when the non-uniformity among the cylinder-by-cylinder air-fuel ratios (air-fuel ratio imbalance among the cylinders) is occurring, the output value of the air-fuel ratio sensor (56) shifts to a value in a richer side. Thus, the air-fuel ratio represented by the output value of the air-fuel ratio sensor (56) becomes an "air-fuel ratio in the richer side" with respect to a true air-fuel ratio of the engine. Consequently, due to the main feedback control, the average of the air-fuel ratio of the engine is controlled so as to be the "air-fuel ratio larger than (leaner than) the base fuel air-fuel ratio."

In contrast, an exhaust gas which has passed through the three-way catalyst (43) arrives at an air-fuel ratio sensor (57) disposed at a position downstream of the three-way catalyst (43). The hydrogen is purified to some degree by the three-way catalyst (43). Accordingly, the output value of the downstream air-fuel ratio sensor is in the vicinity of an output value corresponding to a true average of the air-fuel ratio of the engine, even when the degree of the non-uniformity among the cylinder-by-cylinder air-fuel ratios becomes large.

In view of the above, another conventional apparatus is configured so as to determines whether or not the degree of the non-uniformity among the cylinder-by-cylinder air-fuel ratios becomes large, based on a parameter indicative of a difference between the air-fuel ratio represented by the upstream air-fuel ratio sensor (56) and the air-fuel ratio represented by the downstream air-fuel ratio sensor (57) (see, for example, patent literature No. 2).

CITATION LIST

<Patent Literature No. 1> U.S. Pat. No. 7,152,594
<Patent Literature No. 2> Japanese Patent Application Laid-Open (kokai) No. 2009-30455

SUMMARY OF THE INVENTION

A "deviation/shift of the air-fuel ratio toward the lean side due to the preferential diffusion of hydrogen and the main feedback control" is simply referred to as an "erroneous lean control." The "erroneous lean control" similarly occurs when the air-fuel ratio of the imbalanced cylinder becomes leaner than the air-fuel ratio of the un-imbalanced cylinder.

When the erroneous lean control occurs, there is a case in which the true average of the air-fuel ratio of the engine (and thus, a true average of the air-fuel ratio of the exhaust gas) becomes an air-fuel ratio leaner (larger) than the air-fuel ratio which is within the "window of the catalyst." Accordingly, there may be a case in which a purification efficiency of the NOx (nitrogen oxides) of the three-way catalyst (43) lowers, so that the discharge amount of NOx increases.

Meanwhile, a fuel (hereinafter, referred to as an "fuel containing alcohol") containing alcohol such ethanol, and the like has recently been used. When the fuel containing alcohol is burnt/combusted, a great amount of "hydrogen or carbonyl series compound" are produced, as compared to a case in which the fuel which does not contain alcohol is bunt/combusted. An amount of hydrogen generated by the combustion of the fuel containing alcohol becomes larger, as the concentration of the alcohol of the fuel becomes higher.

Accordingly, when the fuel containing alcohol is used, the output value of the air-fuel ratio sensor (56) shifts toward a value in the rich side due to the preferential diffusion of hydrogen, similarly to the case in which the degree of the non-uniformity among the cylinder-by-cylinder air-fuel ratios becomes large. That is, the air-fuel ratio represented by the air-fuel ratio sensor (56) becomes richer than the true air-fuel ratio of the engine. Consequently, due to the main feedback control based on the output value of the air-fuel ratio sensor (56), the true average of the air-fuel ratio of the engine is controlled to the air-fuel ratio leaner than the base air-fuel ratio such as the stoichiometric air-fuel ratio. That is, even when the non-uniformity among cylinder-by-cylinder air-fuel ratios is not occurring, the usage of the fuel containing alcohol causes the erroneous lean control. As a result, there may be a case in which the purification efficiency of NOx of the three-way catalyst (43) lowers, so that the discharge amount of NOx increases.

As understood from the above, the output value of the air-fuel ratio sensor (56) varies depending on not only the degree of the non-uniformity among the cylinder-by-cylinder air-fuel ratios but also the concentration of the alcohol of the fuel. Accordingly, one of the objects of the present invention is to provide a fuel injection amount control apparatus for an internal combustion engine (hereinafter, simply referred to as a "present invention apparatus") which enables the true average of the air-fuel ratio of the engine to come close to the base air-fuel ratio as much as possible by the main feedback control, taking consideration of the concentration of the alcohol of the fuel and the degree of the non-uniformity among the cylinder-by-cylinder air-fuel ratios.

The present invention apparatus is the fuel injection amount control apparatus for a multi-cylinder internal combustion engine, which comprises a three way catalyst, an air-fuel ratio sensor, a plurality of fuel injection valves, an alcohol concentration obtaining section, an air-fuel ratio imbalance indicating value obtaining section, a first air-fuel ratio correlated parameter obtaining section, an instructed fuel injection amount determining section, and an injection instruction signal supplying section.

The three way catalyst is disposed in an exhaust passage of the engine and at a position downstream of an "exhaust gas aggregated portion of the exhaust passage" into which exhaust gases discharged from a plurality of the cylinders which the multi cylinder internal combustion engine comprises merge.

The air-fuel ratio sensor is disposed in the exhaust passage and at a "position between the exhaust gas aggregated portion and the three way catalyst." The air-fuel ratio sensor includes an air-fuel ratio detection element; an exhaust-gas-side electrode layer and a reference-gas-side electrode layer, that are formed so as to face to each other across the air-fuel ratio detection element; and a porous layer which covers the exhaust-gas-side electrode layer. The air-fuel ratio sensor outputs an output value corresponding to "an amount of oxygen (oxygen partial pressure, oxygen concentration) and an amount of unburnt substance (unburnt substance partial pressure, unburnt substance concentration)" contained in an "exhaust gas that has reached the exhaust-gas-side electrode layer via the porous layer" (included) in (or among) an "exhaust gas passing through the position at which the air-fuel ratio sensor is disposed."

Each of the fuel injection valves is configured so as to inject a fuel to be contained in a mixture supplied to each of combustion chambers of a plurality of the cylinders. That is, one or more of the fuel injectors is/are provided for each one of the cylinders.

The alcohol concentration obtaining section obtains an alcohol concentration of the fuel.

The air-fuel ratio imbalance indicating value obtaining section obtains an air-fuel ratio imbalance indicating value. The air-fuel ratio imbalance indicating value is a value which becomes larger as the degree of the non-uniformity of an "air-fuel ratio (that is, cylinder-by-cylinder air-fuel ratio) of a mixture supplied to each of the combustion chambers of a plurality of the cylinders" among a plurality of the cylinders becomes larger. As described later, the air-fuel ratio imbalance indicating value can be calculated based on various parameters (predetermined specific parameters). That is, for example, the air-fuel ratio imbalance indicating value may be calculated based on the output value of the air-fuel ratio sensor, a tentative detected air-fuel ratio (second air-fuel ratio correlated parameter), an engine rotational speed, a parameter represented by the output value of the air-fuel ratio sensor and an output value of a downstream air-fuel ratio sensor disposed at a position downstream of the three way catalyst (i.e., sub feedback amount correlated value, refer to Japanese Patent Application Laid-Open (kokai) Nos. 2009-30455), and the like.

The first air-fuel ratio correlated parameter obtaining section converts the output value of the air-fuel ratio sensor into an actual first air-fuel ratio correlated parameter. The first air-fuel ratio correlated parameter is a value correlated to a true air-fuel ratio of the exhaust gas, and may be the true air-fuel ratio of the exhaust gas, the output value of the air-fuel ratio sensor corresponding to the true air-fuel ratio of the exhaust gas, and the like. That is, the first air-fuel ratio correlated parameter is a parameter correlated to a value obtained by eliminating an effect on the output value of the air-fuel ratio sensor which the alcohol concentration and the air-fuel ratio imbalance indicating value (degree of the non-uniformity among the cylinder-by-cylinder air-fuel ratios) have.

More specifically, the first air-fuel ratio correlated parameter obtaining section converts the actual output value of the air-fuel ratio sensor into the actual first air-fuel ratio correlated parameter based on the obtained actual alcohol concentration and the obtained actual air-fuel ratio imbalance indicating value, using a "predetermined first relationship among the output value of the air-fuel ratio sensor, the alcohol concentration, the air-fuel ratio imbalance indicating value, and the first air-fuel ratio correlated parameter correlated to the true air-fuel ratio of the exhaust gas." As described later, the first relationship may be represented by a single "look-up table or function", or by a combination of a plurality of "look-up tables or functions."

The instructed fuel injection amount determining section determines an instructed fuel injection amount which is an instruction value of an amount of a fuel to be injected from each of a plurality of the fuel injection valves, by performing a feedback correction on the amount of the fuel to be injected from each of the fuel injection valves in such a manner that the obtained actual first air-fuel ratio correlated parameter coincides with a predetermined target value. That is, the instructed fuel injection amount determining section performs the main feedback control based on the obtained actual first air-fuel ratio correlated parameter.

The injection instruction signal supplying section sends (supplies) the injection instruction signal to a plurality of the fuel injection valves in such a manner that the fuel of an amount corresponding to the instructed fuel injection amount is injected from each of a plurality of the fuel injection valves.

As described before, the output value of the air-fuel ratio sensor varies depending on not only the degree of the non-uniformity among the cylinder-by-cylinder air-fuel ratios (i.e., magnitude of the air-fuel ratio imbalance indicating value) but also the alcohol concentration, even when the true air-fuel ratio of the exhaust gas remains the same. In view of the above, an aspect of the present invention apparatus obtains the first relationship among the output value of the air-fuel ratio sensor, the alcohol concentration, the air-fuel ratio imbalance indicating value, and the first air-fuel ratio correlated parameter correlated to the true air-fuel ratio of the exhaust gas" in advance according to experiments or the like, and stores the first relationship in a storage memory or the like.

Further, the aspect of the present invention apparatus converts the actual output value of the air-fuel ratio sensor into the first air-fuel ratio correlated parameter based on the actual alcohol concentration, the actual air-fuel ratio imbalance indicating value, and the first relationship. Accordingly the first air-fuel ratio correlated parameter becomes/is a value corresponding to the true air-fuel ratio of the exhaust gas. Therefore, by the main feedback control to have the first air-fuel ratio correlated parameter coincide with the target value, the true air-fuel ratio of the exhaust gas can be adjusted to coincide with an air-fuel ratio corresponding to the target value. Consequently, the increase of the discharge amount of NOx and the like can be avoided, regardless of the degree of the non-uniformity among the cylinder-by-cylinder air-fuel ratios and the alcohol concentration.

Incidentally, when the degree of the non-uniformity among the cylinder-by-cylinder air-fuel ratios becomes large, the exhaust gases that are greatly different from each other are sequentially discharged. Therefore, a variation of the air-fuel ratio of the exhaust gas becomes larger as the degree of the non-uniformity among the cylinder-by-cylinder air-fuel ratios becomes larger. Accordingly, the air-fuel ratio imbalance indicating value can be obtained based on a value (e.g., a differential value of the first air-fuel ratio correlated parameter) indicative of a variation of the first air-fuel ratio correlated parameter (actual detected air-fuel ratio, or the like). However, when the degree of the non-uniformity among the cylinder-by-cylinder air-fuel ratios has changed from a first value to a second value, the value of the air-fuel ratio imbalance indicating value changes, and thus, the first air-fuel ratio correlated parameter varying depending on the alcohol concentration and the air-fuel ratio imbalance indicating value also changes. As a result, the air-fuel ratio imbalance indicating value again changes. Furthermore, this causes the actual detected air-fuel ratio to change again.

As described above, if the air-fuel ratio imbalance indicating value is obtained based on the first air-fuel ratio correlated parameter, a plurality of the air-fuel ratio imbalance indicating values may be obtained even when the degree of the non-uniformity among the cylinder-by-cylinder air-fuel ratios remains unchanged (in the above example, remains the second value). In other words, the air-fuel ratio imbalance indicating value obtained based on the first air-fuel ratio correlated parameter can not be a value which indicates the degree of the non-uniformity among the cylinder-by-cylinder air-fuel ratios with high accuracy. Meanwhile, the output value of the air-fuel ratio sensor varies depending on the alcohol concentration. Here, the air-fuel ratio imbalance indicating value should remain unchanged as long as the degree of the non-uniformity among the cylinder-by-cylinder air-fuel ratios remains unchanged, even when the alcohol concentration changes.

In view of the above, in the aspect of the present invention apparatus, the air-fuel ratio imbalance indicating value obtaining section is configured so as to:

convert the actual output value of the air-fuel ratio sensor into an actual second air-fuel ratio correlated parameter based on the obtained actual alcohol concentration, using a "predetermined second relationship among the output value of the air-fuel ratio sensor, the alcohol concentration, and the second air-fuel ratio correlated parameter correlated to the true air-fuel ratio of the exhaust gas" in a case in which the non-uniformity of the cylinder-by-cylinder air-fuel ratio among a plurality of the cylinders does not occur;

adopt, as the specific parameter (parameter for obtaining the air-fuel ratio imbalance indicating value), the actual second air-fuel ratio correlated parameter; and obtain, as the air-fuel ratio imbalance indicating value, a value which becomes larger as a variation of the second air-fuel ratio correlated parameter becomes larger.

The second air-fuel ratio correlated parameter is a parameter correlated to a value, which is obtained by eliminating the effect on the output value of the air-fuel ratio sensor which the alcohol concentration has, and which does not vary depending on the air-fuel ratio imbalance indicating value. Consequently, it is possible to obtain the air-fuel ratio imbalance indicating value which represents the degree of the non-uniformity among the cylinder-by-cylinder air-fuel ratios with high accuracy. Further, the first air-fuel ratio correlated parameter obtained based on the air-fuel ratio imbalance indicating value becomes a value which represent the true air-fuel ratio of the exhaust gas with high accuracy, and therefore, the true air-fuel ratio of the exhaust gas can be controlled with high accuracy so as to be an air-fuel ratio corresponding to the target value.

The air-fuel ratio sensor may be a "limiting-current-type air-fuel ratio sensor" or an "electro-motive-force-type (concentration-cell-type) oxygen concentration sensor." However, the output value of the limiting-current-type air-fuel ratio sensor varies depending on a pressure of the gas to be detected (in the present case, a pressure of the exhaust gas reaching the air-fuel ratio sensor).

In view of the above, the aspect of the present invention apparatus obtains the first air-fuel ratio correlated parameter and the second air-fuel ratio correlated parameter, while eliminating the effect on the output value of the air-fuel ratio sensor which the pressure of the exhaust gas has.

More specifically, the aspect of the present invention apparatus comprises an exhaust gas pressure obtaining section which obtains an actual pressure of the exhaust gas reaching the air-fuel ratio sensor.

Further, in this aspect, the first relationship is a "relationship among the output value of the air-fuel ratio sensor, the alcohol concentration, the air-fuel ratio imbalance indicating value, the pressure of the exhaust gas reaching the air-fuel ratio sensor, and the first air-fuel ratio correlated parameter", and the first air-fuel ratio correlated parameter obtaining section converts the actual output value of the air-fuel ratio sensor into the actual first air-fuel ratio correlated parameter based on not only the obtained actual alcohol concentration and the obtained actual air-fuel ratio imbalance indicating value but also the obtained actual pressure (and by using the first relationship).

According to the configuration described above, it is possible to obtain the first air-fuel ratio correlated parameter which represents the true air-fuel ratio of the exhaust gas with high accuracy, even when the pressure of the exhaust gas changes.

In addition, in the aspect of the present invention apparatus, the second relationship is a relationship among the output value of the air-fuel ratio sensor, the alcohol concentration, the pressure of the exhaust gas reaching the air-fuel ratio sensor, and the second air-fuel ratio correlated parameter", and the air-fuel ratio imbalance indicating value obtaining section is configured so as to convert the actual output value of the air-fuel ratio sensor into the actual second air-fuel ratio correlated parameter based on not only the obtained actual alcohol concentration but also the obtained actual pressure.

According to the configuration described above, it is possible to obtain the second air-fuel ratio correlated parameter which remains unchanged as long as the degree of the non-uniformity among the cylinder-by-cylinder air-fuel ratios remains unchanged, even when the pressure of the exhaust gas changes.

In the aspect of the present invention apparatus:

the first air-fuel ratio correlated parameter obtaining section may be configured so as to obtain, as the first air-fuel ratio correlated parameter, a value which is an air-fuel ratio into which the actual output value of the air-fuel ratio sensor is converted using the first relationship, the converted air-fuel ratio being an air-fuel ratio which becomes larger as the actual alcohol concentration becomes higher and as the actual air-fuel ratio imbalance indicating value becomes larger; and the instructed fuel injection amount determining section may be configured so as to use, as the target value, a target air-fuel ratio which is set at a predetermined air-fuel ratio which is within the window of the three way catalyst.

In this case, the first air-fuel ratio correlated parameter obtaining section may be configured so as to:

store the first relationship in a form of a look-up table or a function, which inputs the output value of the air-fuel ratio sensor, the alcohol concentration, and the air-fuel ratio imbalance indicating value, and outputs the first air-fuel ratio correlated parameter; and obtain the actual first air-fuel ratio correlated parameter by inputting the actual output value of the air-fuel ratio sensor, the actual alcohol concentration, and the actual air-fuel ratio imbalance indicating value to the look-up table or the function.

Alternatively, the first air-fuel ratio correlated parameter obtaining section may be configured so as to store the first relationship as, a first look-up table or a first function for converting, based on the alcohol concentration, the output value of the air-fuel ratio sensor into an "output value of the air-fuel ratio sensor in a case in which the alcohol concentration is equal to a predetermined base (reference) alcohol concentration";

a second look-up table or a second function for converting, based on the air-fuel ratio imbalance indicating value, the output value of the air-fuel ratio sensor into an "output value of the air-fuel ratio sensor in a case in which the air-fuel ratio imbalance indicating value is equal to a predetermined base (reference) air-fuel ratio imbalance indicating value"; and a third look-up table or a third function for converting the "output value of the air-fuel ratio sensor when the alcohol concentration is equal to the base alcohol concentration and the air-fuel ratio imbalance indicating value is equal to the base air-fuel ratio imbalance indicating value" into an air-fuel ratio.

In this case, the first air-fuel ratio correlated parameter obtaining section may be configured so as to:

obtain, as an alcohol concentration corrected output value, an output value of the air-fuel ratio sensor which is obtained by inputting the actual output value of the air-fuel ratio sensor and the actual alcohol concentration to the first look-up table or the first function;

obtain, as an alcohol concentration•air-fuel ratio imbalance indicating value corrected output value, an output value of the air-fuel ratio sensor which is obtained by inputting the alcohol concentration corrected output value and the actual air-fuel ratio imbalance indicating value to the second look-up table or the second function; and obtain, as the actual first air-fuel ratio correlated parameter, an air-fuel ratio which is obtained by inputting the alcohol concentration•air-fuel ratio imbalance indicating value corrected output value to the third look-up table or the third function.

That is, the first air-fuel ratio correlated parameter obtaining section may obtain the actual first air-fuel ratio correlated parameter by:

obtaining the alcohol concentration corrected output value by correcting the actual output value of the air-fuel ratio sensor based on the actual alcohol concentration;

obtain the alcohol concentration•air-fuel ratio imbalance indicating value corrected output value by correcting the alcohol concentration corrected output value based on the actual air-fuel ratio imbalance indicating value; and converting the alcohol concentration•air-fuel ratio imbalance indicating value corrected output value into to an air-fuel ratio.

Incidentally, the feedback correction described above is a feedback control to have the first air-fuel ratio correlated parameter coincide with the target value. In this case, the first air-fuel ratio correlated parameter and the target value are values having an "air-fuel ratio" as a unit, or values having an "output value of the air-fuel ratio sensor" as a unit.

In a case in which the units of the first air-fuel ratio correlated parameter and the target value are the "output values of the air-fuel ratio sensor":

the first air-fuel ratio correlated parameter obtaining section may be configured so as to obtain, as the first air-fuel ratio correlated parameter, a value into which the actual output value of the air-fuel ratio sensor is converted based on the actual alcohol concentration and the actual air-fuel ratio imbalance indicating value using the first relationship, so that the actual output value of the air-fuel ratio sensor becomes an "output value when the alcohol concentration is equal to the predetermined base alcohol concentration and the actual air-fuel ratio imbalance indicating value is equal to the predetermined base air-fuel ratio imbalance indicating value"; and the instructed fuel injection amount determining section may be configured so as to use, as the target value, a "value which is equal to the output value of the air-fuel ratio sensor for a predetermined air-fuel ratio which is within the window of the three way catalyst" when the alcohol concentration is equal to the predetermined base alcohol concentration and the actual air-fuel ratio imbalance indicating value is equal to the predetermined base air-fuel ratio imbalance indicating value.

In this case, the first air-fuel ratio correlated parameter obtaining section may be configured so as to:

store the first relationship as, a first look-up table or a first function for converting, based on the alcohol concentration, the output value of the air-fuel ratio sensor into an output value of the air-fuel ratio sensor in a case in which the alcohol concentration is equal to the predetermined base (reference) alcohol concentration; and a second look-up table or a second function for converting, based on the air-fuel ratio imbalance indicating value, the output value of the air-fuel ratio sensor into an output value of the air-fuel ratio sensor in a case in which the air-fuel ratio imbalance indicating value is equal to the predetermined base (reference) air-fuel ratio imbalance indicating value;

obtain, as an alcohol concentration corrected output value, an output value of the air-fuel ratio sensor obtained by inputting the actual output value of the air-fuel ratio sensor and the actual alcohol concentration to the first look-up table or the first function; and obtain, as the first air-fuel ratio correlated parameter, an output value of the air-fuel ratio sensor obtained by inputting the obtained alcohol concentration corrected output value and the actual air-fuel ratio imbalance indicating value to the second look-up table or the second function.

The second air-fuel ratio correlated parameter can be obtained based on various ways, similarly to the first air-fuel ratio correlated parameter.

That is, the air-fuel ratio imbalance indicating value obtaining section may be configured so as to:

store the second relationship in a form of a look-up table or a function, which inputs the "output value of the air-fuel ratio sensor and the alcohol concentration" and outputs the "second air-fuel ratio correlated parameter"; and obtain the "actual second air-fuel ratio correlated parameter" by inputting "the actual output value of the air-fuel ratio sensor and the actual alcohol concentration" to the look-up table or the function.

Further, in a case in which the second air-fuel ratio correlated parameter is obtained in consideration of the pressure of the exhaust gas reaching the air-fuel ratio sensor, the air-fuel ratio imbalance indicating value obtaining section may be configured so as to:

store the second relationship in a form of a look-up table or a function, which inputs the "output value of the air-fuel ratio sensor, the alcohol concentration, and the pressure of the exhaust gas reaching the air-fuel ratio sensor" and outputs the "second air-fuel ratio correlated parameter"; and obtain the "actual second air-fuel ratio correlated parameter" by inputting "the actual output value of the air-fuel ratio sensor, the actual alcohol concentration, and the obtained actual pressure" to the look-up table or the function.

In this case, the air-fuel ratio imbalance indicating value obtaining section may be configured so as to obtain the air-fuel ratio imbalance indicating value based on one of:

a differential value of the second air-fuel ratio correlated parameter with respect to time;

a second order differential value of the second air-fuel ratio correlated parameter with respect to time; and a trace/trajectory length of the second air-fuel ratio correlated parameter in a predetermined period.

Incidentally, the first air-fuel ratio correlated parameter is calculated in such a manner that the first air-fuel ratio correlated parameter coincides with a value corresponding to the "true air-fuel ratio of the exhaust gas." However, when the non-uniformity among the cylinder-by-cylinder air-fuel ratios is occurring or the alcohol concentration is not equal to "0", a "change rate of the output value of the air-fuel ratio sensor (post rich-lean inversion responsivity)" when the true air-fuel ratio of the exhaust gas has changed from the "air-fuel ratio richer than the stoichiometric air-fuel ratio" to the "air-fuel ratio leaner than the stoichiometric air-fuel ratio" (i.e., at a rich-lean inversion time point) is smaller than a change rate of the output value of the air-fuel ratio sensor (post lean-rich inversion responsivity) when the true air-fuel ratio of the exhaust gas has changed from "air-fuel ratio leaner than the stoichiometric air-fuel ratio" to the "air-fuel ratio richer than the stoichiometric air-fuel ratio" (i.e., at a lean-rich inversion time point). This is because, the output value of the air-fuel ratio sensor is affected by hydrogen which is produced in a great amount" due to the occurrence of the non-uniformity among cylinder-by-cylinder air-fuel ratios or due to the inclusion of the alcohol in the fuel." Furthermore, the inversion responsivity of the output value of the air-fuel ratio sensor varies depending on the pressure of the exhaust gas reaching the air-fuel ratio sensor.

In view of the above, it is preferable that the instructed fuel injection amount determining section be configured so as to:

calculate a main feedback correction amount by multiplying a value correlated to a difference between the obtained actual first air-fuel ratio correlated parameter and the target value by a predetermined gain, and carry out the feedback correction using (based on) the main feedback correction amount; and set the gain to a larger value in a period after rich-lean inversion time point than one in a period after lean-rich inversion time point, the period after rich-lean inversion time point being a time period until a predetermined time elapses from a rich-lean inversion time point at which the actual output value of the air-fuel ratio sensor has changed from a value indicating an air-fuel ratio smaller than the stoichiometric air-fuel ratio to a value indicating an air-fuel ratio larger than the stoichiometric air-fuel ratio, and the period after lean-rich inversion time point being a time period until a predetermined time elapses from a lean-rich inversion time point at which the actual output value of the air-fuel ratio sensor has changed from a value indicating an air-fuel ratio larger than the stoichiometric air-fuel ratio to a value indicating an air-fuel ratio smaller than the stoichiometric air-fuel ratio.

In this case, it is preferable that the gain be set in such a manner that a difference between the gain set in the period after rich-lean inversion time point and the gain set in the period after lean-rich inversion time point becomes larger as at least one of the obtained actual alcohol concentration and the obtained actual air-fuel ratio imbalance indicating value becomes larger.

Other objects, features, and advantages of the present invention apparatus will be readily understood from the following description of each of embodiments of the present invention apparatus with reference to the accompanying drawings.

DESCRIPTION OF EMBODIMENTS

A fuel injection amount control apparatus (hereinafter, simply referred to as a "control apparatus") for an internal combustion engine according to each of embodiments of the present invention will be described with reference to the drawings. This control apparatus is a portion of an air-fuel ratio control apparatus for controlling an air-fuel ratio of a mixture supplied to the internal combustion engine (air-fuel ratio of the engine), and is also a portion of an inter-cylinder air-fuel ratio imbalance determining apparatus.

First Embodiment

Configuration

Figure 1:
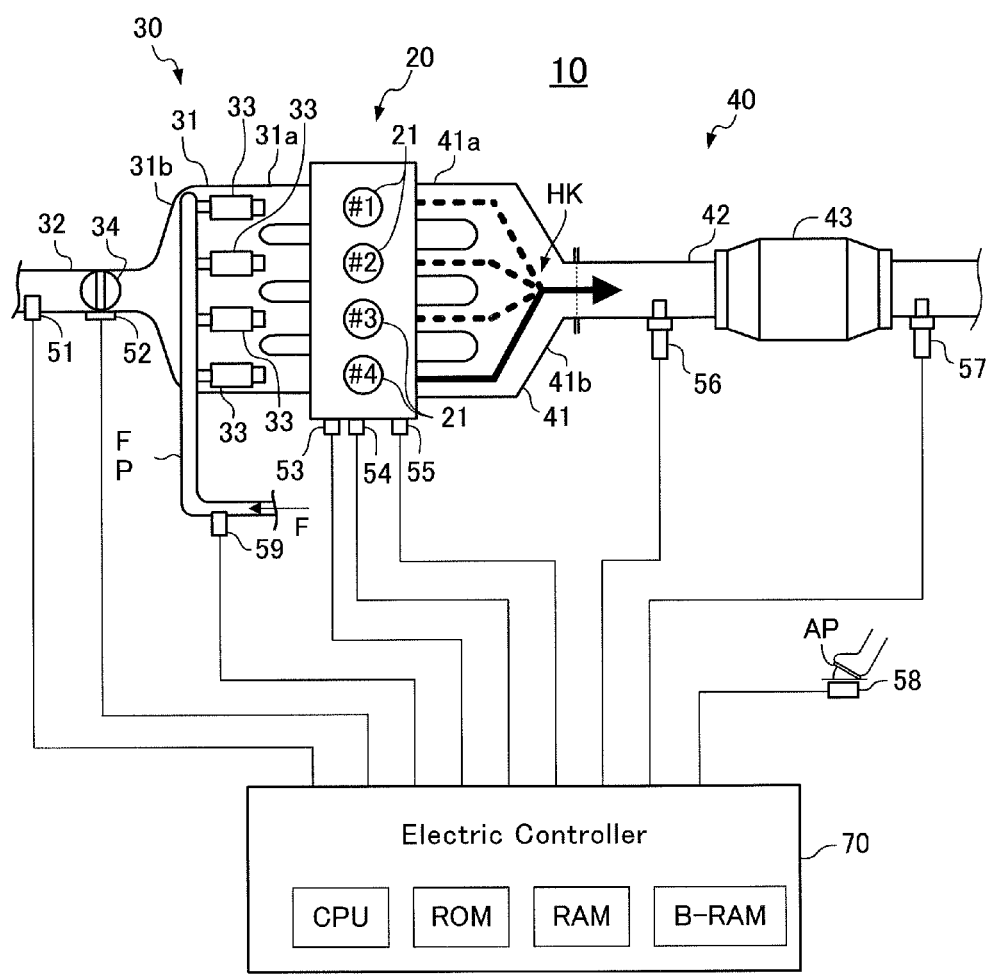
FIG. 1 is a schematic view of an internal combustion engine to which a fuel injection amount control apparatus according to each of embodiments of the present invention is applied.

FIG. 1 schematically shows a configuration of a system configured such that a control apparatus (hereinafter, referred to as a "first control apparatus") according to a first embodiment is applied to a spark-ignition multi-cylinder (straight 4-cylinder) four-cycle internal combustion engine 10.

The internal combustion engine 10 includes a main body section 20, an intake system 30, and an exhaust system 40.

The main body section 20 includes a cylinder block section and a cylinder head section. The main body section 20 has a plurality of cylinders (combustion chambers) 21. Each of the cylinders communicates with unillustrated "intake ports and exhaust ports." The communicating portions between the intake ports and the combustion chambers are opened and closed by unillustrated intake valves. The communicating portions between the exhaust ports and the combustion chambers are opened and closed by unillustrated exhaust valves. Each of the combustion chambers 21 is provided with an unillustrated spark plug.

The intake system 30 comprises an intake manifold 31, an intake pipe 32, a plurality of fuel injection valves 33, and a throttle valve 34.

The intake manifold 31 includes a plurality of branch portions 31a and a surge tank 31b. An end of each of a plurality of the branch portions 31a is connected to each of a plurality of the intake ports. The other end of each of a plurality of the branch portions 31a is connected to the surge tank 31b.

An end of the intake pipe 32 is connected to the surge tank 31b. An unillustrated air filter is provided at the other end of the intake pipe 32.

Each of the fuel injection valves 33 is provided for each of the cylinders (combustion chambers) 21. The fuel injection valve 33 is disposed in the intake port. That is, each of a plurality of the cylinders comprises the fuel injection valve 33 for supplying the fuel independently from the other cylinders. The fuel injection valve 33 is configured so as to inject, in response to an injection instruction signal, a "fuel of an instructed injection amount included in the injection instruction signal" into a corresponding intake port (and thus, to a cylinder corresponding to the fuel injection valve 33), when the fuel injection valve 33 is normal.

More specifically, the fuel injection valve 33 opens for a time period corresponding to the instructed fuel injection amount. A pressure of the fuel supplied to the fuel injection valve 33 is adjusted in such a manner that a difference between the pressure of the fuel and a pressure in the intake port is constant. Accordingly, when the fuel injection valve 33 is normal, the fuel injection valve 33 injects the fuel of the instructed fuel injection amount. However, when an abnormality occurs in the fuel injection valve 33, the fuel injection valve 33 injects the fuel of an amount different from the instructed fuel injection amount. This causes a non-uniformity of the cylinder-by-cylinder air-fuel ratio among the cylinders.

The throttle valve 34 is provided within the intake pipe 32. The throttle valve 34 is adapted to change the opening cross sectional area of the intake passage. The throttle valve 34 is rotated within the intake pipe 32 by an unillustrated throttle valve actuator.

The exhaust system 40 includes an exhaust manifold 41, an exhaust pipe 42, an upstream-side catalytic converter (catalyst) 43 disposed in the exhaust pipe 42, and an "unillustrated downstream-side catalytic converter (catalyst)" disposed in the exhaust pipe 42 at a position downstream of the upstream-side catalyst 43.

The exhaust manifold 41 comprises a plurality of branch portions 41a and an aggregated (merging) portion 41b. An end of each of a plurality of branch portions 41a is connected to each of a plurality of the exhaust ports. The other end of each of a plurality of branch portions 41a is connected to the aggregated portion 41b. This aggregated portion 41b is a portion into which the exhaust gases discharged from a plurality of (two or more of, and in the present example, four of) the cylinders aggregate (merge), and therefore, is referred to as an exhaust gas aggregated portion HK.

The exhaust pipe 42 is connected to the aggregated portion 41b. The exhaust ports, the exhaust manifold 41, and the exhaust pipe 42 constitute an exhaust passage.

Each of the upstream catalyst 43 and the downstream catalyst is a so-called three way catalyst unit (exhaust purifying catalyst) carrying an active component formed of a so-called noble metal (catalytic substance) such as platinum, rhodium, and palladium. Each of the catalysts has a function of oxidizing unburned combustibles (substances) such as HC, CO, and $H_2$ and reducing nitrogen oxides (NOx) when the air-fuel ratio of a gas flowing into each of the catalysts is an "air-fuel ratio within a window of the three-way catalyst (e.g., stoichiometric air-fuel ratio)." This function is also referred to as a catalytic function. Furthermore, each of the catalysts has an oxygen storage function of occluding (storing) oxygen. Each of the catalysts can purify the unburned combustibles and the nitrogen oxides even when the air-fuel ratio deviates from the stoichiometric air-fuel ratio, owing to the oxygen storage function. That is, the oxygen storage function expands the width of the window. The oxygen storage function is realized by an oxygen occluding (storing) substances such as ceria ($CeO_2$) carried by the catalyst.

This system includes a hot-wire air-flow meter 51, a throttle position sensor 52, a water temperature sensor 53, a crank position sensor 54, an intake-cam position sensor 55, an upstream air-fuel ratio sensor 56, a downstream air-fuel ratio sensor 57, an accelerator opening sensor 58, and an alcohol concentration sensor 59.

The air-flow meter 51 outputs a signal corresponding to a mass flow rate (intake air flow rate) Ga of an intake air flowing through the intake pipe 32. That is, the intake air flow rate Ga represents an intake air amount taken into the engine 10 per unit time.

The throttle position sensor 52 detects an opening of the throttle valve 34 (throttle valve opening), and outputs a signal representing the detected throttle valve opening TA.

The water temperature sensor 53 detects a temperature of a cooling water of the internal combustion engine 10, and outputs a signal representing the detected cooling water temperature THW. The cooling water temperature THW is a parameter representing a warming state of the engine 10 (temperature of the engine 10).

The crank position sensor 54 outputs a signal including a narrow pulse generated every time the crankshaft rotates 10° and a wide pulse generated every time the crankshaft rotates 360°. This signal is converted to an engine rotational speed NE by an electric controller 70, which will be described later.

The intake-cam position sensor 55 outputs a single pulse when the intake camshaft rotates 90 degrees from a predetermined angle, when the intake camshaft rotates 90 degrees after that, and when the intake camshaft further rotates 180 degrees after that. Based on the signals from the crank position sensor 54 and the intake-cam position sensor 55, the electric controller 70, which will be described later, obtains an absolute crank angle CA, while using, as a reference, a compression top dead center of a reference cylinder (e.g., the first cylinder). This absolute crank angle CA is set to "0° crank angle" at the compression top dead center of the reference cylinder, increases up to 720° crank angle in accordance with the rotational angle of the crank shaft, and is again set to 0° crank angle at that point in time.

The upstream air-fuel ratio sensor 56 is disposed in "either one of the exhaust manifold 41 and the exhaust pipe 42" and at a position between the aggregated portion 41b (exhaust gas merging/aggregated portion HK) of the exhaust manifold 41 and the upstream catalyst 43. The upstream air-fuel ratio sensor 56 corresponds to an air-fuel ratio sensor in the present invention.

The air-fuel ratio sensor 56 is a "limiting-current-type wide range air-fuel ratio sensor including a diffusion resistance layer" disclosed in, for example, Japanese Patent Application Laid-Open (kokai) Nos. H11-72473, 2000-65782, and 2004-69547.

Figure 3:
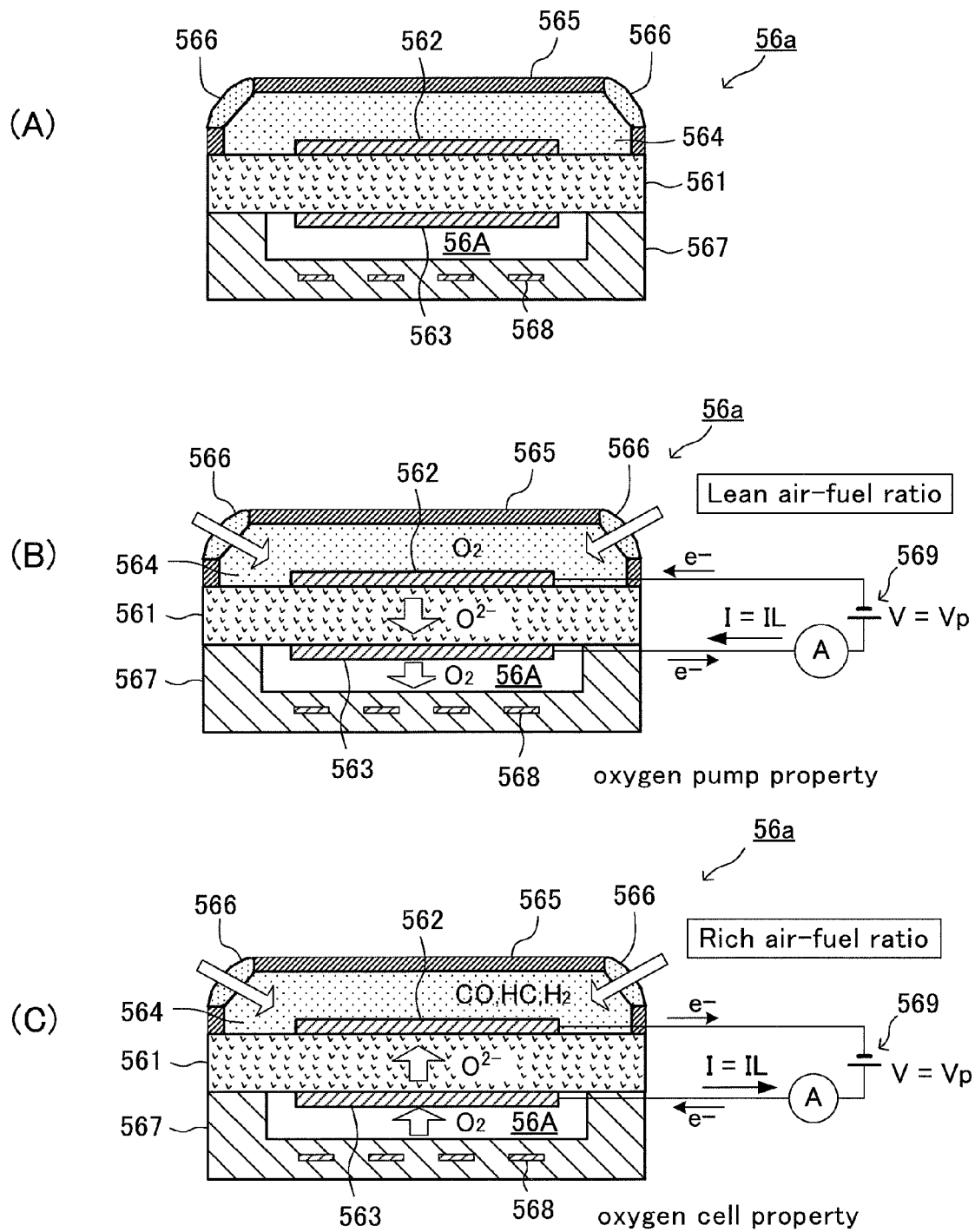
FIG. 3 Each of (A) to (C) of FIG. 3 is a schematic sectional view of an air-fuel ratio detection section of the air-fuel ratio sensor (upstream air-fuel ratio sensor) shown in FIG. 1.

As shown in FIG. 3, the upstream air-fuel ratio sensor 56 includes an air-fuel ratio detection section 56a. The air-fuel ratio detection section 56a is accommodated in an unillustrated "protective cover which is a hollow cylinder formed of metal." Through holes are formed in its peripheral wall and in its bottom wall. The exhaust gas flows into the protective cover through the through holes formed in the peripheral wall, reaches the air-fuel ratio detection section 56a, and thereafter, flows out to the outside of the protective cover through the through holes formed in the bottom wall.

That is, the exhaust gas reaching the protective cover is sucked into the inside of the protective cover owing to the flow (stream) of the exhaust gas flowing in the vicinity of the through holes formed in the bottom wall of the protective cover. Thus, a flow rate of the exhaust gas in the protective cover varies depending on the flow rate of the exhaust gas flowing in the vicinity of the through holes formed in the bottom wall of the protective cover (and accordingly, depending on the intake air-flow amount (rate) Ga which is the intake air amount per unit time). Accordingly, the output responsivity (responsivity) of the upstream air-fuel ratio sensor 56 with respect to the "air-fuel ratio of the exhaust gas flowing through the exhaust passage" becomes higher (better) as the intake air amount Ga becomes greater, but the output responsivity hardly varies depending on the engine rotational speed NE.

As shown in (A) to (C) of FIG. 3, the air-fuel ratio detection section 56a includes a solid electrolyte layer 561, an exhaust-gas-side electrode layer 562, an atmosphere-side electrode layer (reference-gas-side electrode layer) 563, a diffusion resistance layer 564, a first partition 565, a catalytic section 566, a second partition section 567, and a heater 568.

The solid electrolyte layer 561 is formed of an oxygen-ion-conductive sintered oxide. In this embodiment, the solid electrolyte layer 561 is a "stabilized zirconia element" which is a solid solution of $ZrO_2$ (zirconia) and CaO (stabilizer). The solid electrolyte layer 561 exhibits an "oxygen cell property" and an "oxygen pump property," which are well known, when its temperature is equal to or higher than an activation temperature.

The exhaust-gas-side electrode layer 562 is formed of a noble metal having a high catalytic activity, such as platinum (Pt). The exhaust-gas-side electrode layer 562 is formed on one of surfaces of the solid electrolyte layer 561. The exhaust-gas-side electrode layer 562 is formed through chemical plating, etc. so as to exhibit an adequate permeability (that is, it is formed into a porous layer).

The atmosphere-side electrode layer 563 is formed of a noble metal having a high catalytic activity, such as platinum (Pt). The atmosphere-side electrode layer 563 is formed on the other one of surfaces of the solid electrolyte layer 561 in such a manner it faces the exhaust-gas-side electrode layer 562 across the solid electrolyte layer 561. The atmosphere-side electrode layer 563 is formed through chemical plating, etc. so as to exhibit an adequate permeability (that is, it is formed into a porous layer). The atmosphere-side electrode layer 563 is also referred to as a reference-gas-side electrode layer.

The diffusion resistance layer (diffusion-controlling layer) 564 is a porous layer formed of a porous ceramic material (heat-resistant inorganic material). The diffusion resistance layer 564 is formed through, for example, plasma spraying in such a manner that it covers the outer surface of the exhaust-gas-side electrode layer 562.

The first partition section 565 is formed of dense and gas-nonpermeable alumina ceramic. The first partition section 565 is formed so as to cover the diffusion resistance layer 564 except corners (portions) of the diffusion resistance layer 564. That is, the first partition section 565 has pass-through portions which expose portions of the diffusion resistance layer 564 to outside.

The catalytic section 566 is formed in the pass-through portions of the first partition section 565 so as to close the pass-through portions. The catalytic section 566 includes the catalytic substance which facilitates an oxidation-reduction reaction and a substance for storing oxygen which exerts the oxygen storage function, similarly to the upstream catalyst 43. The catalytic section 566 is porous. Accordingly, as shown by a white painted arrows in (B) and (C) of FIG. 3, the exhaust gas (the above described exhaust gas flowing into the inside of the protective cover) reaches the diffusion resistance layer 564 through the catalytic section 566, and then further reaches the exhaust-gas-side electrode layer 562 through the diffusion resistance layer 564.

The second partition section 567 is formed of dense and gas-nonpermeable alumina ceramic. The second partition section 567 is configured so as to form an "atmosphere chamber 56A" which is a space that accommodates the atmosphere-side electrode layer 563. Air is introduced into the atmosphere chamber 56A.

A power supply 569 is connected to the upstream air-fuel ratio sensor 56. The power supply 569 applies a voltage V (=Vp) in such a manner that the atmosphere-side electrode layer 563 is held at a high potential and the exhaust-gas-side electrode layer 562 is held at a low potential.

The heater 568 is buried in the second partition section 567. The heater 568 generates heat when energized by the electric controller 70 described later so as to heat up the solid electrolyte layer 561, the exhaust-gas-side electrode layer 562, and the atmosphere-side electrode layer 563 in order to control temperatures of those layers.

Figure 4:
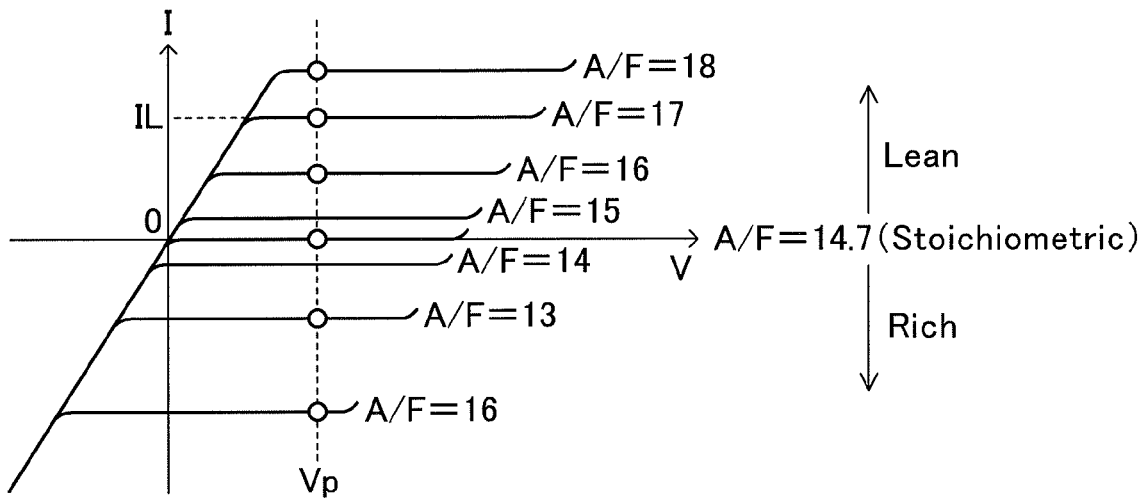
FIG. 4 is a graph showing a relationship between an air-fuel ratio of an exhaust gas and a limiting current value of the air-fuel ratio sensor.

As shown in (B) of FIG. 3, when the air-fuel ratio of the exhaust gas is leaner than the stoichiometric air-fuel ratio, the thus configured upstream air-fuel ratio sensor 56 ionizes oxygen which has reached the exhaust-gas-side electrode layer 562 through the diffusion resistance layer 564, and makes the ionized oxygen reach the atmosphere-side electrode layer 563. As a result, an electrical current I flows from a positive electrode of the electric power supply 569 to a negative electrode of the electric power supply 569. As shown in FIG. 4, the magnitude of the electrical current I becomes a constant value which corresponds to an amount of oxygen arriving at the exhaust-gas-side electrode layer 562 (or an oxygen partial pressure, an oxygen concentration, and thus, the air-fuel ratio of the exhaust gas), when the electric voltage V is set at a predetermined value Vp or higher. The upstream air-fuel ratio sensor 56 outputs a voltage value into which this electrical current (i.e., the limiting current IL) is converted, as its output value Vabyfs.

To the contrary, as shown in (C) of FIG. 3, when the air-fuel ratio of the exhaust gas is richer than the stoichiometric air-fuel ratio, the upstream air-fuel ratio sensor 56 ionizes oxygen which is present in the atmosphere chamber 56A and makes the ionized oxygen reach the exhaust-gas-side electrode layer 562 so as to oxide the unburned substances (combustibles) (HC, CO, and $H_2$, etc.) reaching the exhaust-gas-side electrode layer 562 through the diffusion resistance layer 564. As a result, an electrical current I flows from the negative electrode of the electric power supply 569 to the positive electrode of the electric power supply 569. As shown in FIG. 4, the magnitude of the electrical current I also becomes a constant value which corresponds to an amount of the unburned combustibles arriving at the exhaust-gas-side electrode layer 562 (a partial pressure of the unburned combustibles, a concentration of the unburned combustibles, and thus, the air-fuel ratio of the exhaust gas), when the electric voltage V is set at the predetermined value Vp or higher. The upstream air-fuel ratio sensor 56 outputs a voltage value into which the electrical current (i.e., the limiting current IL) is converted, as its output value Vabyfs.

Figure 5:
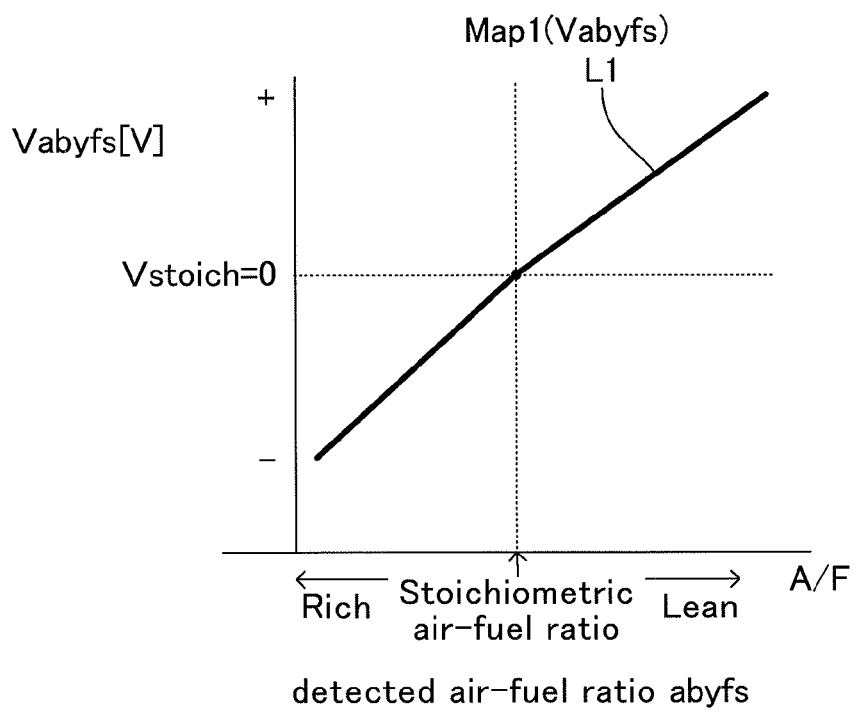
FIG. 5 is a graph showing a relationship between the air-fuel ratio of the exhaust gas and an output value of the air-fuel ratio sensor.

That is, the air-fuel detection section 56a, as shown by a solid line L1 in FIG. 5, outputs, as an "air-fuel ratio sensor output", the output value Vabyfs which corresponds to the air-fuel ratio of the gas which is flowing at the position at which the upstream air-fuel ratio sensor 56 is disposed and is reaching the air-fuel detection section 56a through the through holes of the protective cover. In other words, the upstream air-fuel ratio sensor 56 outputs the output value Vabyfs which varies depending on "the oxygen partial pressure (oxygen concentration, oxygen amount) and the unburnt substance partial pressure (unburnt substance concentration, unburnt substance amount)" of the gas reaching the exhaust-gas-side electrode layer 562 which has passed through the diffusion resistance layer 564 of the air-fuel detection section 56a.

This output value Vabyfs becomes larger as the air-fuel ratio of the gas reaching the air-fuel ratio detection section 56a becomes larger (leaner). That is, the output value Vabyfs changes as shown by a solid line in FIG. 5, when the non-uniformity among the cylinder-by-cylinder air-fuel ratios is not present (i.e., when the air-fuel ratios of the cylinders are the same as each other among the cylinders), and the fuel which is being used does not contain the alcohol (i.e., when the alcohol concentration is "0"). The output value Vabyfs becomes equal to a stoichiometric air-fuel ratio corresponding value Vstoich, when the air-fuel ratio of the gas reaching the air-fuel ratio detection section 56a is equal to the stoichiometric air-fuel ratio.

As described above, it can be said that "the upstream air-fuel ratio sensor 56 is an air-fuel ratio sensor, which comprises the air-fuel ratio detection section 56a including the solid electrolyte layer 561, the exhaust-gas-side electrode layer 562 formed on one of surfaces of the solid electrolyte layer 561, the diffusion resistance layer 564 which covers the exhaust-gas-side electrode layer 562 and the exhaust gas reaches, and the atmosphere-side electrode layer 563 which is formed on the other surfaces of the solid electrolyte layer 561 and is exposed in the atmosphere chamber 56A, and which outputs the output values Vabyfs being in accordance with (indicative of) the air-fuel ratio of the exhaust gas passing through the position at which the air-fuel ratio sensor 56 is disposed."

Meanwhile, the unburnt substances including hydrogen that are contained in the exhaust gas are purified in the catalytic section 566 to some degree. However, the catalytic section 566 can not completely purify the unburnt substances when a great amount of the unburnt substances are contained in the exhaust gas. As a result, there may be a case in which "the oxygen and the unburnt substances that are excessive with respect to the oxygen" reach the outer surface of the diffusion resistance layer 564. Further, as described above, a molecule size of hydrogen is smaller than a molecule size of the other unburnt substances, and thus, the hydrogen preferentially diffuses through the diffusion resistance layer 564 as compared with the other unburnt substances.

Referring back to FIG. 1, the downstream air-fuel ratio sensor 57 is disposed in the exhaust pipe 42. A position at which the downstream air-fuel ratio sensor 57 is disposed is downstream of the upstream catalyst 43 and upstream of the downstream catalyst (i.e., in the exhaust passage between the upstream catalyst 43 and the downstream catalyst). The downstream air-fuel ratio sensor 57 is a well-known electromotive-force-type oxygen concentration sensor (a well-known concentration-cell-type oxygen concentration sensor using stabilized zirconia). The downstream air-fuel ratio sensor 57 is designed to generate an output value Voxs corresponding to the air-fuel ratio of a gas to be detected, the gas flowing through a portion of the exhaust passage where the downstream air-fuel ratio sensor 57 is disposed. In other words, the output value Voxs is a value corresponding to the air-fuel ratio of the gas which flows out of the upstream catalyst 43 and flows into the downstream catalyst.

Figure 6:
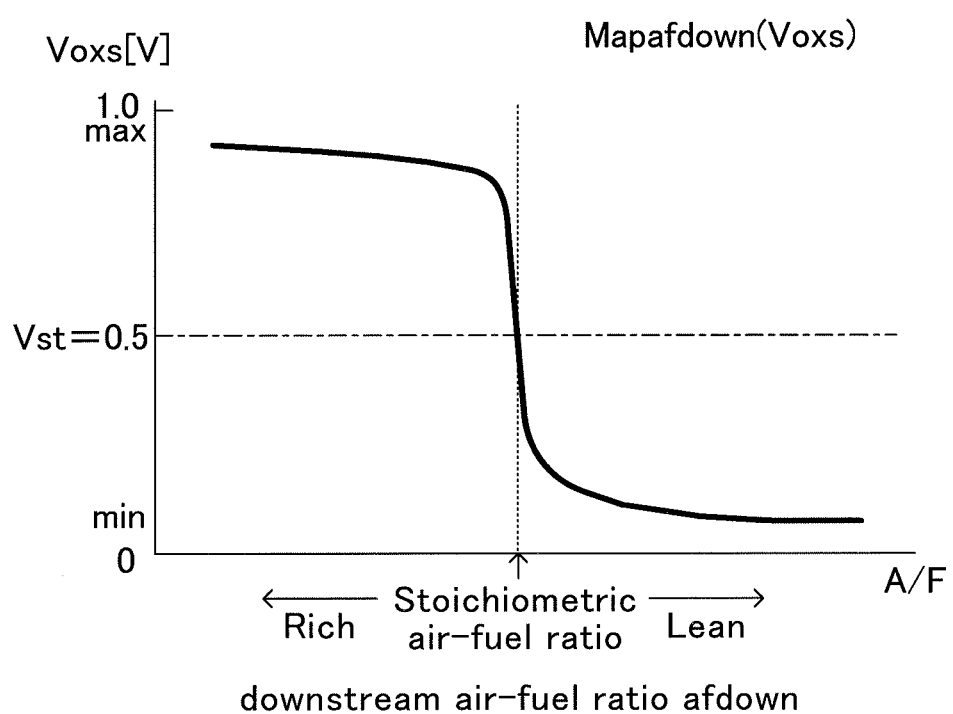
FIG. 6 is a graph showing a relationship between an air-fuel ratio of an exhaust gas and an output value of a downstream air-fuel ratio sensor shown in FIG. 1.

As shown in FIG. 6, this output value Voxs becomes a maximum output value max (e.g., about 0.9 V–1.0 V) when the air-fuel ratio of the gas to be detected is richer than the stoichiometric air-fuel ratio. The output value Voxs becomes a minimum output value min (e.g., about 0.1 V–0 V) when the air-fuel ratio of the gas to be detected is leaner than the stoichiometric air-fuel ratio. Further, the output value Voxs becomes a voltage Vst (midpoint voltage Vst, e.g., about 0.5 V) which is approximately the midpoint value between the maximum output value max and the minimum output value min when the air-fuel ratio of the gas to be detected is equal to the stoichiometric air-fuel ratio. The output value Vox drastically changes from the maximum output value max to the minimum output value min when the air-fuel ratio of the gas to be detected changes from the air-fuel ratio richer than the stoichiometric air-fuel ratio to the air-fuel ratio leaner than the stoichiometric air-fuel ratio. Similarly, the output value Vox drastically changes from the minimum output value min to the maximum output value max when the air-fuel ratio of the gas to be detected changes from the air-fuel ratio leaner than the stoichiometric air-fuel ratio to the air-fuel ratio richer than the stoichiometric air-fuel ratio.

It should be noted that the downstream air-fuel ratio sensor 57 also comprises a solid electrolyte layer, "an exhaust-gas-side electrode layer and an atmosphere-side electrode layer (a reference-gas-side electrode layer)" which are formed so as to face each other across the solid electrolyte layer. In addition, the exhaust-gas-side electrode layer is covered with a porous layer (protective layer). Accordingly, the gas to be detected changes into a gas after oxygen equilibrium (gas produced after oxygen and unburnt substances are reacted with each other) when the gas to be detected passes through the porous layer, and reaches the exhaust-gas-side electrode layer. Hydrogen passes the porous layer more easily than the other unburnt substances. Note, however, that the "excessive hydrogen produced upon the occurrence of the non-uniformity among the cylinder-by-cylinder air-fuel ratios" is eliminated by the upstream catalyst 43 except a specific case. Accordingly, the output value Voxs of the downstream air-fuel ratio sensor 57 does not vary depending on the degree of the non-uniformity among the cylinder-by-cylinder air-fuel ratios and the alcohol concentration except the specific case.

The accelerator opening sensor 58 shown in FIG. 1 is designed to output a signal which indicates the operation amount Accp of the accelerator pedal AP operated by the driver (accelerator pedal operation amount, opening degree of the accelerator pedal AP). The accelerator pedal operation amount Accp increases as the operation amount of the accelerator pedal AP becomes larger.

The alcohol concentration sensor 59 is disposed in a fuel supply pipe FP which connects a plurality of the fuel injection valves 33 with an unillustrated fuel tank. The alcohol concentration sensor 59 is designed so as to output a signal Et which represents (is indicative of) a concentration of alcohol (ethanol) contained in the fuel F. The alcohol concentration sensor 59 is well-known (refer to, for example, Japanese Patent Application Laid-Open (kokai) Nos. 2005-201670, and Hei 7-77507). The alcohol concentration sensor 59 may be a capacitance sensor which detects the alcohol concentration based on a permittivity of the fuel F, or may be an optical sensor which detects the alcohol concentration based on a refraction index, a transmissivity, or the like, of the fuel F.

The electric controller 70 is a well-known microcomputer which includes "a CPU; a ROM in which programs executed by the CPU, tables (maps and/or functions), constants, etc. are stored in advance; a RAM in which the CPU temporarily stores data as needed; a backup RAM; and an interface which includes an AD converter, etc."

The backup RAM is supplied with an electric power from a battery mounted on a vehicle on which the engine 10 is mounted, regardless of a position (off-position, start position, on-position, and so on) of an unillustrated ignition key switch of the vehicle. While the electric power is supplied to the backup RAM, data is stored in (written into) the backup RAM according to an instruction of the CPU, and the backup RAM holds (retains, stores) the data in such a manner that the data can be read out. Accordingly, the backup RAM can keep the data while the engine 10 is stopped.

When the battery is taken out from the vehicle, for example, and thus, when the backup RAM is not supplied with the electric power, the backup RAM can not hold the data. Accordingly, the CPU initializes the data to be stored (sets the data to default values) in the backup RAM when the electric power starts to be supplied to the backup RAM again. The backup RAM may be replaced with a nonvolatile readable and writable memory such as an EEPROM.

The electric controller 70 is connected to sensors described above so as to send signals from those sensors to the CPU. In addition, the electric controller 70 is designed to send drive signals (instruction signals) to each of the spark plugs (in actuality, the igniters) provided for each of the cylinders, each of the fuel injection valves 33 provided for each of the cylinders, the throttle valve actuator, and the like, in response to instructions from the CPU.

The electric controller 70 is designed to send the instruction signal to the throttle valve actuator so that the throttle valve opening TA increases as the obtained accelerator pedal operation amount Accp increases. That is, the electric controller 70 has a throttle valve drive section for changing the opening of the "throttle valve 34 disposed in the intake passage of the engine 10" in accordance with the acceleration operation amount (accelerator pedal operation amount Accp) of the engine 10 which is changed by the driver.

(An Outline of a Fuel Injection Amount Control by the First Control Apparatus)

An outline of a fuel injection amount control (air-fuel ratio feedback control) by the first control apparatus will next be described.

1. A Relationship Between the Output Value of the Air-Fuel Ratio Sensor 56 and the Alcohol Concentration A "greater amount of hydrogen" is produced by the combustion of the fuel, as the alcohol concentration of the fuel (in the present example, ethanol ratio) becomes larger (higher). Therefore, as the alcohol concentration of the fuel becomes higher, an amount of hydrogen reaching the outer surface of the diffusion resistance layer 564 of the upstream air-fuel ratio sensor 56 becomes larger. Consequently, a concentration (partial pressure) of hydrogen reaching the exhaust-gas-side electrode layer 562 when the alcohol concentration is high becomes significantly higher than a concentration (partial pressure) of hydrogen reaching the exhaust-gas-side electrode layer 562 when the alcohol concentration is low.

Figure 7:
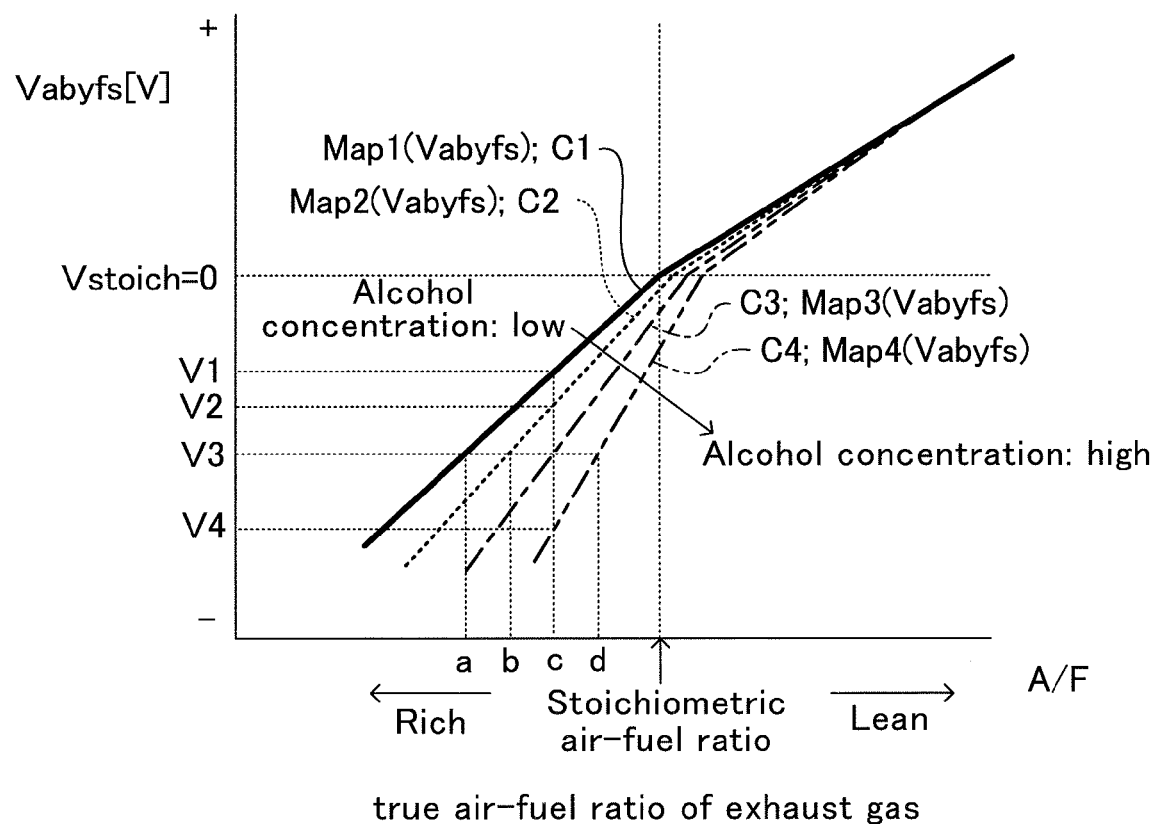
FIG. 7 is a graph showing a relationship between an alcohol concentration, a true air-fuel ratio of the exhaust gas, and the output value of the air-fuel ratio sensor.

Accordingly, as shown in FIG. 7, the output value Vabyfs of the upstream air-fuel ratio sensor 56 shifts to a value corresponding an air-fuel ratio in a "richer side" with respect to the true air-fuel ratio of the engine (true air-fuel ratio of the exhaust gas), as the alcohol concentration becomes higher. In other words, the output value Vabyfs becomes smaller as the alcohol concentration becomes higher, even when the true air-fuel ratio of the exhaust gas is unchanged. It should be noted that each of lines shown in FIG. 7 shows a "relationship between the output value Vabyfs and the true air-fuel ratio of the exhaust gas" in the each of the following cases, in a case in which the non-uniformity among the cylinder-by-cylinder air-fuel ratios is not occurring.

Solid line C1: A case in which the alcohol concentration is equal to "0." In this case, the alcohol concentration is expressed as a "first concentration, or a base (reference) alcohol concentration". It should be noted that the solid line C1 coincides with the solid line L1 shown in FIG. 5.

Broken line C2: A case in which the alcohol concentration is equal to a "second concentration higher than the first concentration."

Alternate long and short dash line C3: A case in which the alcohol concentration is equal to a "third concentration higher than the second concentration."

Alternate long and two short dashes line C4: A case in which the alcohol concentration is equal to a "fourth concentration higher than the third concentration."

It is assumed that the true air-fuel ratio of the exhaust gas is equal to a "value c shown in FIG. 7." In this case, the output value Vabyfs becomes equal to V1, V2, V3, and V4 (V1>V2>V3>V4) when the alcohol concentration is equal to the first, second, third, and fourth concentration, respectively. That is, as described above, the output value Vabyfs becomes smaller as the alcohol concentration becomes higher even when the true air-fuel ratio of the exhaust gas remains unchanged.

It is assumed that the electric controller 70 is configured so as to store, as an "air-fuel ratio conversion table Map1 (Vabyfs)", the "relationship shown by the solid line C1 in FIG. 7 (solid line L1 shown in FIG. 5)" only, and so as to convert the actual output value Vabyfs into an air-fuel ratio using the air-fuel ratio conversion table Map1(Vabyfs).

Under this assumption, when the actual output value Vabyfs is equal to the "value V3 shown in FIG. 7", for example, the air-fuel ratio converted by the air-fuel ratio conversion table Map1(Vabyfs) is an air-fuel ratio a. That is, the electric controller 70 recognizes that the air-fuel ratio of the exhaust gas is "a."

However, the true air-fuel ratio of the exhaust gas is b (b>a) if the alcohol concentration is equal to the second concentration, the true air-fuel ratio of the exhaust gas is c (c>b) if the alcohol concentration is equal to the third concentration, the true air-fuel ratio of the exhaust gas is d (d>c) if the alcohol concentration is equal to the fourth concentration. In this manner, when the actual output value Vabyfs is a "certain constant value", the "air-fuel ratio obtained by the air-fuel ratio conversion table Map1(Vabyfs)" becomes an air-fuel ratio in the richer side (smaller air-fuel ratio) in relation to the "true air-fuel ratio of the exhaust gas", as the alcohol concentration becomes higher. This is the reason why the "erroneous lean control due to the alcohol concentration" occurs.

2. A Relationship Between the Output Value of the Air-Fuel Ratio Sensor 56 and the Degree of the Non-Uniformity Among the Cylinder-by-Cylinder Air-Fuel Ratios Meanwhile, even if the alcohol concentration remains unchanged, a "greater amount of hydrogen" is produced, as the degree of the non-uniformity among the cylinder-by-cylinder air-fuel ratios becomes larger. Therefore, as the degree of the non-uniformity among the cylinder-by-cylinder air-fuel ratios becomes larger, an amount of hydrogen reaching the outer surface of the diffusion resistance layer 564 becomes larger. Consequently, a concentration (partial pressure) of hydrogen reaching the exhaust-gas-side electrode layer 562 when the degree of the non-uniformity among the cylinder-by-cylinder air-fuel ratios is large becomes significantly higher than a concentration (partial pressure) of hydrogen reaching the exhaust-gas-side electrode layer 562 when the degree of the non-uniformity among the cylinder-by-cylinder air-fuel ratios is small. Accordingly, as the degree of the non-uniformity among the cylinder-by-cylinder air-fuel ratios becomes larger, the output value of the upstream air-fuel ratio sensor 56 shifts to a value corresponding to an air-fuel ration in the richer side in relation to the true air-fuel ratio of the engine 10 (true air-fuel ratio of the exhaust gas).

Figure 8:
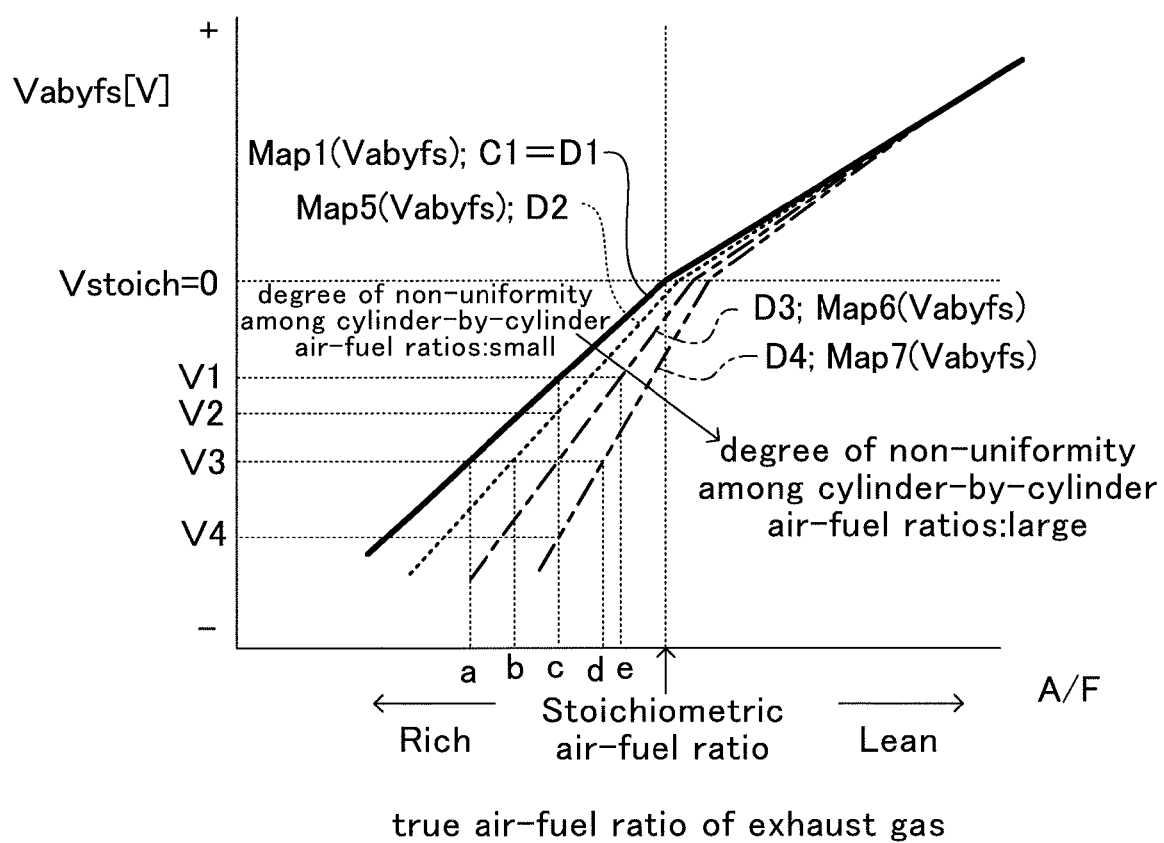
FIG. 8 is a graph showing a relationship between a degree of the non-uniformity among the cylinder-by-cylinder air-fuel ratios, a true air-fuel ratio of the exhaust gas, and the output value of the air-fuel ratio sensor.

That is, as shown in FIG. 8, the output value Vabyfs of the upstream air-fuel ratio sensor 56 shifts to a value corresponding an air-fuel ratio in the "richer side" (smaller air-fuel ratio) with respect to the true air-fuel ratio of the exhaust gas, as the degree of the non-uniformity among the cylinder-by-cylinder air-fuel ratios becomes larger. In other words, the output value Vabyfs becomes smaller as the degree of the non-uniformity among the cylinder-by-cylinder air-fuel ratios becomes larger. It should be noted that each of lines shown in FIG. 8 shows a "relationship between the output value Vabyfs and the true air-fuel ratio of the exhaust gas" in the each of the following cases, in a case in which the alcohol concentration is equal to the base (reference) alcohol concentration (in the present example, "0").

Solid line D1: A case in which the non-uniformity among the cylinder-by-cylinder air-fuel ratios is not occurring. In this case, the degree of the non-uniformity among the cylinder-by-cylinder air-fuel ratios is expressed as a "first degree". It should be noted that the solid line D1 coincides with the solid line L1 shown in FIG. 5.

Broken line D2: A case in which the non-uniformity among the cylinder-by-cylinder air-fuel ratios is present, and the degree of the non-uniformity among the cylinder-by-cylinder air-fuel ratios is a "second degree larger than the first degree."

Alternate long and short dash line D3: A case in which the non-uniformity among the cylinder-by-cylinder air-fuel ratios is present, and the degree of the non-uniformity among the cylinder-by-cylinder air-fuel ratios is a "third degree larger than the second degree."

Alternate long and two short dashes line D4: A case in which the non-uniformity among the cylinder-by-cylinder air-fuel ratios is present, and the degree of the non-uniformity among the cylinder-by-cylinder air-fuel ratios is a "fourth degree larger than the third degree."

It is assumed here that the true air-fuel ratio of the exhaust gas is equal to a "value c shown in FIG. 8." In this case, the output value Vabyfs becomes equal to V1, V2, V3, and V4 (V1>V2>V3>V4) when the degree of the non-uniformity among the cylinder-by-cylinder air-fuel ratios is equal to the first, second, third, and fourth degree, respectively. That is, as described above, the output value Vabyfs becomes smaller as the degree of the non-uniformity among the cylinder-by-cylinder air-fuel ratios becomes larger, even when the true air-fuel ratio of the exhaust gas remains unchanged.

Under this assumption, when the actual output value Vabyfs is equal to the "value V3 shown in FIG. 8", for example, the air-fuel ratio converted by the air-fuel ratio conversion table Map1(Vabyfs) is an air-fuel ratio a. That is, the electric controller 70 recognizes that the air-fuel ratio of the exhaust gas is "a."

However, the true air-fuel ratio of the exhaust gas is b (b>a) if the degree of the non-uniformity among the cylinder-by-cylinder air-fuel ratios is the second degree, the true air-fuel ratio of the exhaust gas is c (c>b) if the degree of the non-uniformity among the cylinder-by-cylinder air-fuel ratios is the third degree, and the true air-fuel ratio of the exhaust gas is d (d>c) if the degree of the non-uniformity among the cylinder-by-cylinder air-fuel ratios is the fourth degree. In this manner, when the actual output value Vabyfs is a "certain constant value", the "air-fuel ratio obtained by the air-fuel ratio conversion table Map1(Vabyfs)" becomes an air-fuel ratio in the richer side (smaller air-fuel ratio) in relation to the "true air-fuel ratio of the exhaust gas", as the degree of the non-uniformity among the cylinder-by-cylinder air-fuel ratios becomes larger. This is the reason why the "erroneous lean control due to the non-uniformity among the cylinder-by-cylinder air-fuel ratios" occurs.

3. A Conversion of the Output Value of the Air-Fuel Ratio Sensor 56 into an Air-Fuel Ratio As described above, when the actual output value Vabyfs is a "certain value", the output value Vabyfs of the upstream air-fuel ratio sensor 56 varies depending on "the alcohol concentration and the degree of the non-uniformity among the cylinder-by-cylinder air-fuel ratios." Accordingly, if a relationship between the output value Vabyfs of the upstream air-fuel ratio sensor 56 and the true air-fuel ratio of the exhaust gas is obtained for various alcohol concentrations and various degrees of the non-uniformity among the cylinder-by-cylinder air-fuel ratios in advance by experiments or the like, it is possible to obtain the "true air-fuel ratio of the exhaust gas" based on that relationship and "the actual output value Vabyfs, the actual alcohol concentration, and the actual degree of the non-uniformity among the cylinder-by-cylinder air-fuel ratios." It should be noted that the relationship between the "output value Vabyfs of the upstream air-fuel ratio sensor 56" and a "parameter (first air-fuel ratio correlated parameter) representing the true air-fuel ratio of the exhaust gas" is referred to as a "first relationship." Accordingly, the relationship among "the alcohol concentration, the degree of the non-uniformity among the cylinder-by-cylinder air-fuel ratios, the output value Vabyfs, and the true air-fuel ratio of the exhaust gas" is one of the "first relationships."

As described later, the actual degree of the non-uniformity among the cylinder-by-cylinder air-fuel ratios is represented/expressed by an air-fuel ratio imbalance indicating value RIMB. The air-fuel ratio imbalance indicating value RIMB is a value which becomes larger as the degree of the non-uniformity among the cylinder-by-cylinder air-fuel ratios becomes larger. The actual alcohol concentration Et can be detected by the alcohol concentration sensor 59.

In view of the above, the first control apparatus stores a "look-up table defining the first relationship" shown in the Table 1 below in the ROM, and obtains the actual air-fuel ratio of the exhaust gas (hereinafter, referred to as an "actual detected air-fuel ratio abyfsact") by applying the actual alcohol concentration Et, the actual air-fuel ratio imbalance indicating value RIMB, and the actual output value Vabyfs to the look-up table. A "conversion of the output value Vabyfs into the actual detected air-fuel ratio abyfsact" according to the look-up table shown in the Table 1 can be expressed by a function fa. In this case, the equation abyfsact=fa(Et, RIMB, Vabyfs) can be satisfied. The actual detected air-fuel ratio abyfsact is also referred to as a "first air-fuel ratio correlated parameter."

When using the look-up table shown in the Table 1 (first relationship), the output value Vabyfs of the upstream air-fuel ratio sensor 56 is converted into an air-fuel ratio (i.e., the actual detected air-fuel ratio abyfsact), which becomes larger as the actual alcohol concentration Et becomes higher, and which becomes larger as the air-fuel ratio imbalance indicating value RIMB becomes larger. This converted air-fuel ratio (actual detected air-fuel ratio abyfsact) is the first air-fuel ratio correlated parameter.

Consequently, the first control apparatus can obtain the actual detected air-fuel ratio abyfsact representing the true air-fuel ratio of the exhaust gas. Thereafter, the first control apparatus performs the main feedback control in such a manner that the actual detected air-fuel ratio abyfsact coincides with a target air-fuel ratio abyfr. As a result, since the erroneous lean control does not occur, the "increase of the discharge amount of NOx due to the erroneous lean control" can be avoided.

TABLE 1

| Input | | | Output |
|---|---|---|---|
| alcohol concentration Et | air-fuel ratio imbalance indicating value RIMB | output value Vabyfs of air-fuel ratio sensor | actual detected air-fuel ratio abyfsact |
| 0 | 0 | v1 | af(0,0,v1) |
| 0 | 0 | v2 | af(0,0,v2) |
| . | . | . | . |
| . | . | . | . |
| 0 | 0 | vn | af(0,0,vn) |
| 0 | r1 | v1 | af(0,r1,v1) |
| 0 | r1 | v2 | af(0,r1,v2) |
| . | . | . | . |
| . | . | . | . |
| 0 | r1 | vn | af(0,r1,vn) |
| 0 | r2 | v1 | af(0,r2,v1) |
| 0 | r2 | v2 | af(0,r2,v2) |
| . | . | . | . |
| . | . | . | . |
| 0 | r3 | v1 | af(0,r3,v1) |
| . | . | . | . |
| . | . | . | . |
| . | . | . | . |
| 0 | rn | vn | af(0,rn,vn) |
| e1 | 0 | v1 | af(e1,0,v1) |
| e1 | 0 | v2 | af(e1,0,v2) |
| . | . | . | . |
| . | . | . | . |
| e1 | 0 | vn | af(e1,0,vn) |
| e1 | r1 | v1 | af(e1,r1,v1) |
| e1 | r1 | v2 | af(e1,r1,v2) |
| . | . | . | . |
| . | . | . | . |
| e1 | r1 | vn | af(e1,r1,vn) |
| e1 | r2 | v1 | af(e1,r2,v1) |
| e1 | r2 | v2 | af(e1,r2,v2) |
| . | . | . | . |
| . | . | . | . |
| e1 | r3 | v1 | af(e1,r3,v1) |
| . | . | . | . |
| . | . | . | . |
| . | . | . | . |
| e1 | rn | vn | af(e1,rn,vn) |
| e2 | 0 | v1 | af(e2,0,v1) |
| e2 | 0 | v2 | af(e2,0,v2) |
| . | . | . | . |
| . | . | . | . |
| e2 | 0 | vn | af(e2,0,vn) |
| e2 | r1 | v1 | af(e2,r1,v1) |
| e2 | r1 | v2 | af(e2,r1,v2) |
| . | . | . | . |
| . | . | . | . |
| ei | rj | vk | af(ei,rj,vk) |
| . | . | . | . |
| . | . | . | . |
| en | rn | vn | af(en,rn,vn) |

(Details of the Reason why the Output Value Vabyfs Changes when the Non-Uniformity Among the Cylinder-by-Cylinder Air-Fuel Ratios has Occurred)

The reason why the output value Vabyfs changes when the non-uniformity among the cylinder-by-cylinder air-fuel ratios has occurred will next be described in more detail. It should be noted that, in the following descriptions, the alcohol concentration Et is assumed to be equal to the base (reference) value (0).

1. A Case in which the Air-Fuel Ratio of the Imbalanced Cylinder is Smaller Than the Air-Fuel Ratio of the Un-Imbalanced Cylinder For example, it is assumed that an air-fuel ratio A0/F0 is equal to the stoichiometric air-fuel ratio (e.g., 14.6), when an amount (weight) of the intake air introduced into each of the cylinders of the 4 cylinder engine is A0, and an amount (weight) of a fuel supplied to each of the cylinders is F0. Further, it is assumed that the target air-fuel ratio is the stoichiometric air-fuel ratio, for convenience of description.

Under this assumption, it is further assumed that an amount of the fuel supplied (injected) to each of the cylinders becomes uniformly excessive in (or by) 10%. That is, it is assumed that the fuel of 1.1·F0 is supplied to each of the cylinders. Here, a total amount of the intake air supplied to the four cylinders (i.e., an amount of intake air supplied to the entire engine during a period in which each and every cylinder completes one combustion stroke) is equal to 4·A0, and a total amount of the fuel supplied to the four cylinders (i.e., an amount of fuel supplied to the entire engine during the period in which each and every cylinder completes one combustion stroke) is equal to 4.4·F0(=1.1·F0+1.1·F0+1.1·F0+1.1·F0). Accordingly, a true average of the air-fuel ratio of the engine is equal to 4·A0/(4.4·F0)=A0/(1.1·F0).

Accordingly, an air-fuel ratio into which the actual output value Vabyfs is converted based on the "air-fuel ratio conversion table Map1(Vabyfs)" which is determined for a "case in which the non-uniformity among the cylinder-by-cylinder air-fuel ratios is not occurring" becomes equal to an air-fuel ratio A0/(1.1·F0).

Consequently, by the main feedback control, the air-fuel ratio of the mixture supplied to the entire engine is caused to coincide with the "stoichiometric air-fuel ratio A0/F0 serving as the target air-fuel ratio." That is, the amount of the fuel supplied to each of the cylinders is decreased in (by) 10% based on the air-fuel ratio feedback amount calculated by the main feedback control. As a result, the fuel of 1·F0 is supplied to the each of the cylinders. That is, the air-fuel ratio of each of the cylinders becomes equal to the stoichiometric air-fuel ratio A0/F0 in each of the cylinders.

Next, it is assumed that an amount of the fuel supplied to one certain specific cylinder is excessive in (by) 40% (i.e., 1.4·F0), and an amount of the fuel supplied to each of the remaining three cylinders is equal to an appropriate amount (a fuel amount required to have each of the air-fuel ratios of the cylinders coincide with the stoichiometric air-fuel ratio, (i.e., F0, in this example)).

Under this assumption, a total amount of the air supplied to the four cylinders is equal to 4·A0. A total amount of the fuel supplied to the four cylinders is equal to 4.4·F0 (=1.4·F0+F0+F0+F0). Accordingly, the true average of the air-fuel ratio of the engine is equal to 4·A0/(4.4·F0)=A0/(1.1·F0). That is, the true average of the air-fuel ratio of the engine in this case is equal to the value obtained "when the amount of the fuel supplied to each of the cylinders is uniformly excessive in (by) 10%" described above.

Figure 2:
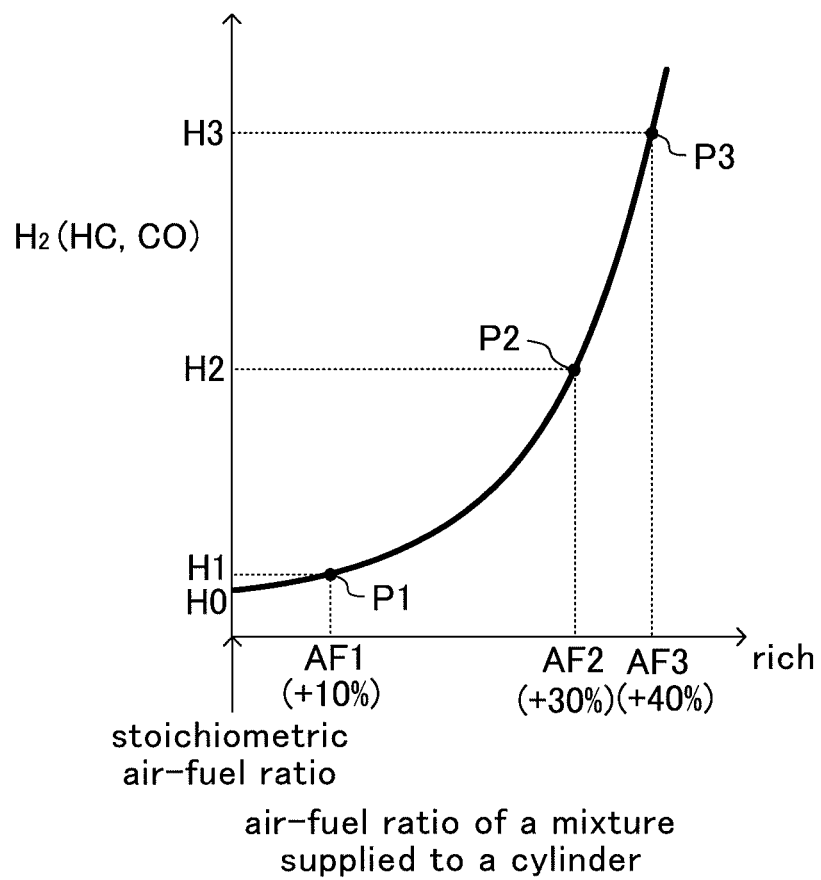
FIG. 2 is a graph showing a relationship between an air-fuel ratio of a mixture supplied to a cylinder and an amount of unburnt substances discharged from that cylinder.

However, as shown in FIG. 2, amount of the unburnt substances (HC, CO, and $H_2$) in the exhaust gas drastically increases, as the air-fuel ratio of the mixture supplied to the cylinder becomes richer. Accordingly, an "amount of hydrogen $H_2$ included in the exhaust gas discharged from the four cylinders in the case in which only the amount of the fuel supplied to the certain cylinder becomes excessive in (by) 40%" becomes prominently greater than an "amount of hydrogen $H_2$ included in the exhaust gas discharged from the four cylinders in the case in which the amount of the fuel supplied to each of the cylinders is uniformly excessive in (by) 10%."

Consequently, due to the "preferential diffusion of hydrogen" described above, the output value of the air-fuel ratio sensor 56 becomes a value corresponding to an air-fuel ratio richer than the "true air-fuel ratio (A0/(1.1·F0)) of the engine." That is, even when the average of the air-fuel ratio of the exhaust gas is a "certain air-fuel ratio in the rich side", a concentration of hydrogen $H_2$ reaching the exhaust-gas-side electrode layer of the air-fuel ratio sensor 56 when the degree of the non-uniformity among the cylinder-by-cylinder air-fuel ratios is large is prominently higher than that when the degree of the non-uniformity among the cylinder-by-cylinder air-fuel ratios is small. Accordingly, the air-fuel ratio into which the output value of the air-fuel ratio sensor 56 is converted based on the air-fuel ratio conversion table Map1 (Vabyfs) becomes an air-fuel ratio richer than the true air-fuel ratio of the engine. As a result, the erroneous lean control occurs in the conventional apparatus.

2. A Case in which the Air-Fuel Ratio of the Imbalanced Cylinder is Larger Than the Air-Fuel Ratio of the Un-Imbalanced Cylinder This state occurs, for example, when the fuel injection characteristic of the fuel injection valve 33 provided for the specific cylinder changes to inject the fuel in (by) an amount which is considerable smaller than the instructed fuel injection amount.

Here, it is assumed that an amount of the fuel supplied to one specific cylinder (the first cylinder, for convenience) is small in (by) 40 (i.e., 0.6·F0), and an amount of the fuel supplied to each of the other three cylinders (the second, the third, and the fourth cylinder) is a fuel amount required to have each of the air-fuel ratios of the other three cylinders coincide with the stoichiometric air-fuel ratio (i.e., F0). It should be noted it is assumed that a misfiring does not occur.

In this case, by the main feedback control, it is further assumed that the amount of the fuel supplied to each of the first to fourth cylinders is increased in the same amount (10%) to each other. At this time, the amount of the fuel supplied to the first cylinder is equal to 0.7·F0, and the amount of the fuel supplied to each of the second to fourth cylinders is equal to 1.1·F0.

Under this assumption, a total amount of the air supplied to the engine 10 which is the four cylinder engine (an amount of air supplied to the entire engine 10 during the period in which each and every cylinder completes one combustion stroke) is equal to 4·A0. A total amount of the fuel supplied to the engine 10 (an amount of fuel supplied to the entire engine 10 during the period in which each and every cylinder completes one combustion stroke) is equal to 4.0·F0 (=0.7·F0+1.1·F0+ 1.1·F0+1.1·F0), as a result of the main feedback control. Consequently, the true average of the air-fuel ratio of the mixture supplied to the entire engine 10 is equal to 4·A0/(4·F0)=A0/F0, that is the stoichiometric air-fuel ratio.

However, in actuality, a "total amount S1 of hydrogen $H_2$ included in the exhaust gas" in this case is equal to S1=H4+ H1+H1+H1=H4+3·H1 (refer to FIG. 2). H4 is an amount of hydrogen generated when the air-fuel ratio is equal to A0/

(0.7·F0), and is roughly equal to H0 (which is an amount of hydrogen generated when the air-fuel ratio is equal to the stoichiometric air-fuel ratio).

In contrast, when the inter-cylinder air-fuel ratio imbalance is not occurring, and the air-fuel ratio of each cylinder is equal to the stoichiometric air-fuel ratio, a "total amount S2 of hydrogen $H_2$ included in the exhaust gas" is equal to S2=H0+H0+H0+H0=4·H0. Accordingly, the total amount S1 (=H4+3·H1)=H0+3·H1>the total amount S2 (=4·H0) is satisfied. Accordingly, even when the average of the true air-fuel ratio of the exhaust gas is equal to the stoichiometric air-fuel ratio, the output value Vabyfs becomes an air-fuel ratio in the richer side with respect to the stoichiometric air-fuel ratio due to the preferential diffusion of hydrogen when the non-uniformity among the cylinder-by-cylinder air-fuel ratios occurs. Consequently, the erroneous lean control occurs.

(An Outline of Obtaining the Air-Fuel Ratio Imbalance Indicating Value, and an Outline of Determining the Inter-Cylinder Air-Fuel Ratio Imbalance)

Next, methods for obtaining the air-fuel ratio imbalance indicating value and for determining the inter-cylinder air-fuel ratio imbalance, that the first control apparatus adopts, will be described. The air-fuel ratio imbalance indicating value is a parameter indicating/representing the "degree of the non-uniformity among the cylinder-by-cylinder air-fuel ratios (degree of air-fuel ratio non-uniformity among the cylinders)" caused by a change in the characteristic of the fuel injection valve 33, or the like.

The determination of the inter-cylinder air-fuel ratio imbalance is to determine whether or not the degree of the non-uniformity among the cylinder-by-cylinder air-fuel ratios becomes equal to or greater than a degree that requires a warning (degree which is not permissible in view of emissions). The first control apparatus determines whether or not the air-fuel ratio imbalance indicating value becomes equal to or larger than an imbalance determination threshold, and determines that the inter-cylinder air-fuel ratio imbalance state has occurred when the air-fuel ratio imbalance indicating value becomes equal to or larger than the imbalance determination threshold.

The first control apparatus stores a "relationship between (among) the output value Vabyfs of the upstream air-fuel ratio sensor 56, the alcohol concentration, and the true air-fuel ratio of the exhaust gas" when the non-uniformity among the cylinder-by-cylinder air-fuel ratios is not occurring. That is, a "relationship between the output value Vabyfs and the true air-fuel ratio of the exhaust gas" for each of various alcohol concentrations" (e.g., those shown by the lines C1-C4 in FIG. 7) are obtained in advance by experiments, or the like. The first control apparatus stores the relationships in the ROM in a form of a look-up table shown in a table 2 below. It should be noted that a relationship between the "output value Vabyfs of the upstream air-fuel ratio sensor 56" and a "parameter (second air-fuel ratio correlated parameter) representing/indicating the true air-fuel ratio of the exhaust gas when the non-uniformity among the cylinder-by-cylinder air-fuel ratios is not occurring" is referred to as a "second relationship." Accordingly, the relationship among (between) "the alcohol concentration, the output value Vabyfs, and the true air-fuel ratio of the exhaust gas when the non-uniformity among the cylinder-by-cylinder air-fuel ratios is not occurring" is one of the second relationships.

TABLE 2

| Input | | Output |
|---|---|---|
| alcohol concentration Et | output value Vabyfs of air-fuel ratio sensor | tentative detected air-fuel ratio abyfsvir |
| 0 | v1 | af(0,v1) |
| 0 | v2 | af(0,v2) |
| . | . | . |
| . | . | . |
| 0 | vn | af(0,vn) |
| e1 | v1 | af(e1,v1) |
| e1 | v2 | af(e1,v2) |
| . | . | . |
| . | . | . |
| e1 | vn | af(e1,vn) |
| e2 | v1 | af(e2,v1) |
| e2 | v2 | af(e2,v2) |
| . | . | . |
| . | . | . |
| e2 | vn | af(e2,vn) |
| e3 | v1 | af(e3,v1) |
| . | . | . |
| . | . | . |
| . | . | . |
| . | . | . |
| ei | vk | af(ei,vk) |
| . | . | . |
| . | . | . |
| en | v1 | af(en,v1) |
| en | v2 | af(en,v2) |
| . | . | . |
| . | . | . |
| en | vn | af(en,vn) |

The first control apparatus obtains a tentative detected air-fuel ratio abyfsvir by applying the actual alcohol concentration Et and the actual output value Vabyfs to the "look-up table defining the second relationship" shown in the table. 2. A "conversion of the output value Vabyfs into the tentative detected air-fuel ratio abyfsvir" according to the look-up table shown in the Table 2 can be expressed by a function fb. In this case, the equation abyfsvir=fb(Et, Vabyfs) can be satisfied. The tentative detected air-fuel ratio abyfsvir can be said to be an air-fuel ratio obtained based on a value which is obtained by eliminating an effect/impact on the output value Vabyfs that the alcohol concentration Et has. The tentative detected air-fuel ratio abyfsvir is also referred to as an "alcohol concentration corrected output value" or a "second air-fuel ratio correlated parameter." Since the air-fuel ratio imbalance indicating value is obtained based on the tentative detected air-fuel ratio abyfsvir, the tentative detected air-fuel ratio abyfsvir is also referred to as a "first base parameter for obtaining the air-fuel ratio imbalance indicating value."

The first control apparatus obtains the air-fuel ratio imbalance indicating value as follows.

(1) The first control apparatus obtains an "amount of change per unit time (constant sampling interval ts)" of the tentative detected air-fuel ratio abyfsvir when a predetermined parameter obtaining condition (air-fuel ratio imbalance indicating value obtaining condition) is satisfied.

If the unit time is very short, e.g., about 4 ms, the "amount of change per unit time of the tentative detected air-fuel ratio abyfsvir" can also be said as a differential value of the tentative detected air-fuel ratio abyfsvir with respect to time (i.e., temporal differential value d(abyfsvir)/dt, first-order differential value d(abyfsvir)/dt). Accordingly, the "amount of change per unit time of the tentative detected air-fuel ratio abyfsvir" is also referred to as a "detected air-fuel ratio changing rate ΔAF." Further, the detected air-fuel ratio changing rate ΔAF is also referred to as a "base indicating amount."

(2) The first control apparatus obtains an average (average value) AveΔAF of an absolute values |ΔAF| of a plurality of the detected air-fuel ratio changing rates ΔAF that are obtained in one unit combustion cycle period. The unit combustion cycle period is a period corresponding to an elapse of a crank angle required for all of the cylinders, each of which discharges the exhaust gas reaching the single air-fuel ratio sensor 56, to complete their single-time combustion strokes. The engine 10 of the present example is the straight 4-cylinder four-cycle engine, and the exhaust gases from the first to fourth cylinder reach the single air-fuel ratio sensor 56. Accordingly, the unit combustion cycle period is a period corresponding to an elapse of a 720 degree crank angle.

(3) The first control apparatus obtains an average value of the average values AveΔAF, each of which is obtained for each of a plurality of the unit combustion cycle periods, and adopts the obtained average value as the air-fuel ratio imbalance indicating value RIMB (imbalance determination parameter). The air-fuel ratio imbalance indicating value RIMB may also be referred to as an inter-cylinder air-fuel ratio imbalance ratio indicating value, or an imbalance ratio indicating value. It should be noted that the air-fuel ratio imbalance indicating value RIMB is not limited to the value obtained as described above, and may be obtained according to various manners described later.

The air-fuel ratio imbalance indicating value RIMB (value correlated to the detected air-fuel ratio changing rate ΔAF) obtained as described above is a value which becomes larger as the "degree of the non-uniformity among the cylinder-by-cylinder air-fuel ratios" becomes larger. The reason for this will next be described.

The exhaust gases from the cylinders successively reach the air-fuel ratio sensor 56 in the order of ignition (accordingly, in the order of exhaust). In a case where the non-uniformity among the cylinder-by-cylinder air-fuel ratios is not present (there is no difference among the cylinder-by-cylinder air-fuel ratios), the air-fuel ratios of the exhaust gases, which are discharged from the cylinders and reach the air-fuel ratio sensor 56, are approximately equal to one another. Accordingly, the tentative detected air-fuel ratio abyfsvir when there is no difference among the cylinder-by-cylinder air-fuel ratios varies as indicated by the broken line C1 shown in (B) of FIG. 9, for example. Consequently, as shown by the broken line C3 in (C) of FIG. 9, an absolute value of the detected air-fuel ratio changing rate ΔAF is small, when there is no difference among the cylinder-by-cylinder air-fuel ratios.

In contrast, when a characteristic of the "fuel injection valve 33 for injecting the fuel to a specific cylinder (e.g., the first cylinder)" becomes a characteristic that the "injection valve injects a greater amount of the fuel compared to the instructed fuel injection amount", the difference among the cylinder-by-cylinder air-fuel ratios becomes large. That is, a great difference is produced between the air-fuel ratio of the specific cylinder (the air-fuel ratio of the imbalanced cylinder) and the air-fuel ratios of the remaining cylinders (the air-fuel ratios of the un-imbalanced (balanced) cylinders).

Figure 9:
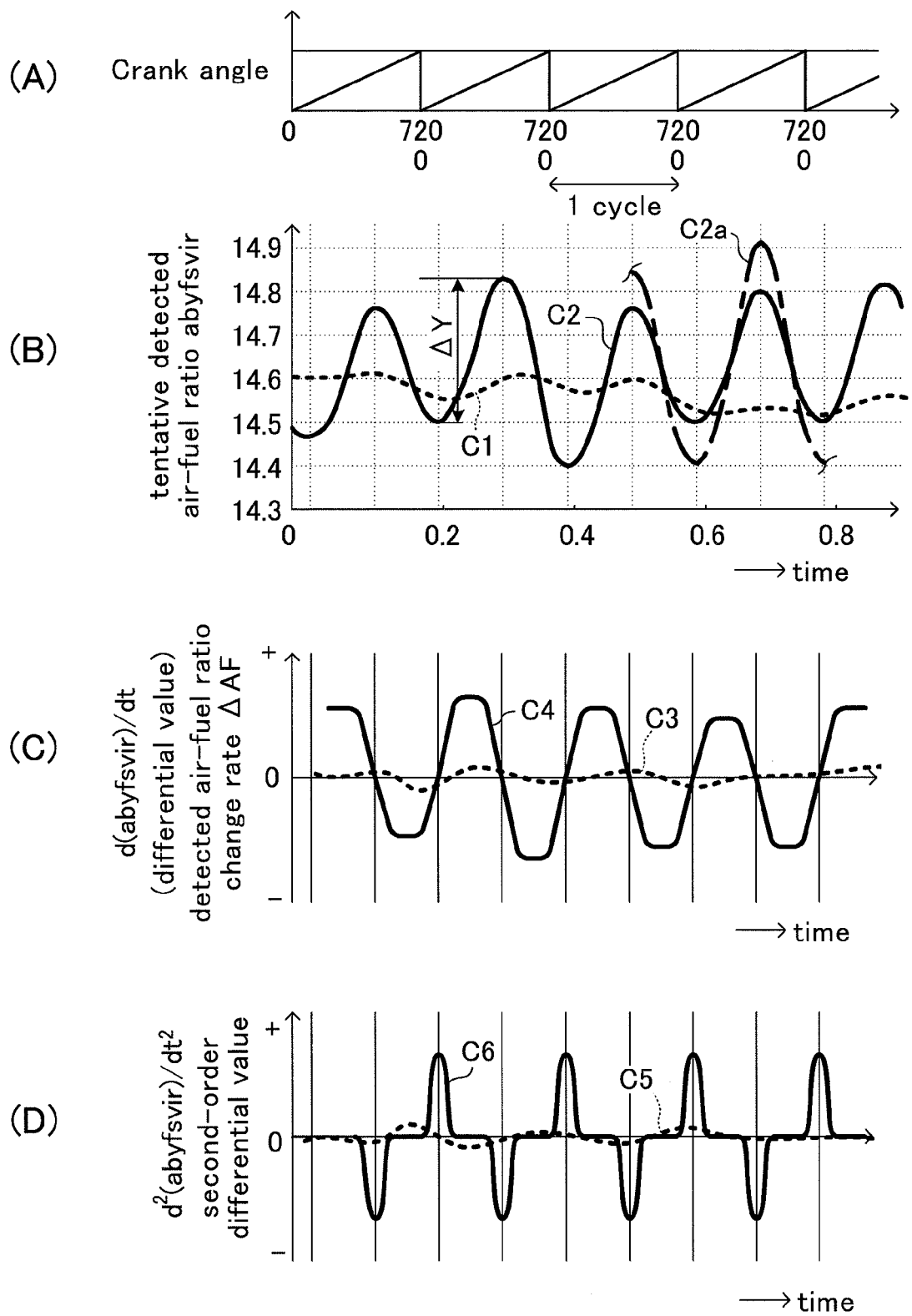
FIG. 9 is a timeline chart showing "behaviors of various values correlated to an air-fuel ratio imbalance indicating value", when an inter-cylinder air-fuel ratio imbalance state is occurring (degree of the non-uniformity among the cylinder-by-cylinder air-fuel ratios is large), and when the inter-cylinder air-fuel ratio imbalance state is not occurring (the non-uniformity among the cylinder-by-cylinder air-fuel ratios is not occurring).

Accordingly, for example, as shown by the solid line C2 in (B) of FIG. 9, the tentative detected air-fuel ratio abyfsvir when the inter-cylinder air-fuel ratio imbalance state has been occurring greatly varies/fluctuates, every unit combustion cycle period. Therefore, the absolute value of the detected air-fuel ratio changing rate ΔAF is large when the inter-cylinder air-fuel ratio imbalance state has been occurring, as shown by the solid line C4 in (C) of FIG. 9.

Further, the absolute value |ΔAF| of the detected air-fuel ratio changing rate ΔAF fluctuates/varies more greatly, as the air-fuel ratio of the imbalanced cylinder deviates more greatly from the air-fuel ratio of the un-imbalanced cylinder. For example, assuming that the tentative detected air-fuel ratio abyfsvir varies as shown by the solid line C2 in (B) of FIG. 9 when the magnitude of the difference between the air-fuel ratio of the imbalanced cylinder and the air-fuel ratio of the un-imbalanced cylinder is equal to a first value, the tentative detected air-fuel ratio abyfsvir varies as shown by the alternate long and short dash line C2a in (B) of FIG. 9 when the magnitude of the difference between the air-fuel ratio of the imbalanced cylinder and the air-fuel ratio of the un-imbalanced cylinder is a "second value larger than the first value."

Figure 10:
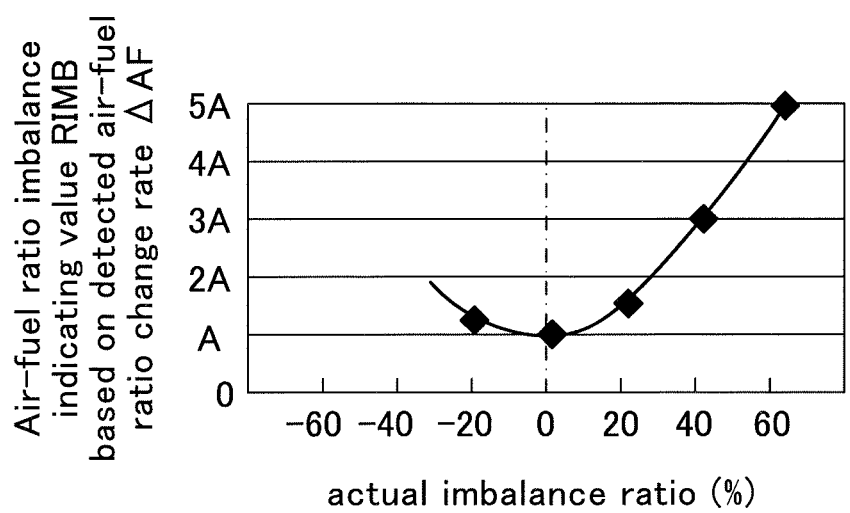
FIG. 10 is a graph showing a relationship between an actual imbalance ratio and the air-fuel ratio imbalance indicating value correlated to a detected air-fuel ratio changing rate.

Accordingly, as shown in FIG. 10, the air-fuel ratio imbalance indicating value RIMB which is correlated to the absolute values |ΔAF| of the detected air-fuel ratio changing rate ΔAF becomes larger as the actual imbalance ratio becomes greater (that is, as the air-fuel ratio of the imbalanced cylinder deviates more greatly from the air-fuel ratio of the un-imbalanced cylinder). That is, the air-fuel ratio imbalance indicating value RIMB becomes larger as the degree of the non-uniformity among the cylinder-by-cylinder air-fuel ratios becomes larger.

It should be noted that the abscissa axis of the graph shown in FIG. 10 is an "imbalance ratio (rate/fraction)." The imbalance ratio is a value "α" when an amount of the fuel supplied to the un-imbalanced cylinder is equal to "1", and an amount of the fuel supplied to the imbalanced cylinder is equal to "1+α." The imbalance ratio is typically expressed in the form of α·100%. As understood from FIG. 10, the air-fuel ratio imbalance indicating value RIMB is symmetric with respect to 0% of the imbalance ratio. That is, for example, the air-fuel ratio imbalance indicating value RIMB when the imbalance ratio is equal to +20% is roughly equal to the air-fuel ratio imbalance indicating value RIMB when the imbalance ratio is equal to −20%.

After the first control apparatus obtains the air-fuel ratio imbalance indicating value RIMB, it compares the air-fuel ratio imbalance indicating value RIMB with the imbalance determination threshold RIMBth. The first control apparatus determines that the inter-cylinder air-fuel ratio imbalance state has occurred when the air-fuel ratio imbalance indicating value RIMB is larger than the imbalance determination threshold RIMBth. In contrast, the first control apparatus determines that the inter-cylinder air-fuel ratio imbalance state has not occurred when the air-fuel ratio imbalance indicating value RIMB is smaller than the imbalance determination threshold RIMBth.

It should also be noted that the thus obtained air-fuel ratio imbalance indicating value RIMB becomes equal to a reference (base) value ("0" in this case) when the non-uniformity among the cylinder-by-cylinder air-fuel ratios is not present, and becomes larger (a magnitude of a difference between air-fuel ratio imbalance indicating value RIMB and the reference value becomes larger) as the degree of the non-uniformity among the cylinder-by-cylinder air-fuel ratios becomes larger.

It can be said that the tentative detected air-fuel ratio abyfsvir is an air-fuel ratio represented by the output value Vabyfs of the upstream air-fuel ratio sensor 56 on the assumption that the alcohol concentration is equal to a base (reference) alcohol concentration ("0", in the present example), and the air-fuel ratio imbalance indicating value RIMB is equal to a base (reference) air-fuel ratio imbalance indicating value ("0", in the present example). The reason why the tentative detected air-fuel ratio abyfsvir is adopted/used as the parameter for obtaining the air-fuel ratio imbalance indicating value RIMB, in place of the actual detected air-fuel ratio abyfsact is as follows.

It is now assumed that the degree of the non-uniformity among the cylinder-by-cylinder air-fuel ratios has changed to a certain value. At this time, if the air-fuel ratio imbalance indicating value RIMB is obtained based on the actual detected air-fuel ratio abyfsact, the actual detected air-fuel ratio abyfsact further changes due to the obtained air-fuel ratio imbalance indicating value RIMB. Accordingly, if the actual detected air-fuel ratio abyfsact is used as the base parameter for obtaining the air-fuel ratio imbalance indicating value RIMB, the air-fuel ratio imbalance indicating value RIMB varies even when the degree of the non-uniformity among the cylinder-by-cylinder air-fuel ratios remains unchanged. Therefore, it is preferable that the tentative detected air-fuel ratio abyfsvir be used for the base parameter for obtaining the air-fuel ratio imbalance indicating value RIMB, rather than the actual detected air-fuel ratio abyfsact.

(Actual Operation)

<Fuel Injection Amount Control>

Figure 11:
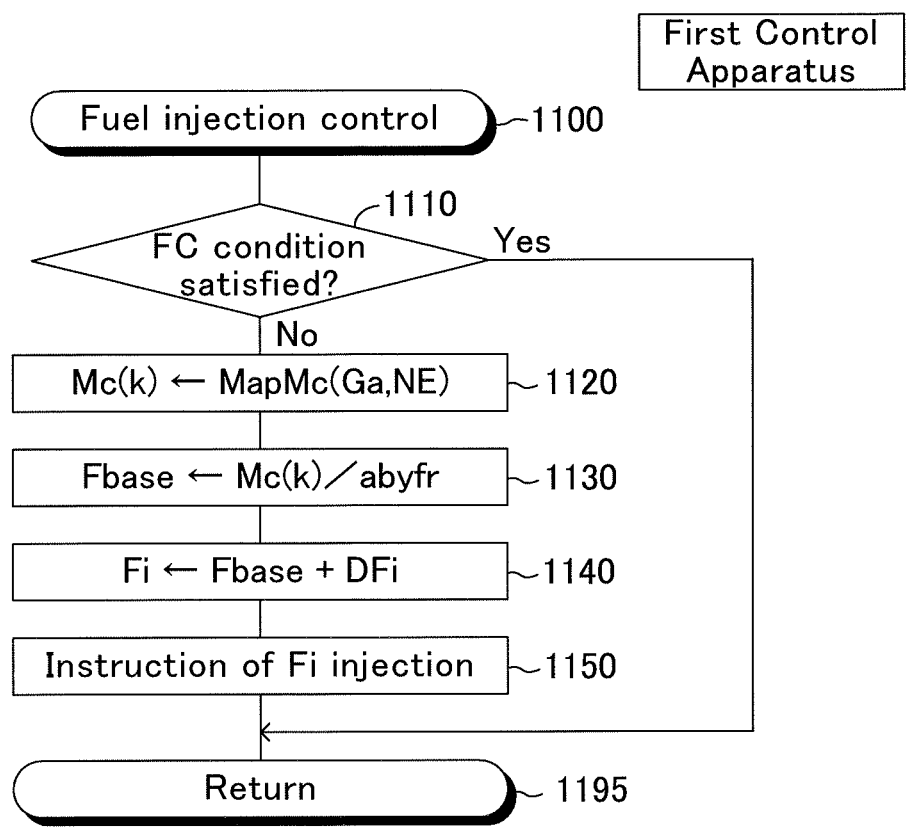
FIG. 11 is a flowchart showing a routine executed by a CPU of a fuel injection amount control apparatus (first control apparatus) according to a first embodiment of the present invention.

The CPU of the first control apparatus is designed to repeatedly execute a fuel injection control routine shown in FIG. 11 for an arbitrary cylinder, each time the crank angle of the arbitrary cylinder reaches a predetermined crank angle before the intake top dead center. The predetermined crank angle is, for example, BTDC 90° CA (90° crank angle before the intake top dead center). The cylinder whose crank angle becomes equal to the predetermined crank angle is also referred to as a "fuel injection cylinder." The CPU calculates the instructed fuel injection amount Fi, and instructs the fuel injection, by the fuel injection control routine.

When the crank angle of the arbitrary cylinder becomes equal to the predetermined crank angle, the CPU starts processing from step 1100 to proceed to step 1110, at which it determines whether or not a fuel cut condition (hereinafter, expressed as a "FC condition") is satisfied.

It is assumed here that the FC condition is not satisfied. Under this assumption, the CPU sequentially executes processes of step 1120 to step 1150 one after another, and proceeds to step 1195 to end the present routine tentatively.

Step 1120: The CPU obtains an "in-cylinder intake air amount Mc(k)" which is an "amount of an air introduced into the fuel injection cylinder in one intake stroke of the fuel injection cylinder", on the basis of the "intake air flow rate Ga measured by the air-flow meter 51, the engine rotational speed NE obtained based on the signal from the crank position sensor 54, and a look-up table MapMc." The in-cylinder intake air amount Mc(k) is stored in the RAM, while being related to the intake stroke of each cylinder. The in-cylinder intake air amount Mc(k) may be calculated based on a well-known air model (model constructed according to laws of physics describing and simulating a behavior of an air in the intake passage).

Step 1130: The CPU obtains a base fuel injection amount Fbase by dividing the in-cylinder intake air amount Mc(k) by the target air-fuel ratio abyfr. The target air-fuel ratio abyfr has been set at a predetermined base air-fuel ratio which is within the window of the catalyst 43. The base air-fuel ratio may be changed to a value in the vicinity of the stoichiometric air-fuel ratio, based on the intake air amount Ga, the degree of the deterioration of the catalyst 43, and so on. In the present example, the target air-fuel ratio abyfr is set at the stoichiometric air-fuel ratio stoich. Accordingly, the base fuel injection amount Fbase is a feedforward amount of the fuel injection amount nominally (based on calculation) required to realize/attain the stoichiometric air-fuel ratio stoich. This step 1130 constitutes a feedforward control section (base fuel injection amount calculation section) to have the air-fuel ratio of the mixture supplied to the engine coincide with the target air-fuel ratio abyfr.

Step 1140: The CPU corrects the base fuel injection amount Fbase with a main feedback amount DFi. More specifically, the CPU calculates the instructed fuel injection amount (final fuel injection amount) Fi by adding the main feedback amount DFi to the base fuel injection amount Fbase. The main feedback amount DFi is an air-fuel ratio feedback amount to have the air-fuel ratio of the engine coincide with the target air-fuel ratio abyfr, and is obtained based on an actual detected air-fuel ratio abyfsact into which the output value Vabyfs of the upstream air-fuel ratio sensor 56 is converted. The way to obtain the actual detected air-fuel ratio abyfsact and to calculate the main feedback amount DFi will be described later.

Step 1150: The CPU sends the injection instruction signal to the "fuel injection valve 33 corresponding to the fuel injection cylinder" so as to have the fuel injection valve 33 inject a "fuel of the instructed fuel injection amount Fi."

Consequently, the fuel is injected from the fuel injection valve 33, the amount of the injected fuel being an amount required (or estimated to be required) to have the air-fuel ratio of the engine become equal to the target air-fuel ratio abyfr. That is, the steps from step 1120 to step 1150 constitutes an instructed fuel injection amount control section to control the instructed fuel injection amount Fi in such a manner that the "air-fuel ratio of the mixture supplied to the combustion chambers 21 of a plurality of the cylinders (two or more of the cylinders, all of the cylinders in the present example) which discharge gases reaching the air-fuel ratio sensor 56" becomes equal to the target air-fuel ratio abyfr.

On the other hand, if the FC condition is satisfied when the CPU executes the process of step 1110, the CPU makes a "Yes" determination at step 1110 to directly proceed to step 1195, at which the CPU ends the present routine tentatively. In this case, since the fuel injection process of step 1150 is not executed, the fuel cut control (fuel supply stop control) is carried out.

<Obtainment of Air-Fuel Ratio>

Figure 12:
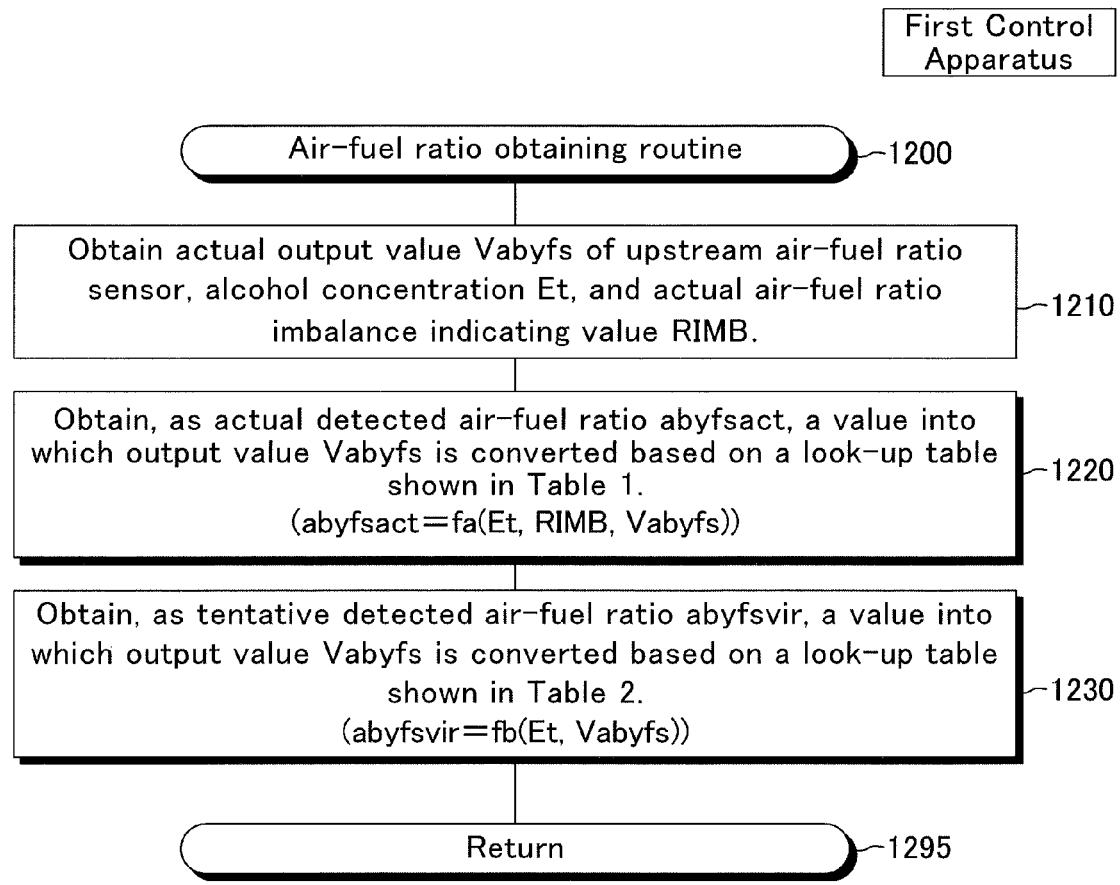
FIG. 12 is a flowchart showing a routine executed by the CPU of the first control apparatus.

The CPU repeatedly executes an "air-fuel ratio obtaining routine" shown by a flowchart in FIG. 12, every time a predetermined time period elapses. Accordingly, at an appropriate timing, the CPU starts the process from step 1200 to sequentially execute processes from step 1210 to step 1230 described below one after another, and then proceeds to step 1295 to end the present routine tentatively.

Step 1210: The CPU obtains the actual output value Vabyfs of the upstream air-fuel ratio sensor 56, the actual alcohol concentration Et which is the output value of the alcohol concentration sensor 59, and the actual air-fuel ratio imbalance indicating value RIMB which has been separately calculated in a routine described later. The actual air-fuel ratio imbalance indicating value RIMB is read out form the backup RAM.

Step 1220: The CPU obtains the actual detected air-fuel ratio abyfsact by applying "the actual alcohol concentration Et, the actual air-fuel ratio imbalance indicating value RIMB, and the actual output value Vabyfs" obtained at step 1210 to the look-up table shown in the Table 1.

The look-up table shown in the Table 1 is formed/generated based on data obtained in advance by the experiments, or the like, and defines the "relationship among the alcohol concentration Et, the air-fuel ratio imbalance indicating value RIMB, the output value Vabyfs of the air-fuel ratio sensor (upstream air-fuel ratio sensor 56), and the actual detected air-fuel ratio abyfsact which is the first air-fuel ratio correlated parameter correlated to the air-fuel ratio."

The relationship defined by the look-up table shown in the Table 1 is the above described first relationship. Accordingly, at step 1220, the CPU obtains the actual detected air-fuel ratio abyfsact (first air-fuel ratio correlated parameter), using the first relationship, based on "the actual alcohol concentration Et, the actual air-fuel ratio imbalance indicating value RIMB, and the actual output value Vabyfs." The first air-fuel ratio correlated parameter is a parameter used for the main feedback control.

Step 1230: The CPU obtains the "tentative detected air-fuel ratio abyfsvir (alcohol concentration corrected air-fuel ratio, second air-fuel ratio correlated parameter)" by applying "the alcohol concentration Et and the output value Vabyfs" that are obtained at step 1210 to the look-up table shown in the Table 2. The second air-fuel ratio correlated parameter is a parameter for obtaining the air-fuel ratio imbalance indicating value RIMB.

The look-up table shown in the Table 2 is formed/generated based on data obtained in advance by the experiments, or the like, and defines the "relationship among the alcohol concentration Et, the output value Vabyfs, and the tentative detected air-fuel ratio abyfsvir which is the second air-fuel ratio correlated parameter correlated to the air-fuel ratio", in a case in which the non-uniformity among the cylinder-by-cylinder air-fuel ratios is not occurring (i.e., when the air-fuel ratio imbalance indicating value RIMB is equal to "0").

The relationship defined by the look-up table shown in the Table 2 is the above described second relationship. Accordingly, at step 1230, the CPU obtains the tentative detected air-fuel ratio abyfsvir (second air-fuel ratio correlated parameter), using the second relationship, based on "the actual alcohol concentration Et, and the actual output value Vabyfs."

<Calculation of the Main Feedback Amount>

Figure 13:
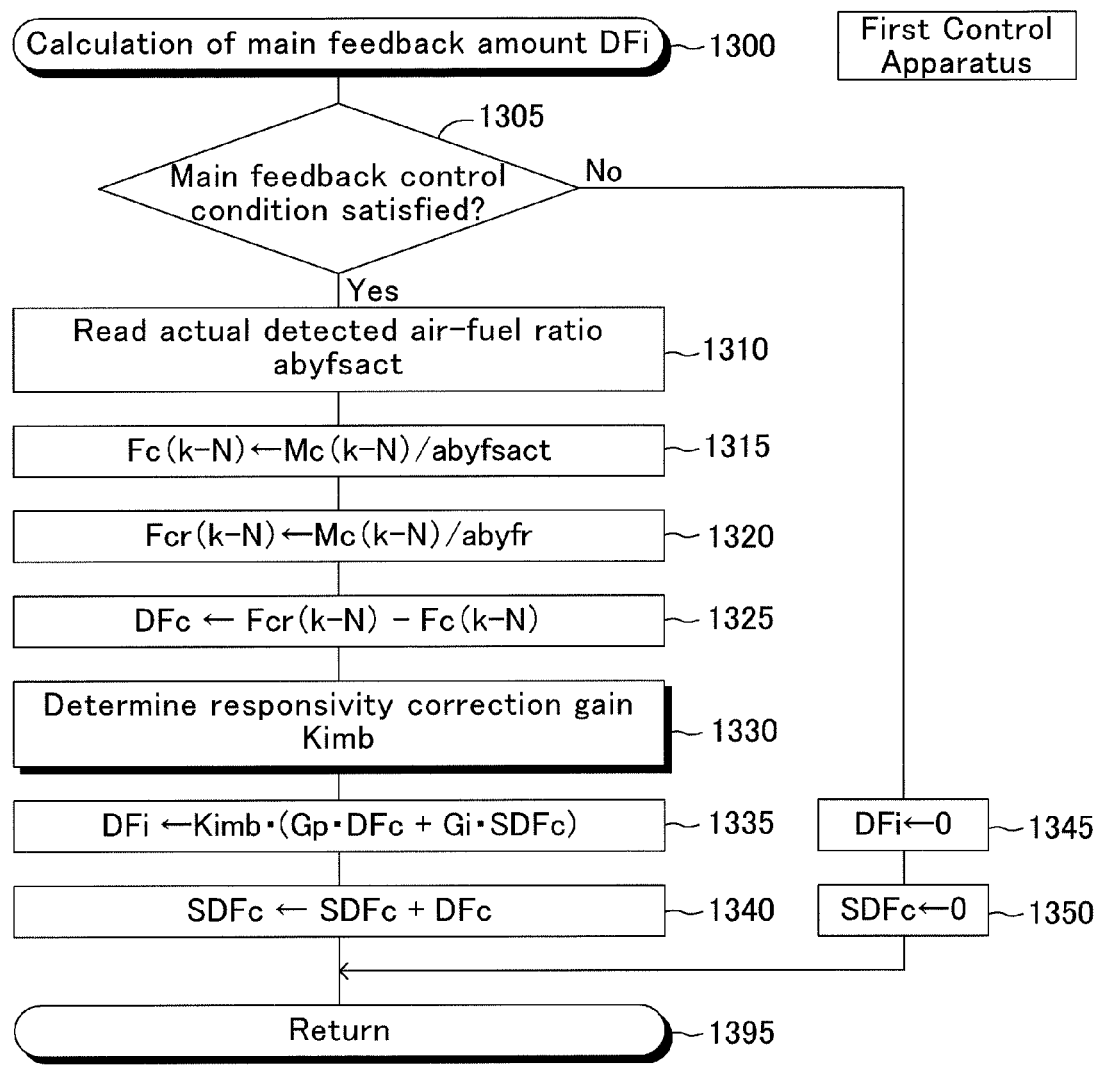
FIG. 13 is a flowchart showing a routine executed by the CPU of the first control apparatus.

The CPU repeatedly executes a "routine for the calculation of the main feedback amount" shown by a flowchart in FIG. 13, every time a predetermined time period elapses. Accordingly, at an appropriate timing, the CPU starts the process from step 1300 to proceed to step 1305, at which the CPU determines whether or not a "main feedback control condition (upstream air-fuel ratio feedback control condition)" is satisfied.

The main feedback control condition is satisfied when all of the following conditions are satisfied.
(A1) The upstream air-fuel ratio sensor 56 has been activated.
(A2) The load KL of the engine is smaller than or equal to a threshold value KLth.
(A3) The fuel cut control is not being performed.

It should be noted that the load KL is a load rate obtained based on the following formula (1). The accelerator pedal operation amount Accp can be used in place of the load rate KL. In the formula (1), Mc is the in-cylinder intake air amount, ρ is an air density (unit is (g/l), L is a displacement of the engine 10 (unit is (l)), and "4" is the number of cylinders of the engine 10.

$$KL=(Mc/(\rho \cdot L/4)) \cdot 100\% \qquad (1)$$

The description continues assuming that the main feedback control condition is satisfied. In this case, the CPU makes a "Yes" determination at step 1305 to sequentially execute processes from step 1310 to step 1340 described below one after another, and then proceeds to step 1395 to end the present routine tentatively.

Step 1310: The CPU reads out the actual detected air-fuel ratio abyfsact (first air-fuel ratio correlated parameter) which has been obtained by the air-fuel ratio obtaining routine shown in FIG. 12.

Step 1315: According to a formula (2) described below, the CPU obtains an "in-cylinder fuel supply amount Fc(k−N)" which is an "amount of the fuel actually supplied to the combustion chamber 21 for a cycle at a timing N cycles before the present time." That is, the CPU obtains the in-cylinder fuel supply amount Fc(k−N) through dividing the "in-cylinder intake air amount Mc(k−N) which is the in-cylinder intake air amount for the cycle the N cycles (i.e., N·720° crank angle) before the present time" by the "actual detected air-fuel ratio abyfsact."

$$Fc(k-N)=Mc(k-N)/abyfsact \qquad (2)$$

The reason why the cylinder intake air amount Mc(k−N) for the cycle N cycles before the present time is divided by the actual detected air-fuel ratio abyfsact in order to obtain the in-cylinder fuel supply amount Fc(k−N) is because the "exhaust gas generated by the combustion of the mixture in the combustion chamber 21" requires time "corresponding to the N cycles" to reach the air-fuel ratio sensor 56.

Step 1320: The CPU obtains a "target in-cylinder fuel supply amount Fcr(k−N)" which is an "amount of the fuel supposed to be supplied to the combustion chamber 21 for the cycle the N cycles before the present time", according to a formula (3) described below. That is, the CPU obtains the target in-cylinder fuel supply amount Fcr(k−N) by dividing the in-cylinder intake air amount Mc(k−N) for the cycle the N cycles before the present time by the target air-fuel ratio abyfr.

$$Fcr=Mc(k-N)/abyfr \qquad (3)$$

Step 1325: The CPU obtains an "error DFc of the in-cylinder fuel supply amount", according to a formula (4) described below. That is, the CPU obtains the error DFc of the in-cylinder fuel supply amount by subtracting the in-cylinder fuel supply amount Fc(k−N) from the target cylinder fuel supply amount Fcr(k−N). The error DFc of the in-cylinder fuel supply amount represents excess and deficiency of the fuel supplied to the cylinder for the cycle the N cycles before the present time. The error DFc of the in-cylinder fuel supply amount is one of values which corresponds to (is correlated to) a difference between the actual detected air-fuel ratio abyfsact and the target air-fuel ratio abyfr.

$$DFc=Fcr(k-N)-Fc(k-N) \qquad (4)$$

Step 1330: The CPU determines a responsivity correction gain Kimb by executing a routine shown in FIG. 14. The routine shown in FIG. 14 will be described later.

The responsivity correction gain Kimb is calculated "so as to increase within a range larger than a base gain Kbase (in the present example, "1") as the air-fuel ratio imbalance indicating value RIMB becomes larger, and so as to increase within the range larger than the base gain Kbase as the alcohol concentration Et becomes higher" in a predetermined period from a point in time at which the actual detected air-fuel ratio abyfsact changed to an "air-fuel ratio leaner than the stoichiometric air-fuel ratio stoich" from an "air-fuel ratio richer than the stoichiometric air-fuel ratio stoich" and when the actual detected air-fuel ratio abyfsact is still the "air-fuel ratio leaner than the stoichiometric air-fuel ratio stoich."

The responsivity correction gain Kimb is set to (at) the base gain Kbase (in the present example, "1"), in a period which is not the predetermined period from the point in time at which the actual detected air-fuel ratio abyfsact changed to the "air-fuel ratio leaner than the stoichiometric air-fuel ratio stoich" from the "air-fuel ratio richer than the stoichiometric air-fuel ratio stoich", or when the actual detected air-fuel ratio abyfsact is the "air-fuel ratio richer than the stoichiometric air-fuel ratio stoich."

The actual detected air-fuel ratio abyfsact is calculated so as to coincide with the "true air-fuel ratio of the exhaust gas" by the air-fuel ratio obtaining routine shown in FIG. 12. However, in a case in which the non-uniformity among the cylinder-by-cylinder air-fuel ratios is occurring, or in a case in which the alcohol concentration is not "0", a change rate of the output value Vabyfs (post rich-lean inversion responsivity) when the true air-fuel ratio of the exhaust gas has changed to the "air-fuel ratio leaner than the stoichiometric air-fuel ratio stoich" from the "air-fuel ratio richer than the stoichiometric air-fuel ratio stoich" (i.e., rich-lean inversion time point) is smaller than a change rate of the output value Vabyfs (post lean-rich inversion responsivity) when the true air-fuel ratio of the exhaust gas has changed to the "air-fuel ratio richer than the stoichiometric air-fuel ratio stoich" from the "air-fuel ratio leaner than the stoichiometric air-fuel ratio stoich" (i.e., lean-rich inversion time point). This is because, the output value Vabyfs is affected by hydrogen which is produced in a great amount due to "the occurrence of the non-uniformity among cylinder-by-cylinder air-fuel ratios, or the inclusion of the alcohol in the fuel."

In other words, even in a case in which the true air-fuel ratio of the exhaust gas is in the vicinity of the stoichiometric air-fuel ratio, since a "larger amount of hydrogen" is present in the vicinity of the upstream air-fuel ratio sensor 56 as the degree of the non-uniformity among the cylinder-by-cylinder air-fuel ratios becomes larger, or as the alcohol concentration Et becomes higher, the output value Vabyfs rapidly decreases due to the presence of the great amount of hydrogen upon the lean-rich inversion time point, and the output value Vabyfs gradually increases due to the presence of the great amount of hydrogen upon the rich-lean inversion time point. The responsivity correction gain Kimb is a gain to compensate for such an asymmetric responsivity of the output value Vabyfs.

Step 1335: The CPU obtains the main feedback amount DFi, according to a formula (5) described below. In the formula (5) below, Gp is a predetermined proportion gain, and Gi is a predetermined integration gain. Further, the "value SDFc" in the formula (5) is an "integrated value of the error DFc of the in-cylinder fuel supply amount." The value SDFc is one of the values, each being correlated to the difference between the actual detected air-fuel ratio abyfsact and the target air-fuel ratio abyfr. Therefore, the value (Gp·DFc+Gi·SDFc) is one of the values, each being correlated to the difference between the actual detected air-fuel ratio abyfsact and the target air-fuel ratio abyfr. In this manner, the CPU calculates the "main feedback amount DFi" based on a proportional-integral control to have the actual detected air-fuel ratio abyfsact coincide with the target air-fuel ratio abyfr.

$$DFi = Kimb \cdot (Gp \cdot DFc + Gi \cdot SDFc) \quad (5)$$

Step 1340: The CPU obtains a new integrated value SDFc of the error of the in-cylinder fuel supply amount by adding the error DFc of the in-cylinder fuel supply amount obtained at step 1325 described above to the current/present integrated value SDFc of the error of the in-cylinder fuel supply amount.

As described above, the main feedback amount DFi is obtained based on the proportional-integral control. The main feedback amount DFi is reflected in (onto) the instructed fuel injection amount Fi by the process of step 1140 shown in FIG. 11.

To the contrary, if the main feedback control condition is not satisfied at the time of determination at step 1305 shown in FIG. 13, the CPU makes a "No" determination at step 1305 so as to proceed to step 1345 to set the value of the main feedback amount DFi to (at) "0." Subsequently, the CPU stores "0" into the integrated value SDFc of the error of the in-cylinder fuel supply amount at step 1350. Thereafter, the CPU proceeds to step 1395 to end the present routine tentatively. As described above, when the main feedback control condition is not satisfied, the main feedback amount DFi is set to (at) "0." Accordingly, the correction on the base fuel injection amount Fbase with the main feedback amount DFi is not performed.

<Calculation of the Responsivity Correction Gain Kimb>

Figure 14:
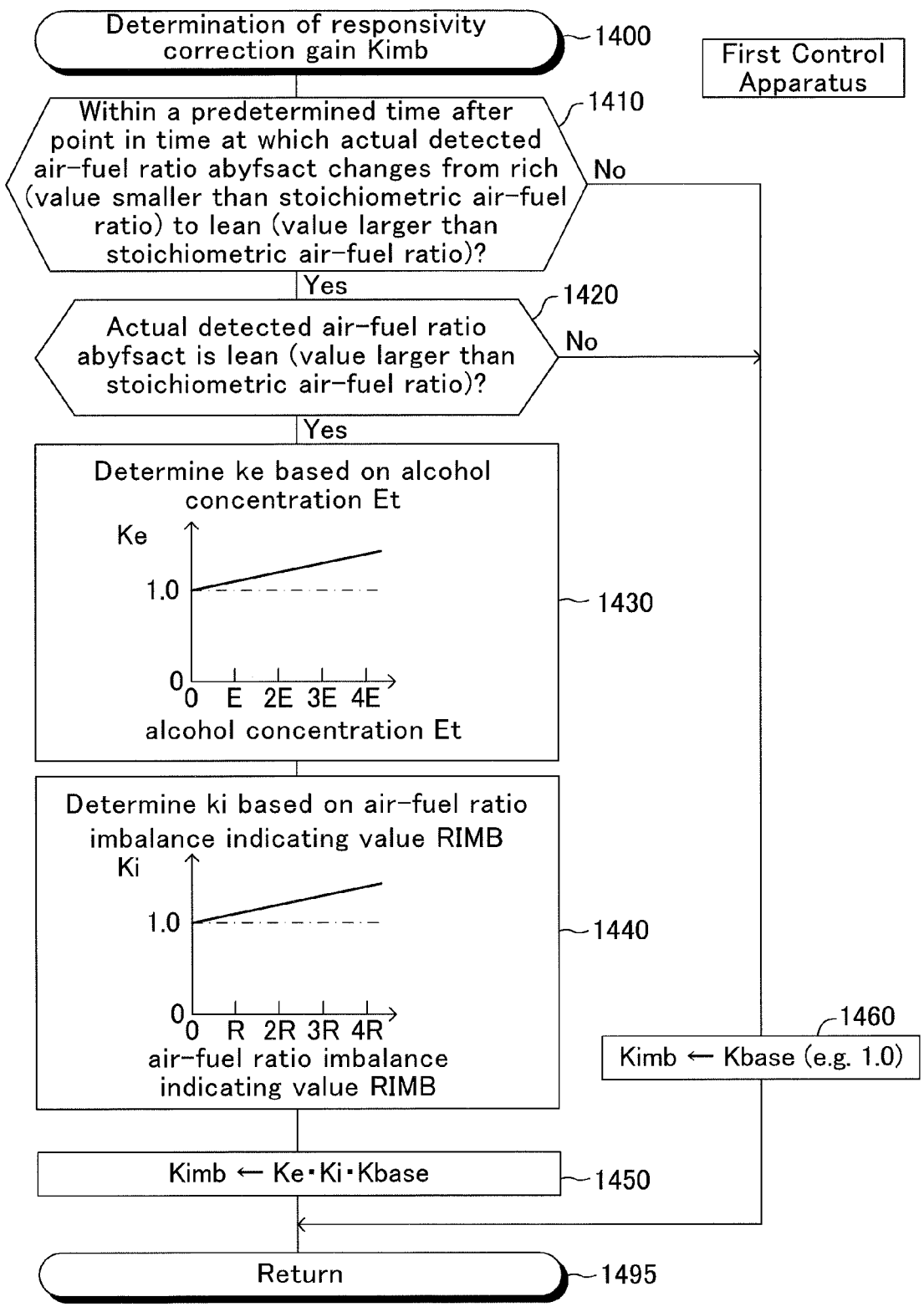
FIG. 14 is a flowchart showing a routine executed by the CPU of the first control apparatus.

As described above, when the CPU proceeds to step 1330 shown in FIG. 13, the CPU executes the processes of the responsivity correction gain Kimb calculation routine shown in FIG. 14. That is, when the CPU proceeds to step 1330 shown in FIG. 13, the CPU proceeds to step 1400 shown in FIG. 14. At next step 1410, the CPU determines whether the present point in time is within the predetermined time from the time point (rich-lean inversion time point) at which the actual detected air-fuel ratio abyfsact has changed to the air-fuel ratio leaner than the stoichiometric air-fuel ratio stoich from the air-fuel ratio richer than the stoichiometric air-fuel ratio stoich.

When the present point in time is within the predetermined time from the rich-lean inversion time point, the CPU makes a "Yes" determination at step 1410 to proceed to step 1420, at which the CPU determines whether or not the actual detected air-fuel ratio abyfsact is leaner than the stoichiometric air-fuel ratio stoich.

When the actual detected air-fuel ratio abyfsact is still leaner than the stoichiometric air-fuel ratio stoich, the CPU sequentially executes processes from step 1430 to step 1450, described below, one after another. Thereafter, the CPU proceeds to step 1335 shown in FIG. 13 via step 1495.

Step 1430: The CPU determines a coefficient ke in such a manner that the coefficient ke becomes larger within a range larger than "1", as the actual alcohol concentration Et becomes higher.

Step 1440: The CPU determines a coefficient ki in such a manner that the coefficient ki becomes larger within a range larger than "1", as the air-fuel ratio imbalance indicating value RIMB becomes larger.

Step 1450: The CPU calculates the responsivity correction gain Kimb by multiplying a base gain Kbase by a "product of the coefficient ke and the coefficient ki." The base gain Kbase is a constant value, and is set at "1" in the present example. Consequently, the responsivity correction gain Kimb is determined as a value, which becomes larger within a range larger than the base gain Kbase as the actual alcohol concentration Et becomes higher, and which becomes larger within the range larger than the base gain Kbase as the air-fuel ratio imbalance indicating value RIMB becomes larger.

In contrast, when the present point in time is not within the predetermined time from the rich-lean inversion time point, the CPU makes a "No" determination at step 1410 to proceed to step 1460, at which the CPU sets the value of the responsivity correction gain Kimb to the base gain Kbase. Thereafter, the CPU proceeds to step 1335 shown in FIG. 13 via step 1495.

Further, if the actual detected air-fuel ratio abyfsact has already changed to an air-fuel ratio richer than the stoichiometric air-fuel ratio stoich even when the present point in time is within the predetermined time from the rich-lean inversion time point, the CPU makes a "No" determination at step 1420 to proceed to step 1460, at which the CPU sets the value of the responsivity correction gain Kimb to the base gain Kbase. Thereafter, the CPU proceeds to step 1335 shown in FIG. 13 via step 1495.

<Obtaining the Air-Fuel Ratio Imbalance Indicating Value, and Determining the Inter-Cylinder Air-Fuel Ratio Imbalance>

Next will be described processes for performing the "air-fuel ratio imbalance indicating value obtainment and inter-cylinder air-fuel ratio imbalance determination." The CPU is configured so as to execute a routine shown by a flowchart in FIG. 15 every elapse of 4 ms (a predetermined constant sampling time ts).

Accordingly, at an appropriate timing, the CPU starts process from step 1500 to proceed to step 1505, at which the CPU determines whether or not a value of a parameter obtaining permission flag Xkyoka is "1."

The value of the parameter obtaining permission flag Xkyoka is set to (at) "1," if a parameter obtaining condition described later is satisfied when the absolute crank angle CA coincides with 0° crank angle, and is set to (at) "0" immediately after the parameter obtaining condition becomes unsatisfied.

The parameter obtaining condition is satisfied when all of conditions (conditions C1 to C5) described below are satisfied. In other words, the parameter obtaining condition is not satisfied when at least any one of the following conditions (conditions C1 to C5) is unsatisfied. It should be noted that conditions for the parameter obtaining condition are not limited to the following conditions C1 to C5.

(Condition C1)

The intake air flow rate Ga obtained from the air-flow meter 51 is within a predetermined range. That is, the intake air flow rate Ga is larger than or equal to a low side intake air flow rate threshold GaLoth, and is smaller than or equal to a high side intake air flow rate threshold GaHith. Owing to this condition C1, a "degradation of an accuracy of the air-fuel ratio imbalance indicating value RIMB" due to a change in the responsivity of the output value Vabyfs caused by the intake air flow rate Ga can be avoided.

(Condition C2)

The engine rotational speed NE is within a predetermined range. That is, the engine rotational speed NE is larger than or equal to a low side engine rotational speed threshold NELoth, and is smaller than or equal to a high side engine rotational speed NE threshold NEHith.

(Condition C3)

The cooling water temperature THW is higher than or equal to a cooling water temperature threshold THWth.

(Condition C4)

The main feedback control condition is satisfied.

(Condition C5)

The fuel cut control is not being performed.

Here, it is assumed that the value of the parameter obtaining permission flag Xkyoka is "1." In this case, the CPU makes a "Yes" determination at step 1505 to proceed to step 1510, at which the CPU reads out the tentative detected air-fuel ratio abyfsvir (second air-fuel ratio correlated parameter) which has been calculated by the air-fuel ratio obtaining routine shown in FIG. 12.

It should be noted that the CPU stores the tentative detected air-fuel ratio abyfsvir which was obtained in the previous execution of the present routine as a previous tentative detected air-fuel ratio abyfsvirold, before executing the process of the step 1510. That is, the previous tentative detected air-fuel ratio abyfsvirold is the tentative detected air-fuel ratio abyfsvir 4 ms (the sampling time ts) before the present time. An initial value of the previous tentative detected air-fuel ratio abyfsvirold is set at a value corresponding to the stoichiometric air-fuel ratio in an initial routine which is executed when the engine 10 is started.

Subsequently, the CPU proceeds to step 1520, at which the CPU, (A) obtains the detected air-fuel ratio changing rate $\Delta AF$, (B) renews a cumulated value SAFD of an absolute value $|\Delta AF|$ of the detected air-fuel ratio changing rate $\Delta AF$, and (C) renews a cumulated number counter Cn showing how many times the absolute value $|\Delta AF|$ of the detected air-fuel ratio changing rate $\Delta AF$ is accumulated (integrated) to the cumulated value SAFD.

The ways in which these values are renewed will next be described more specifically.

(A) Obtainment of the Detected Air-Fuel Ratio Changing Rate $\Delta AF$:

The detected air-fuel ratio changing rate $\Delta AF$ (differential value d(abyfsvir)/dt) is a base data (base indicating amount) for the air-fuel ratio imbalance indicating value RIMB. The CPU obtains the detected air-fuel ratio changing rate $\Delta AF$ by subtracting the previous tentative detected air-fuel ratio abyfsvirold from the present tentative detected air-fuel ratio abyfsvir. That is, when the present tentative detected air-fuel ratio abyfsvir is expressed as abyfsvir(n), and the previous tentative detected air-fuel ratio abyfsvirold is expressed as abyfsvir(n-1), the CPU obtains the "present detected air-fuel ratio changing rate $\Delta AF(n)$" at step 1520 according to a formula (6) described below.

$$\Delta AF(n) = abyfsvir(n) - abyfsvir(n-1) \qquad (6)$$

(B) Renewal of the Cumulated Value SAFD of the Absolute Value $|\Delta AF|$ of the Detected Air-Fuel Ratio Changing Rate $\Delta AF$:

The CPU obtains the present cumulated value SAFD(n) according to a formula (7) described below. That is, the CPU updates the cumulated value SAFD by adding the absolute value $|\Delta AF(n)|$ of the presently detected air-fuel ratio changing rate $\Delta AF(n)$ obtained as described above to the previous cumulated value SAFD(n-1) when the CPU proceeds to step 1520.

$$SAFD(n) = SAFD(n-1) + |\Delta AF(n)| \qquad (7)$$

The reason why the "absolute value $|\Delta AF(n)|$ of the presently detected air-fuel ratio changing rate" is added to the cumulated value SAFD is that the detected air-fuel ratio changing rate $\Delta AF(n)$ can become both a positive value and a negative value, as understood from (B) and (C) in FIG. 9. It should be noted that the cumulated value SAFD is set to (at) "0" in the initial routine described above.

(C) Renewal of the Cumulated Number Counter Cn Showing how Many Times the Absolute Value $|\Delta AF|$ of the Detected Air-Fuel Ratio Changing Rate $\Delta AF$ is accumulated to the cumulated value SAFD:

The CPU increments a value of the counter Cn by "1" according to a formula (8) described below. Cn(n) represents the counter Cn after the renewal, and Cn(n-1) represents the counter Cn before the renewal. The value of the counter Cn is set at "0" in the initial routine described above, and is also set to (at) "0" at step 1560 and step 1565, described later. The value of the counter Cn therefore represents the number of data of the absolute value $|\Delta AF|$ of the detected air-fuel ratio changing rate ΔAF which has been accumulated in the cumulated value SAFD.

$$Cn(n)=Cn(n-1)+1 \qquad (8)$$

Subsequently, the CPU proceeds to step 1525 to determine whether or not the crank angle CA (absolute crank angle CA) measured with reference to the top dead center of the compression stroke of the reference cylinder (in the present example, the first cylinder) reaches 720° crank angle. When the absolute crank angle CA is less than 720° crank angle, the CPU makes a "No" determination at step 1525 to directly proceed to step 1595, at which the CPU ends the present routine tentatively.

It should be noted that step 1525 is a step to define the smallest unit period for obtaining an average of the absolute values |ΔAF| of the detected air-fuel ratio changing rate ΔAF. Here, the "720° crank angle which is the unit combustion cycle period" corresponds to the smallest unit period. The smallest unit period may obviously be shorter than the 720° crank angle, however, may preferably be a time period longer than or equal to a period having an integral multiple of the sampling time ts. Further, it is preferable that the smallest unit period be the time period having an integral (natural number) multiple of the unit combustion cycle period.

Meanwhile, if the absolute crank angle CA reaches 720° crank angle when the CPU executes the process of step 1525, the CPU makes a "Yes" determination at step 1525 to proceed to step 1530.

The CPU, at step 1530:
(D) calculates an average value AveΔAF of the absolute values |ΔAF| of the detected air-fuel ratio changing rates ΔAF,
(E) renews a cumulated value Save of the average value AveΔAF, and
(F) renews a cumulated number counter Cs.

The ways in which these values are renewed will next be described more specifically.
(D) Calculation of the Average Value AveΔAF of the Absolute Values |ΔAF| of the Detected Air-Fuel Ratio Changing Rates ΔAF:

The CPU calculates the average value AveΔAF of the absolute values |ΔAF| of the detected air-fuel ratio changing rates ΔAF through dividing the cumulated value SAFD by a value of the counter Cn, according to a formula (9) described below. Thereafter, the CPU sets both the cumulated value SAFD and the value of the counter Cn to (at) "0."

$$Ave\Delta AF=SAFD/Cn \qquad (9)$$

(E) Renewal of the Cumulated Value Save of the Average Value AveΔAF:

The CPU obtains the present cumulated value Save(n) according to a formula (10) described below. That is, the CPU renews the cumulated value Save by adding the present average value AveΔAF obtained as described above to the previous cumulated value Save(n-1) when the CPU proceeds to step 1530. The value of the cumulated value Save(n) is set to (at) "0" in the initial routine described above as well as at step 1560 described later.

$$Save(n)=Save(n-1)+Ave\Delta AF \qquad (10)$$

(F) Renewal of the Cumulated Number Counter Cs:

The CPU increments a value of the counter Cs by "1" according to a formula (11) described below. Cs(n) represents the counter Cs after the renewal, and Cs(n-1) represents the counter Cs before the renewal. The value of the counter Cs is set to (at) "0" in the initial routine described above as well as at step 1560 described later. The value of the counter Cs therefore represents the number of data of the average value AveΔAF which has been accumulated in the cumulated value Save.

$$Cs(n)=Cs(n-1)+1 \qquad (11)$$

Subsequently, the CPU proceeds to step 1535 to determine whether or not the value of the counter Cs is larger than or equal to a threshold value Csth. When the value of the counter Cs is less than the threshold value Csth, the CPU makes a "No" determination at step 1535 to directly proceed to step 1595, at which the CPU ends the present routine tentatively. It should be noted that the threshold value Csth is a natural number, and is preferably larger than or equal to 2.

Meanwhile, if the value of the counter Cs is larger than or equal to the threshold value Csth when the CPU executes the process of step 1535, the CPU makes a "Yes" determination at step 1535 to proceed to step 1540. At step 1540, the CPU obtains the air-fuel ratio imbalance indicating value RIMB (=air-fuel ratio fluctuation indicating amount AFD) through dividing the cumulated value Save by the value of the counter Cs (=Csth), according to a formula (12) described below. The air-fuel ratio imbalance indicating value RIMB is a value obtained by averaging the average values AveΔAF, each of which is the average of the absolute values |ΔAF| of the detected air-fuel ratio changing rates ΔAF for each combustion cycle period, over a plurality (Csth) of the unit combustion cycle periods. The air-fuel ratio imbalance indicating value RIMB is stored in the back up RAM as a learning value.

$$RIMB=AFD=Save/Csth \qquad (12)$$

It should be noted that the CPU may obtain a weighted average by applying the learning value RIMBgaku (=RIMBgaku(n-1)) which has been stored in the backup RAM and the presently obtained air-fuel ratio imbalance indicating value RIMB to a formula (13) described below, and store the weighted average RIMBgaku(n) in the backup RAM as a new learning value RIMBgaku. In the formula (13), β is a predetermined value which is larger than 0 and smaller than 1.

$$RIMBgaku(n)=\beta \cdot RIMBgaku(n-1)+(1-\beta) \cdot RIMB \qquad (13)$$

Subsequently, the CPU proceeds to step 1545 to determine whether or not the air-fuel ratio imbalance indicating value RIMB is larger than the imbalance determination threshold RIMBth. That is, the CPU determines whether or not the inter-cylinder air-fuel ratio imbalance state has occurred at step 1545.

When the air-fuel ratio imbalance indicating value RIMB is larger than the imbalance determination threshold RIMBth, the CPU makes a "Yes" determination at step 1545 to proceed to step 1550, at which the CPU sets a value of an imbalance occurrence flag XIMB to "1." That is, the CPU determines that the inter-cylinder air-fuel-ratio imbalance state has occurred. Furthermore, the CPU may turn on a warning lamp which is not shown. It should be noted that the value of the imbalance occurrence flag XIMB is stored in the backup RAM. Subsequently, the CPU proceeds to step 1560.

In contrast, if the air-fuel ratio imbalance indicating value RIMB is smaller than the imbalance determination threshold RIMBth when the CPU executes the process of step 1545, the CPU makes a "No" determination at step 1545 to proceed to step 1555, at which the CPU sets the value of the imbalance occurrence flag XIMB to "2." That is, the CPU memorizes the "fact that it has been determined that the inter-cylinder air-fuel-ratio imbalance state has not occurred as a result of the inter-cylinder air-fuel-ratio imbalance determination." Subsequently, the CPU proceeds to step 1560.

Subsequently, the CPU proceeds to step 1560 to set (or clear) "each of the values (e.g., ΔAF, SAFD, Cn, AveΔAF, Save, Cs, and so on) used for the calculation of the air-fuel ratio imbalance indicating value RIMB" to (at) "0". Thereafter, the CPU proceeds to step 1595 to end the present routine tentatively.

If the value of the parameter obtaining permission flag Xkyoka is not "1" when the CPU proceeds to step 1505, the CPU makes a "No" determination at step 1505 to proceed to step 1565. At step 1565, the CPU sets (or clears) "each of the values (e.g., ΔAF, SAFD, Cn, and so on) used for the calculation of the average value AveΔAF" to (at) "0". Thereafter, the CPU proceeds to step 1595 to end the present routine tentatively.

As described above, the first control apparatus comprises:
a first air-fuel ratio correlated parameter obtaining section (step 1220 shown in FIG. 12) which is configured so as to convert the output value Vabyfs of the air-fuel ratio sensor 56 into the actual first air-fuel ratio correlated parameter (actual detected air-fuel ratio abyfsact) based on the actual alcohol concentration Et and the actual air-fuel ratio imbalance indicating value RIMB, using the predetermined first relationship (refer to the look-up table shown in the Table 1) among the output value of the air-fuel ratio sensor 56, the alcohol concentration, the air-fuel ratio imbalance indicating value, and the first air-fuel ratio correlated parameter (actual detected air-fuel ratio abyfsact) correlated to the true air-fuel ratio of the exhaust gas;

an instructed fuel injection amount determining section (step 1140 shown in FIG. 11 and the routine shown in FIG. 13) which is configured so as to determine the instructed fuel injection amount Fi which is the instruction value of the amount of the fuel to be injected from each of a plurality of the fuel injection valves 33, by performing the feedback correction on the amount of the fuel to be injected from each of the fuel injection valves 33 in such a manner that the obtained actual first air-fuel ratio correlated parameter (actual detected air-fuel ratio abyfsact) coincides with the predetermined target value (target air-fuel ratio abyfr); and an injection instruction signal supplying section (step 1150 shown in FIG. 11) which is configured so as to send (supply) the injection instruction signal to a plurality of the fuel injection valves 33 in such a manner that the fuel of an amount corresponding to the instructed fuel injection amount Fi is injected from each of a plurality of the fuel injection valves 33.

Further, in the first control apparatus, the first air-fuel ratio correlated parameter obtaining section is configured so as to obtain, as the first air-fuel ratio correlated parameter, a value which is an air-fuel ratio, into which the actual output value of the air-fuel ratio sensor is converted using the first relationship, which becomes larger as the actual alcohol concentration becomes higher, and which becomes larger as the actual air-fuel ratio imbalance indicating value becomes larger (step 1220 shown in FIG. 12); and the instructed fuel injection amount determining section is configured so as to use, as the target value, the target air-fuel ratio abyfr which is set at the predetermined air-fuel ratio (predetermined base air-fuel ratio) which is within the window of the three way catalyst 43 (step 1130 shown in FIG. 11 and step 1320 shown in FIG. 13).

Further, the first air-fuel ratio correlated parameter obtaining section stores the first relationship in the form of the look-up table (table 1) or the function fa, which inputs the output value of the air-fuel ratio sensor, the alcohol concentration, and the air-fuel ratio imbalance indicating value, and outputs the first air-fuel ratio correlated parameter; and obtains the actual first air-fuel ratio correlated parameter (actual detected air-fuel ratio abyfsact) by inputting the actual output value Vabyfs of the air-fuel ratio sensor, the actual alcohol concentration Et, and the actual air-fuel ratio imbalance indicating value RIMB to the look-up table or the function (step 1220 shown in FIG. 12).

The thus obtained first air-fuel ratio correlated parameter (actual detected air-fuel ratio abyfsact) becomes a value corresponding to the true air-fuel ratio of the exhaust gas. Therefore, by means of the main feedback control to have the first air-fuel ratio correlated parameter (actual detected air-fuel ratio abyfsact) coincide with the target value (target air-fuel ratio abyfr), the true air-fuel ratio of the exhaust gas can be adjusted to be an air-fuel ratio corresponding to the target value. Consequently, the increase of the discharge amount of NOx and the like can be avoided, regardless of the degree of the non-uniformity among the cylinder-by-cylinder air-fuel ratios and the alcohol concentration.

Figure 15:
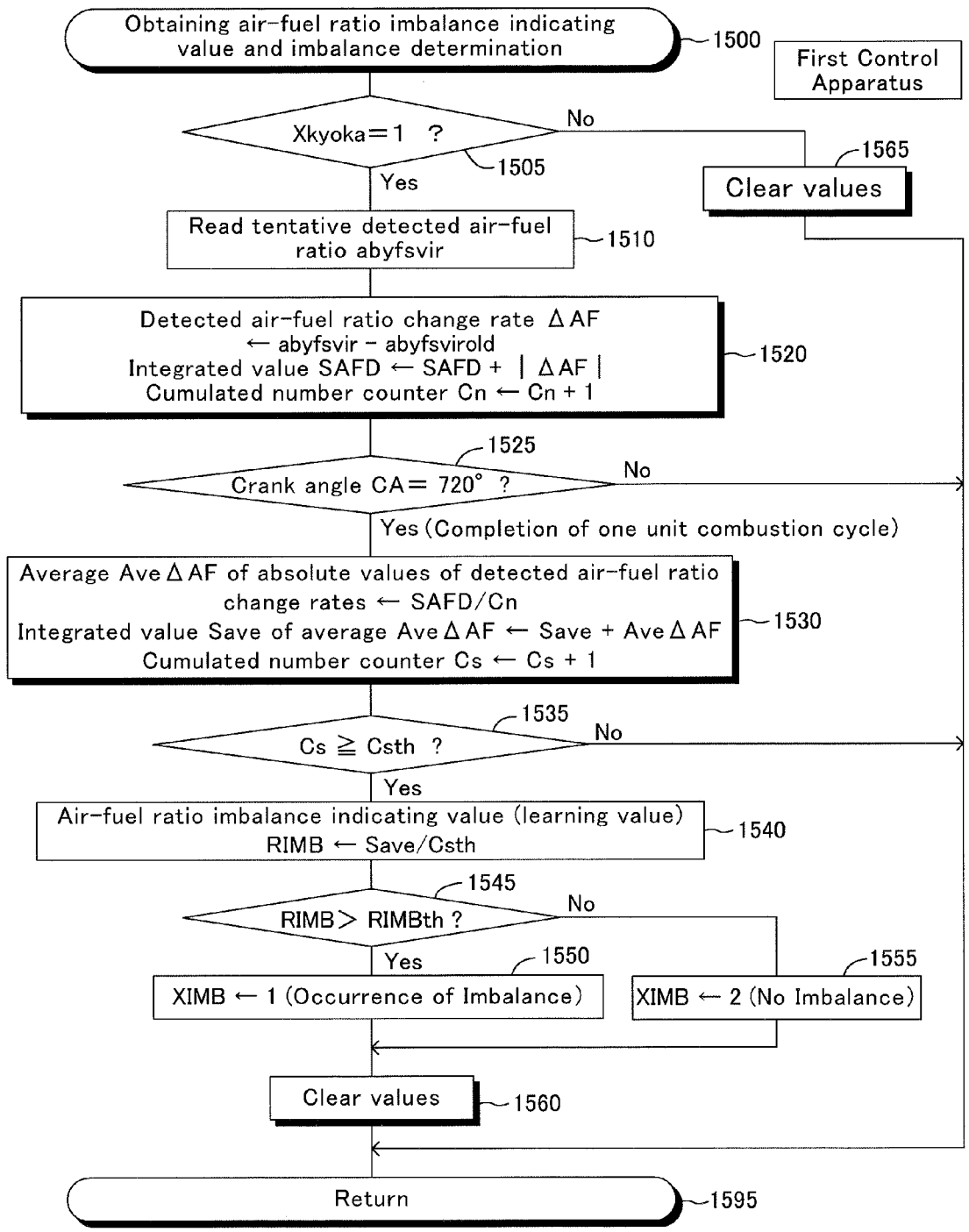
FIG. 15 is a flowchart showing a routine executed by the CPU of the first control apparatus.

In addition, the first control apparatus comprises an air-fuel ratio imbalance indicating value obtaining section configured so as to obtain, based on the "predetermined specific parameter", the air-fuel ratio imbalance indicating value which becomes larger as the degree of the non-uniformity of the cylinder-by-cylinder air-fuel ratio among a plurality of the cylinders becomes larger (the routine shown in FIG. 15).

The air-fuel ratio imbalance indicating value obtaining section is configured so as to:

convert the actual output value Vabyfs of the air-fuel ratio sensor 56 into the actual second air-fuel ratio correlated parameter (tentative detected air-fuel ratio abyfsvir) correlated to the true air-fuel ratio of the exhaust gas, based on the actual alcohol concentration Et, using the predetermined second relationship (refer to the table 2) among (between) the output value of the air-fuel ratio sensor, the alcohol concentration, and the second air-fuel ratio correlated parameter, in a case in which the non-uniformity of the cylinder-by-cylinder air-fuel ratio among a plurality of the cylinders does not occur (step 1230, shown in FIG. 12);

adopt, as the "specific parameter", the actual second air-fuel ratio correlated parameter (tentative detected air-fuel ratio abyfsvir); and obtain, as the air-fuel ratio imbalance indicating value RIMB, a value which becomes larger as a variation of the second air-fuel ratio correlated parameter (tentative detected air-fuel ratio abyfsvir) becomes larger (refer to the routine shown in FIG. 15).

Accordingly, the tentative detected air-fuel ratio abyfsvir which is base data for obtaining the air-fuel ratio imbalance indicating value RIMB is a value, which does not vary depending on the air-fuel ratio imbalance indicating value RIMB itself, and which is obtained by eliminating the effect on the output value Vabyfs which the alcohol concentration has. Consequently, it is possible to obtain the air-fuel ratio imbalance indicating value RIMB which represents the degree of the non-uniformity among the cylinder-by-cylinder air-fuel ratios with high accuracy.

Second Embodiment

Next, there will be described a control apparatus according to a second embodiment of the present invention (hereinafter, simply referred to as a "second control apparatus").

The limiting current IL of the limiting-current-type upstream air-fuel ratio sensor 56 changes as expressed by a formula (14) described below and a formula (15) described below.

A case in which the air-fuel ratio of the exhaust gas is leaner than the stoichiometric air-fuel ratio.

$$\text{limiting current } IL = DO2 \cdot \left(\frac{4F}{RT}\right) \cdot \left(\frac{S}{I}\right) \cdot \ln(Poe - Pod) \quad (14)$$

R: gas constant F: Faraday constant T: absolute temperature
S: electrode area
 (exhaust-gas-side electrode layer, atmosphere-side electrode layer)
I: diffusion distance
DO2: diffusion coefficient of oxygen gas in diffusion resistance layer
Poe: partial pressure of oxygen in exhaust gas
Pod: partial pressure of oxygen on exhaust-gas-side electrode layer A case in which the air-fuel ratio of the exhaust gas is richer than the stoichiometric air-fuel ratio.

$$\text{limiting current } IL = -Dg \cdot \left(\frac{4F}{RT}\right) \cdot \left(\frac{S}{I}\right) \cdot \ln(Pe - Pd) \quad (15)$$

R: gas constant F: Faraday constant T: absolute temperature
S: electrode area
 (exhaust-gas-side electrode layer, atmosphere-side electrode layer)
I: diffusion distance
Dg: diffusion coefficient of various unburnt substances in diffusion resistance layer
Poe: partial pressure of unburnt substances in exhaust gas
Pod: partial pressure of unburnt substances on exhaust-gas-side electrode layer As is apparent from the formula (14) and the formula (15), the limiting current IL varies depending on the partial pressure of "oxygen or unburnt substances" on the exhaust-gas-side electrode layer 562. Accordingly, the limiting current IL changes in accordance with a pressure Pex of the "exhaust gas reaching the upstream air-fuel ratio sensor 56."

In view of the above, the second control apparatus adopts, as the above described first relationship, the "relationship between (among) the output value Vabyfs of the air-fuel ratio sensor, the alcohol concentration Et, the air-fuel ratio imbalance indicating value RIMB, the pressure Pex of the exhaust gas reaching the air-fuel ratio sensor, and the actual detected air-fuel ratio abyfsact serving as the first air-fuel ratio correlated parameter." Further, the second control apparatus obtains the actual detected air-fuel ratio abyfsact, using the first relationship, based on "the actual output value Vabyfs, the actual alcohol concentration Et, the actual air-fuel ratio imbalance indicating value RIMB, and the actual pressure Pex." The second control apparatus performs the main feedback control using the actual detected air-fuel ratio abyfsact.

Furthermore, the second control apparatus adopts, as the above described second relationship, the "relationship between (among) the output value Vabyfs of the air-fuel ratio sensor, the alcohol concentration Et, the pressure Pex of the exhaust gas reaching the air-fuel ratio sensor, and the second air-fuel ratio correlated parameter (tentative detected air-fuel ratio abyfsvir) correlated to the true air-fuel ratio of the exhaust gas." The second control apparatus obtains the tentative detected air-fuel ratio abyfsvir, using the second relationship, based on "the actual output value Vabyfs, the actual alcohol concentration Et, and the actual pressure Pex." The second control apparatus obtains the air-fuel ratio imbalance indicating value RIMB using the tentative detected air-fuel ratio abyfsvir.

(Actual Operation)

Figure 16:
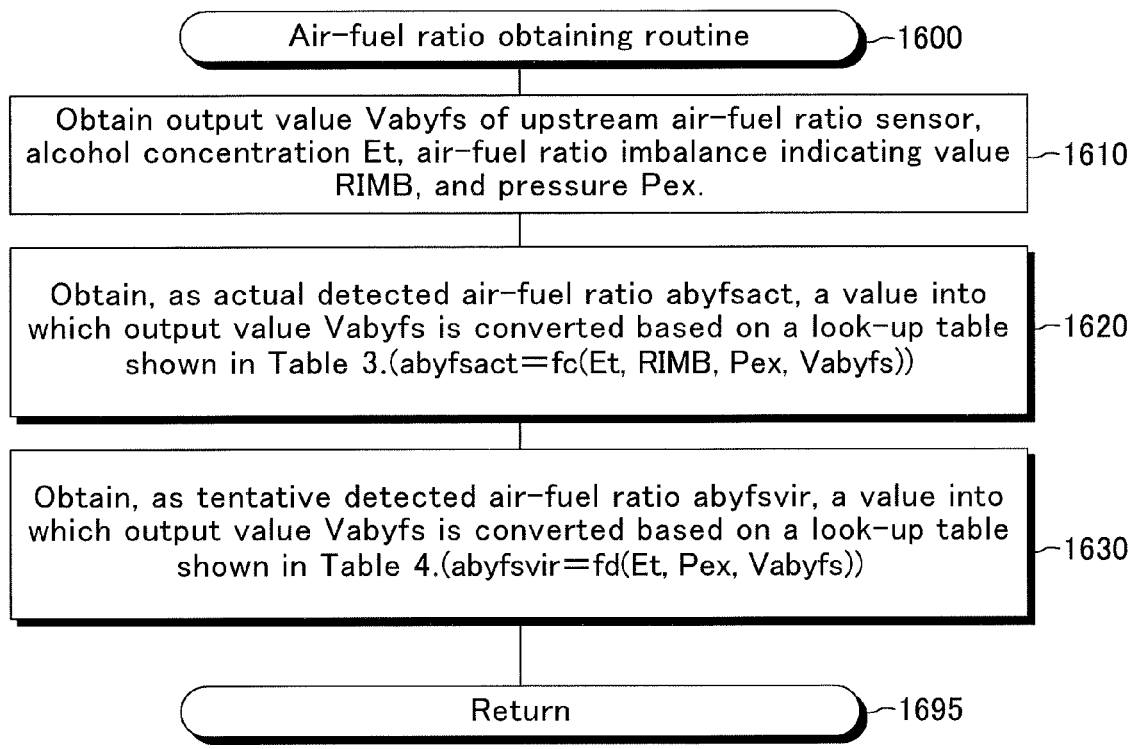
FIG. 16 is a flowchart showing a routine executed by a CPU of a fuel injection amount control apparatus (second control apparatus) according to a second embodiment of the present invention.

The CPU of the second control apparatus executes the routines shown in FIGS. 11, 13, and 15, and executes an "air-fuel ratio obtaining routine" shown in FIG. 16 in place of the routine shown in FIG. 12 every elapse of a predetermined time. The routines shown in FIGS. 11, 13, and 15 have already been described. Accordingly, the routine shown in FIG. 16 will next be described.

At an appropriate timing, the CPU starts the process from step 1600 to sequentially execute processes from step 1610 to step 1630 described below one after another, and then proceeds to step 1695 to end the present routine tentatively.

Step 1610: The CPU obtains the actual output value Vabyfs of the upstream air-fuel ratio sensor 56, the actual alcohol concentration Et, the actual pressure Pex, and the actual air-fuel ratio imbalance indicating value RIMB. The CPU obtains the actual alcohol concentration Et from the alcohol concentration sensor 59. The CPU read out, as the actual air-fuel ratio imbalance indicating value RIMB, the value which has been calculated by the routine shown in FIG. 15. The CPU estimates the "actual pressure Pex" based on the intake air-flow amount (rate) Ga and the engine rotational speed NE. For example, the actual pressure Pex is estimated as a value which becomes larger as the intake air amount Ga becomes larger and as the engine rotational speed NE becomes larger. The second control apparatus may be configured so as to comprise a pressure sensor in the vicinity of the upstream air-fuel ratio sensor 56, and so as to obtain the "actual pressure Pex" from the pressure sensor.

Step 1620: The CPU obtains the actual detected air-fuel ratio abyfsact by applying "the actual alcohol concentration Et, the actual air-fuel ratio imbalance indicating value RIMB, the actual pressure Pex, and the actual output value Vabyfs" obtained at step 1610 to a "look-up table shown in a Table 3 described below." This actual detected air-fuel ratio abyfsact is used in the routine shown in FIG. 13 for performing the main feedback control.

The look-up table shown in the Table 3 is formed/generated based on data obtained in advance by the experiments, or the like, and defines the "relationship among the alcohol concentration Et, the air-fuel ratio imbalance indicating value RIMB, the pressure Pex of the exhaust gas reaching the upstream air-fuel ratio sensor 56, the output value Vabyfs of the upstream air-fuel ratio sensor 56, and the actual detected air-fuel ratio abyfsact which is the first air-fuel ratio correlated parameter correlated to the air-fuel ratio."

The relationship defined by the look-up table shown in the Table 3 is the above described first relationship. Accordingly, at step 1620, the CPU obtains the actual detected air-fuel ratio abyfsact (first air-fuel ratio correlated parameter) which is used for the main feedback control, using the first relationship, based on "the actual alcohol concentration Et, the actual air-fuel ratio imbalance indicating value RIMB, the actual pressure Pex, and the actual output value Vabyfs."

It should be noted that the "conversion of the output value Vabyfs into the actual detected air-fuel ratio abyfsact" according to the look-up table shown in the Table 3 can be expressed by a function fc. In this case, the equation abyfsact=fc(Et, RIMB, Pex, Vabyfs) can be satisfied.

TABLE 3

| Input | | | | Output |
|---|---|---|---|---|
| alcohol concentration Et | air-fuel ratio imbalance indicating value RIMB | exhaust gas pressure Pex | output value Vabyfs of air-fuel ratio sensor | actual detected air-fuel ratio abyfsact |
| 0 | 0 | p1 | v1 | af(0,0,p1,v1) |
| 0 | 0 | p1 | v2 | af(0,0,p1,v2) |
| . | . | . | . | . |
| . | . | . | . | . |
| . | . | . | . | . |
| 0 | 0 | p1 | vn | af(0,0,p1,vn) |
| 0 | 0 | p2 | v1 | af(0,0,p2,v1) |
| 0 | 0 | p2 | v2 | af(0,0,p2,v2) |
| . | . | . | . | . |
| . | . | . | . | . |
| . | . | . | . | . |
| 0 | 0 | pn | vn | af(0,0,pn,vn) |
| 0 | r1 | p1 | v1 | af(0,r1,p1,v1) |
| 0 | r1 | p1 | v2 | af(0,r1,p1,v2) |
| . | . | . | . | . |
| . | . | . | . | . |
| . | . | . | . | . |
| 0 | rn | pn | vn | af(0,rn,pn,vn) |
| e1 | 0 | p1 | v1 | af(e1,0,p1,v1) |
| . | . | . | . | . |
| . | . | . | . | . |
| . | . | . | . | . |
| . | . | . | . | . |
| ei | rj | pm | vk | af(ei,rj,pm,vk) |
| . | . | . | . | . |
| . | . | . | . | . |
| . | . | . | . | . |
| en | rn | pn | vn | af(en,rn,pn,vn) |

Step 1630: The CPU obtains the "tentative detected air-fuel ratio abyfsvir (alcohol concentration•air-fuel ratio imbalance indicating value corrected air-fuel ratio, second air-fuel ratio correlated parameter)" by applying "the alcohol concentration Et, the pressure Pex, and the output value Vabyfs" that are obtained at step 1610 to a "look-up table shown in a Table 4 described below." The tentative detected air-fuel ratio abyfsvir is used in the routine shown in FIG. 15 for calculating the air-fuel ratio imbalance indicating value RIMB.

The look-up table shown in the Table 4 is formed/generated based on data obtained in advance by the experiments, or the like, and defines the "relationship among the alcohol concentration Et, the pressure Pex, the output value Vabyfs, and the tentative detected air-fuel ratio abyfsvir which is the second air-fuel ratio correlated parameter correlated to the air-fuel ratio", in a case in which the non-uniformity among the cylinder-by-cylinder air-fuel ratios is not occurring (i.e., when the air-fuel ratio imbalance indicating value RIMB is equal to "0").

The relationship defined by the look-up table shown in the Table 4 is the above described second relationship. Accordingly, at step 1630, the CPU obtains the tentative detected air-fuel ratio abyfsvir (second air-fuel ratio correlated parameter), using the second relationship, based on "the actual alcohol concentration Et, the actual pressure Pex, and the actual output value Vabyfs."

It should be noted that the "conversion of the output value Vabyfs into the tentative detected air-fuel ratio abyfsvir" according to the look-up table shown in the Table 4 can be expressed by a function fd. In this case, the equation abyfsvir=fd(Et, Pex, Vabyfs) can be satisfied.

TABLE 4

| Input | | | Output |
|---|---|---|---|
| alcohol concentration Et | exhaust gas pressure Pex | output value Vabyfs of air-fuel ratio sensor | tentative detected air-fuel ratio abyfsvir |
| 0 | p1 | v1 | af(0,p1,v1) |
| 0 | p1 | v2 | af(0,p1,v2) |
| . | . | . | . |
| . | . | . | . |
| . | . | . | . |
| 0 | p1 | vn | af(0,p1,vn) |
| 0 | p2 | v1 | af(0,p2,v1) |
| 0 | p2 | v2 | af(0,p2,v2) |
| . | . | . | . |
| . | . | . | . |
| . | . | . | . |
| 0 | p2 | vn | af(0,p2vn) |
| 0 | p3 | v1 | af(0,p3,v1) |
| . | . | . | . |
| . | . | . | . |
| . | . | . | . |
| 0 | p3 | vn | af(0,p3,vn) |
| . | . | . | . |
| . | . | . | . |
| . | . | . | . |
| 0 | pn | vn | af(0,pn,vn) |
| e1 | p1 | v1 | af(e1,p1,v1) |
| . | . | . | . |
| . | . | . | . |
| . | . | . | . |
| ei | pm | vk | af(ei,pm,vk) |
| . | . | . | . |
| . | . | . | . |
| . | . | . | . |

TABLE 4-continued

| Input | | | Output |
|---|---|---|---|
| alcohol concentration Et | exhaust gas pressure Pex | output value Vabyfs of air-fuel ratio sensor | tentative detected air-fuel ratio abyfsvir |
| . | . | . | . |
| . | . | . | . |
| . | . | . | . |
| en | pn | vn | af(en,pn,vn) |

As described above, in the second control apparatus, the above described first relationship is a relationship among the output value Vabyfs of the air-fuel ratio sensor 56, the alcohol concentration Et, the air-fuel ratio imbalance indicating value RIMB, the pressure Pex of the exhaust gas reaching the air-fuel ratio sensor 56, and the first air-fuel ratio correlated parameter (actual detected air-fuel ratio abyfsact) (refer to the Table 3).

Further, the first air-fuel ratio correlated parameter obtaining section of the second control apparatus is configured so as to convert the actual output value Vabyfs of the air-fuel ratio sensor 56 into the actual first air-fuel ratio correlated parameter (actual detected air-fuel ratio abyfsact) based on not only the actual alcohol concentration Et and the actual air-fuel ratio imbalance indicating value RIMB but also the actual pressure Pex (step 1620 shown in FIG. 16).

Accordingly, even when the output value Vabyfs of the air-fuel ratio sensor 56 is affected by the pressure Pex of the exhaust gas, it is possible to obtain the actual detected air-fuel ratio abyfsact which represents the true air-fuel ratio of the exhaust gas with high accuracy. Consequently, by means of the main feedback control, the it is possible to have the true air-fuel ratio of the exhaust gas come closer to the target air-fuel ratio abyfr, with higher accuracy.

Further, in the second control apparatus, the second relationship described above is the relationship among the output value Vabyfs of the upstream air-fuel ratio sensor 56, the alcohol concentration Et, the pressure Pex of the exhaust gas reaching the air-fuel ratio sensor 56, and the second air-fuel ratio correlated parameter (tentative detected air-fuel ratio abyfsvir) (refer to the Table 4).

That is, the air-fuel ratio imbalance indicating value obtaining section of the second control apparatus is configured so as to convert the actual output value Vabyfs of the air-fuel ratio sensor 56 into the actual second air-fuel ratio correlated parameter (tentative detected air-fuel ratio abyfsvir) based on not only the actual alcohol concentration Et but also the actual pressure Pex (step 1630 shown in FIG. 16).

Accordingly, the tentative detected air-fuel ratio abyfsvir which is base data for obtaining the air-fuel ratio imbalance indicating value RIMB is a value, which does not vary depending on the air-fuel ratio imbalance indicating value RIMB itself, and which is obtained by eliminating the effect on the output value Vabyfs which "the alcohol concentration Et and the pressure Pex" have. Consequently, it is possible to obtain the air-fuel ratio imbalance indicating value RIMB which represents the degree of the non-uniformity among the cylinder-by-cylinder air-fuel ratios with high accuracy.

Third Embodiment

Next, There Will Be Described a Control Apparatus According To a Third embodiment of the present invention (hereinafter, simply referred to as a "third control apparatus").

The second control apparatus directly converts the actual output value Vabyfs into the actual detected air-fuel ratio abyfsact based on the actual alcohol concentration Et, the actual air-fuel ratio imbalance indicating value RIMB, the actual pressure Pex, and the first relationship. Further, the second control apparatus directly converts the actual output value Vabyfs into the tentative detected air-fuel ratio abyfsvir based on the actual alcohol concentration Et, the actual pressure Pex, and the second relationship.

In contrast, the third control apparatus obtains a pressure corrected output value VafsP by correcting the actual output value Vabyfs based on the actual pressure Pex. That is, the actual output value Vabyf is converted into an output value on the assumption that the pressure Pex when the output value Vabyfs was obtained is equal to a predetermined base (reference) pressure, and the thus converted output value is obtained as the pressure corrected output value VafsP.

Subsequently, the third control apparatus obtains a pressure•alcohol-concentration corrected output value VafsPE by correcting the pressure corrected output value VafsP based on the actual alcohol concentration Et. That is, the pressure corrected output value VafsP is converted into an output value on the assumption that the alcohol concentration Et when the output value Vabyfs was obtained is equal to a predetermined base (reference) alcohol concentration (in the present example, "0"), and the thus converted output value is obtained as the pressure•alcohol-concentration corrected output value VafsPE.

Further, the third control apparatus obtains a tentative detected air-fuel ratio abyfsvir (second air-fuel ratio correlated parameter) by applying the pressure•alcohol-concentration corrected output value VafsPE to an "air-fuel ratio conversion table Map1(Vabyfs) which is determined for a case in which the pressure Pex is equal to the predetermined base pressure, the non-uniformity among the cylinder-by-cylinder air-fuel ratios is not occurring, and the fuel whose alcohol concentration is equal to "0" which is the base alcohol concentration is used." Thus obtained tentative detected air-fuel ratio abyfsvir is an air-fuel ratio obtained based on an output value which is obtained by eliminating an effect on the output value Vabyfs which the pressure Pex and the alcohol concentration Et have. The third control apparatus obtains the air-fuel ratio imbalance indicating value RIMB based on that tentative detected air-fuel ratio abyfsvir, similarly to the other control apparatuses.

Subsequently, the third control apparatus obtains a pressure•alcohol-concentration•imbalance-ratio corrected output value (pressure•alcohol-concentration•imbalance-indicating-value corrected output value) VafsPER by correcting the pressure•alcohol-concentration corrected output value VafsPE based on the actual air-fuel ratio imbalance indicating value RIMB. That is, the pressure•alcohol-concentration corrected output value VafsPE is converted into an output value on the assumption that the non-uniformity among the cylinder-by-cylinder air-fuel ratios was not present (air-fuel ratio imbalance indicating value RIMB was "0" which is the base value) when the output value Vabyfs was obtained, and the thus converted output value is obtained as the pressure•alcohol-concentration•imbalance-ratio corrected output value VafsPER.

Further, the third control apparatus obtains the actual detected air-fuel ratio abyfsact (first air-fuel ratio correlated parameter) by applying the pressure•alcohol-concentration•imbalance-ratio corrected output value VafsPER to an "air-fuel ratio conversion table Map1(Vabyfs) which is determined for a case in which the pressure Pex is equal to the predetermined base pressure, the non-uniformity among the cylinder-by-cylinder air-fuel ratios is not occurring, and the fuel whose alcohol concentration is equal to "0" which is the base alcohol concentration is used." Thus obtained actual detected air-fuel ratio abyfsact is an air-fuel ratio obtained based on an output value of the air-fuel ratio sensor 56 which is obtained by eliminating an "effect on the output value Vabyfs which the pressure Pex, the alcohol concentration Et, and the air-fuel ratio imbalance indicating value RIMB have." Accordingly, the actual detected air-fuel ratio abyfsact substantially coincides with the "true air-fuel ratio of the exhaust gas." The third control apparatus performs the main feedback control based on that actual detected air-fuel ratio abyfsact.

(Actual Operation)

Figure 17:
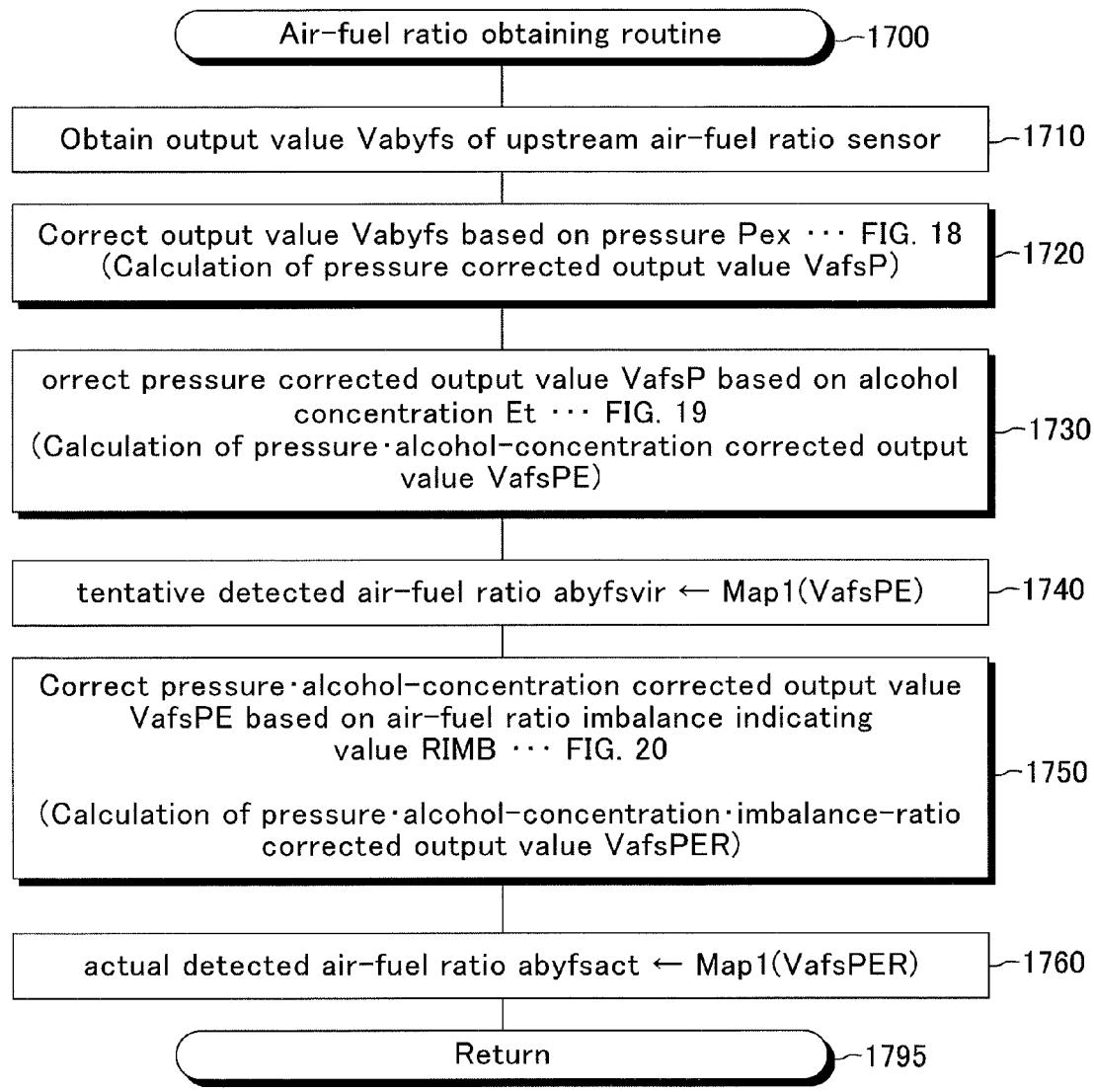
FIG. 17 is a flowchart showing a routine executed by a CPU of a fuel injection amount control apparatus (third control apparatus) according to a third embodiment of the present invention.

The CPU of the third control apparatus executes the routines shown in FIGS. 11, 13, and 15, and executes an "air-fuel ratio obtaining routine" shown in FIG. 17 in place of the routine shown in FIG. 12 every elapse of a predetermined time. The routines shown in FIGS. 11, 13, and 15 have already been described. Accordingly, the routine shown in FIG. 17 will next be described.

At an appropriate timing, the CPU starts the process from step 1700 to sequentially execute processes from step 1710 to step 1760 described below one after another, and then proceeds to step 1795 to end the present routine tentatively.

Step 1710: The CPU obtains the actual output value Vabyfs of the upstream air-fuel ratio sensor 56.

Figure 18:
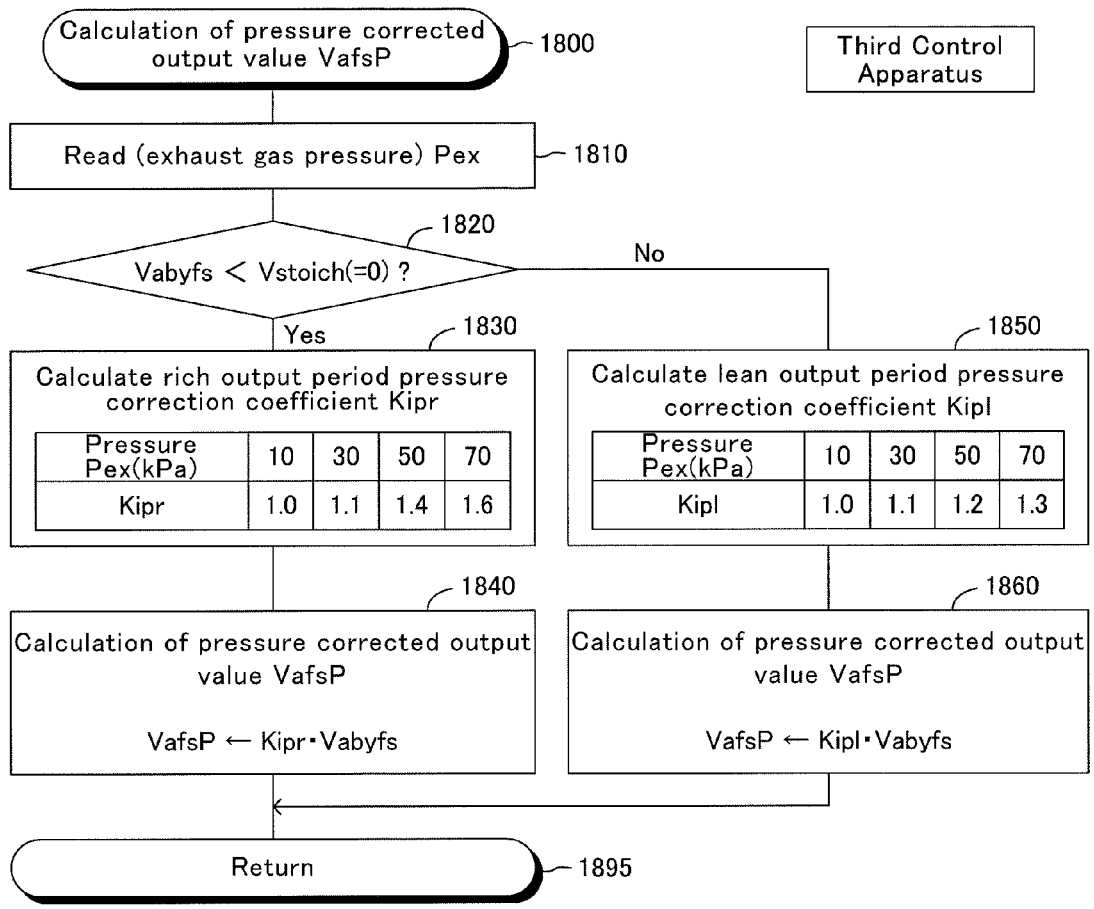
FIG. 18 is a flowchart showing a routine executed by the CPU of the third control apparatus.

Step 1720: The CPU corrects the actual output value Vabyfs based on the actual pressure Pex. More specifically, when the CPU proceeds to step 1720, the CPU starts processes of a "pressure corrected output value calculation routine" shown in FIG. 18 from step 1800, and obtains the actual pressure Pex at following step 1810.

Subsequently, the CPU proceeds to step 1820 to determine whether or not the actual output value Vabyfs is smaller than the stoichiometric air-fuel ratio corresponding value Vstoich (=0). In other words, the CPU determines whether or not the limiting current IL is a negative current (current indicated in (C) of FIG. 3) at step 1820. The reason for performing this determination is because the way of generation of the limiting current IL is different depending on whether air-fuel ratio of the exhaust gas is lean or rich, as shown in the formulas (14) and (15) described above.

When the actual output value Vabyfs is smaller than the stoichiometric air-fuel ratio corresponding value Vstoich (=0), the CPU makes a "Yes" determination at step 1820 to proceed to step 1830, at which the CPU calculates a "rich output period pressure correction coefficient Kipr" based on the actual pressure Pex. The rich output period pressure correction coefficient Kipr is determined in such a manner that the rich output period pressure correction coefficient Kipr becomes larger within a range larger than "1" as the actual pressure Pex becomes larger.

Subsequently, the CPU proceeds to step 1840 to calculate the pressure corrected output value VafsP by multiplying the actual output value Vabyfs by the rich output period pressure correction coefficient Kipr. Thereafter, the CPU proceeds to step 1730 shown in FIG. 17 via step 1895.

In contrast, if the actual output value Vabyfs is equal to or larger than the stoichiometric air-fuel ratio corresponding value Vstoich (=0) when the CPU executes the process of step 1820, the CPU makes a "No" determination at step 1820 to proceed to step 1850, at which the CPU calculates a "lean output period pressure correction coefficient Kipl" based on the actual pressure Pex. The lean output period pressure correction coefficient Kipl is determined in such a manner that the lean output period pressure correction coefficient Kipl becomes larger within a range larger than "1" as the actual pressure Pex becomes larger. Note, however, the lean output period pressure correction coefficient Kipl is equal to or smaller than the rich output period pressure correction coefficient Kipr, when the pressure Pex is a "certain value."

Subsequently, the CPU proceeds to step 1860 to calculate the pressure corrected output value VafsP by multiplying the actual output value Vabyfs by the lean output period pressure correction coefficient Kipl. Thereafter, the CPU proceeds to step 1730 shown in FIG. 17 via step 1895.

Figure 19:
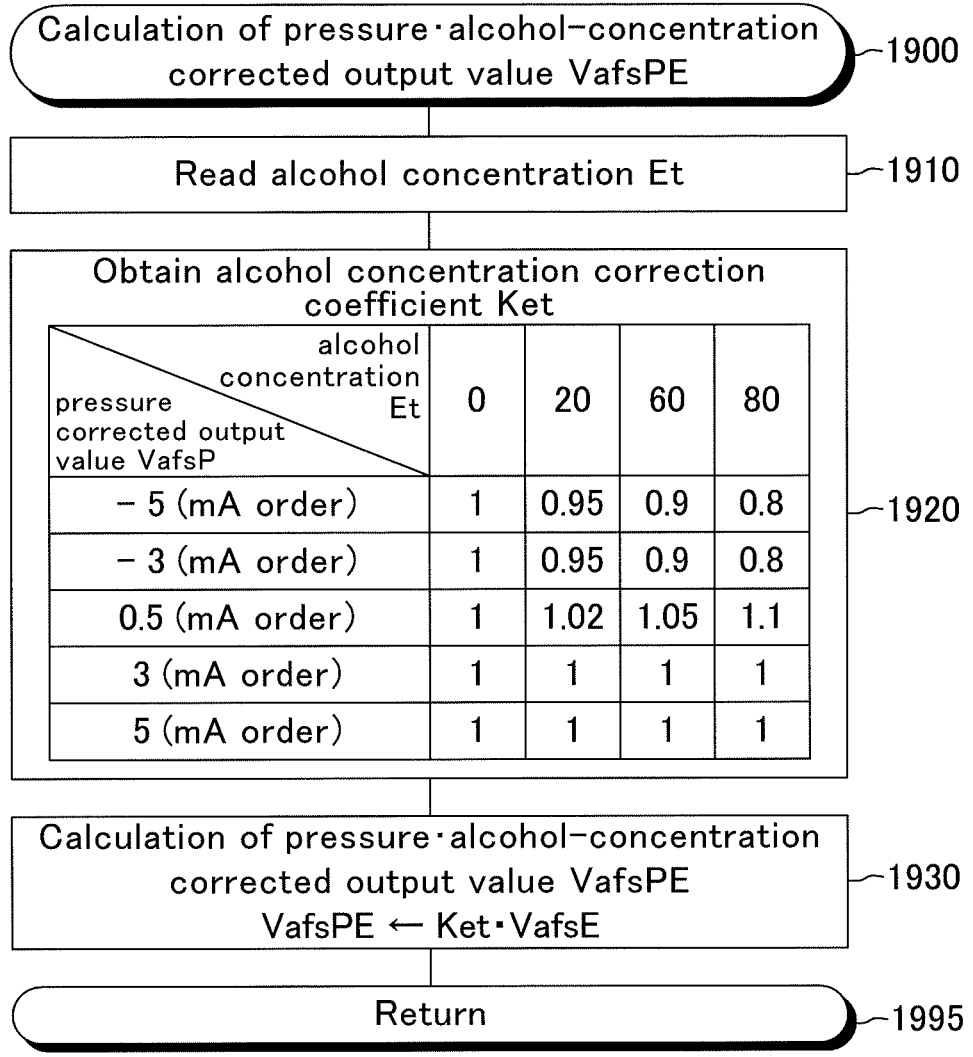
FIG. 19 is a flowchart showing a routine executed by the CPU of the third control apparatus.

Step 1730: The CPU corrects the pressure corrected output value VafsP based on the actual alcohol concentration Et. More specifically, when the CPU proceeds to step 1730, the CPU starts processes of a "pressure•alcohol-concentration corrected output value calculation routine" shown in FIG. 19 from step 1900, and obtains the actual alcohol concentration Et at following step 1910.

Subsequently, the CPU proceeds to step 1920 to calculate an "alcohol concentration correction coefficient Ket" based on the actual alcohol concentration Et and the actual pressure corrected output value VafsP. More specifically, the CPU obtains the alcohol concentration correction coefficient Ket by applying the actual alcohol concentration Et and the actual pressure corrected output value VafsP to a "look-up table stored in the ROM" which defines a "relationship between (among) the alcohol concentration Et, the pressure corrected output value VafsP, and the alcohol concentration correction coefficient Ket" shown in step 1920.

It should be noted that the alcohol concentration correction coefficient Ket is set to (at) "1" when the actual alcohol concentration Et is equal to "0" which is the base value, according that look-up table. This is because, when the alcohol concentration Et is equal to "0", the output value Vabyfs is not affected by the preferential diffusion of hydrogen. Further, the alcohol concentration correction coefficient Ket is set to (at) "1" when the pressure corrected output value VafsP is equal to or larger than a "value corresponding to limiting current IL of 3 mA (that is, the pressure corrected output value VafsP corresponds to an air-fuel ratio leaner than a predetermined lean air-fuel ratio). This is because the unburnt substances including hydrogen are not substantially produced when the air-fuel ratio is leaner than the predetermined lean air-fuel ratio, and thus, the output value Vabyfs is not affected by the preferential diffusion of hydrogen.

Furthermore, according that look-up table, the alcohol concentration correction coefficient Ket is determined in such a manner that the alcohol concentration correction coefficient Ket becomes smaller within a range smaller than "1" as the alcohol concentration Et becomes higher, and the alcohol concentration correction coefficient Ket becomes larger as the pressure corrected output value VafsP becomes larger.

Subsequently, the CPU proceeds to step 1930 to calculate the pressure•alcohol-concentration corrected output value VafsPE by multiplying the pressure corrected output value VafsP by the alcohol concentration correction coefficient Ket. Thereafter, the CPU proceeds to step 1740 shown in FIG. 17 via step 1995.

Step 1740: The CPU obtains the tentative detected air-fuel ratio abyfsvir by applying the pressure•alcohol-concentration corrected output value VafsPE to the air-fuel ratio conversion table Map1(Vabyfs) described above.

Figure 20:
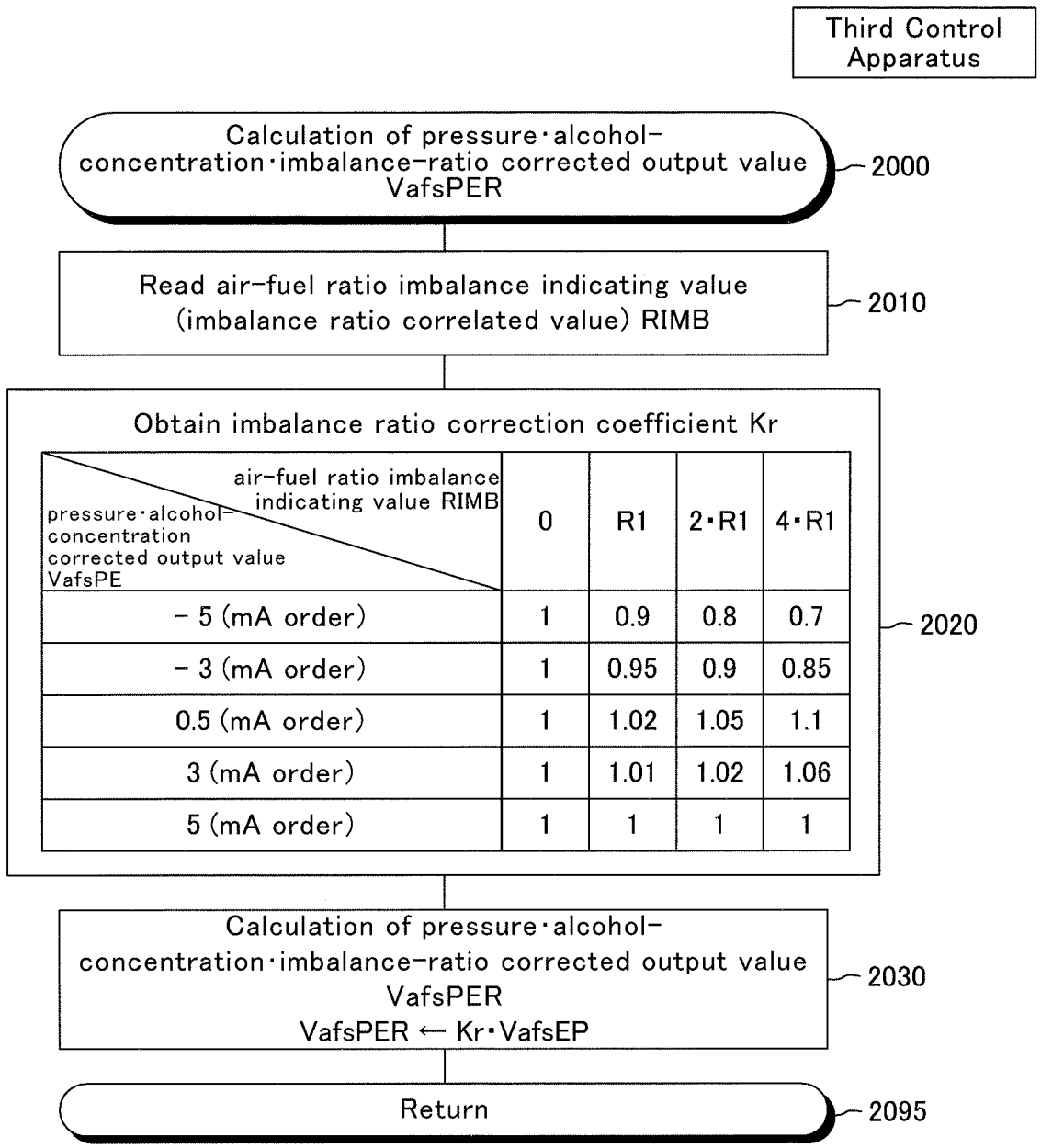
FIG. 20 is a flowchart showing a routine executed by the CPU of the third control apparatus.

Step 1750: The CPU corrects the pressure•alcohol-concentration corrected output value VafsPE based on the actual air-fuel ratio imbalance indicating value RIMB. More specifically, when the CPU proceeds to step 1750, the CPU starts processes of a "pressure•alcohol-concentration•imbalance-ratio corrected output value calculation routine" shown in FIG. 20 from step 2000, and obtains the actual air-fuel ratio imbalance indicating value RIMB at following step 2010.

Subsequently, the CPU proceeds to step 2020 to calculate an "imbalance ratio correction coefficient Kr" based on the actual air-fuel ratio imbalance indicating value RIMB and the actual pressure•alcohol-concentration corrected output value VafsP E. More specifically, the CPU obtains the imbalance ratio correction coefficient Kr by applying the actual air-fuel ratio imbalance indicating value RIMB and the actual pressure•alcohol-concentration corrected output value VafsPE to a "look-up table stored in the ROM" which defines a "relationship between (among) the air-fuel ratio imbalance indicating value RIMB, the pressure•alcohol-concentration corrected output value VafsPE, and the imbalance ratio correction coefficient Kr" shown in step 2020.

It should be noted that the imbalance ratio correction coefficient Kr is set to (at) "1" when the actual air-fuel ratio imbalance indicating value RIMB is equal to "0" which is the base value, according that look-up table. This is because, when the air-fuel ratio imbalance indicating value RIMB is equal to "0", the output value Vabyfs is not affected by the preferential diffusion of hydrogen. Further, the imbalance ratio correction coefficient Kr is set to (at) "1" when the pressure•alcohol-concentration corrected output value VafsPE is equal to or larger than a "value corresponding to limiting current IL of 5 mA (that is, the pressure•alcohol-concentration corrected output value VafsPE corresponds to an air-fuel ratio leaner than a predetermined lean air-fuel ratio). This is because the unburnt substances including hydrogen are not substantially produced when the air-fuel ratio is leaner than the predetermined lean air-fuel ratio, and thus, the output value Vabyfs is not affected by the preferential diffusion of hydrogen.

Furthermore, according that look-up table, the imbalance ratio correction coefficient Kr is determined in such a manner that the imbalance ratio correction coefficient Kr becomes smaller within a range smaller than "1" as the air-fuel ratio imbalance indicating value RIMB becomes larger, the imbalance ratio correction coefficient Kr becomes larger as the pressure•alcohol-concentration corrected output value VafsPE becomes larger when the pressure•alcohol-concentration corrected output value VafsPE is within a range equal to or smaller than a specific value (limiting current IL of 0.5 mA) in the lean side, and the imbalance ratio correction coefficient Kr becomes smaller as the pressure•alcohol-concentration corrected output value VafsPE becomes larger when the pressure•alcohol-concentration corrected output value VafsPE is within a range larger than the specific value.

Subsequently, the CPU proceeds to step 2030 to calculate the pressure•alcohol-concentration•imbalance-ratio corrected output value VafsPER by multiplying the pressure•alcohol-concentration corrected output value VafsPE by the imbalance ratio correction coefficient Kr. Thereafter, the CPU proceeds to step 1780 shown in FIG. 17 via step 2095.

Step 1760: The CPU obtains the actual detected air-fuel ratio abyfsact by applying the pressure•alcohol-concentration•imbalance-ratio corrected output value VafsPER to the air-fuel ratio conversion table Map1(Vabyfs) described above.

As described above, the third control apparatus corrects the output value Vabyfs further based on the pressure Pex, and thus, can obtain the "actual detected air-fuel ratio abyfsact which indicates the true air-fuel ratio of the exhaust gas with high accuracy, and the tentative detected air-fuel ratio abyfsvir appropriate for obtaining the air-fuel ratio imbalance indicating value RIMB which indicates the degree of the non-uniformity among the cylinder-by-cylinder air-fuel ratios with high accuracy" regardless of the pressure Pex.

Fourth Embodiment

Next, there will be described a control apparatus according to a fourth embodiment of the present invention (hereinafter, simply referred to as a "fourth control apparatus").

The third control apparatus obtains the pressure•alcohol-concentration corrected output value VafsPE by correcting the "pressure corrected output value VafsP which is obtained by correcting the output value Vabyfs based on the pressure Pex" based on the alcohol concentration Et, and obtains the tentative detected air-fuel ratio abyfsvir by applying the pressure•alcohol-concentration corrected output value VafsPE to the air-fuel ratio conversion table Map1(Vabyfs).

Further, the third control apparatus obtains the pressure alcohol-concentration•imbalance-ratio corrected output value VafsP ER by correcting the pressure•alcohol-concentration corrected output value VafsPE based on the air-fuel ratio imbalance indicating value RIMB, and obtains the actual detected air-fuel ratio abyfsact by applying the pressure•alcohol-concentration•imbalance-ratio corrected output value VafsP ER to the air-fuel ratio conversion table Map1(Vabyfs).

In contrast, the fourth control apparatus obtains the tentative detected air-fuel ratio abyfsvir and the actual detected air-fuel ratio abyfsact without correcting the output value Vabyfs by the pressure Pex. That is, the fourth control apparatus obtains the alcohol-concentration corrected output value VafsE by correcting the output value Vabyfs based on the alcohol concentration Et, and obtains the tentative detected air-fuel ratio abyfsvir by applying the alcohol-concentration corrected output value VafsE to the air-fuel ratio conversion table Map1(Vabyfs).

Further, the fourth control apparatus obtains the alcohol-concentration•imbalance-ratio corrected output value (alcohol-concentration•air-fuel ratio imbalance indicating value corrected output value) VafsER by correcting the alcohol-concentration corrected output value VafsE based on the air-fuel ratio imbalance indicating value RIMB, and obtains the actual detected air-fuel ratio abyfsact by applying the alcohol-concentration•imbalance-ratio corrected output value VafsER to the air-fuel ratio conversion table Map1(Vabyfs).

(Actual Operation)

Figure 21:
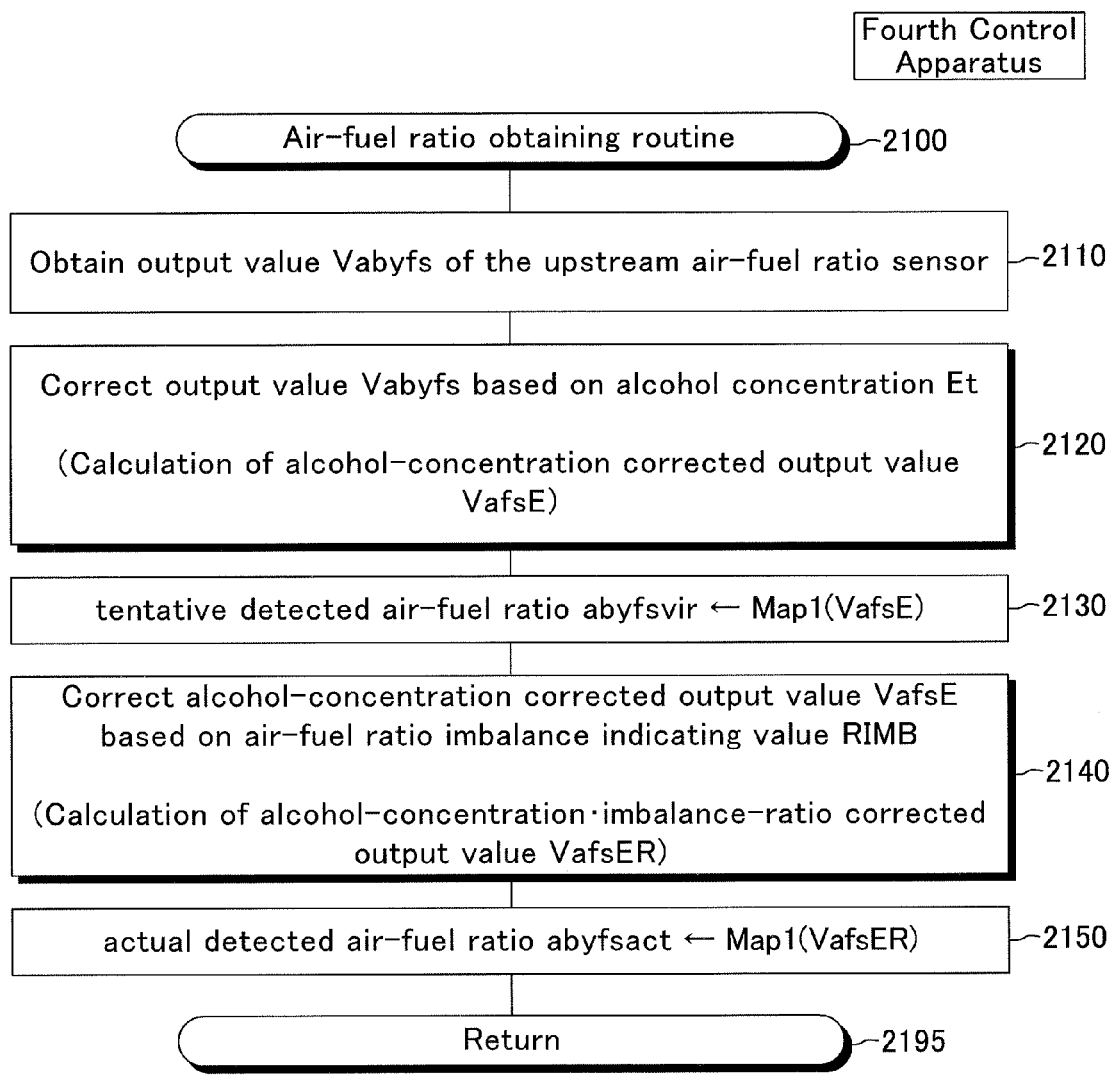
FIG. 21 is a flowchart showing a routine executed by a CPU of a fuel injection amount control apparatus (fourth control apparatus) according to a fourth embodiment of the present invention.

The CPU of the fourth control apparatus executes the routines shown in FIGS. 11, 13, and 15, and executes an "air-fuel ratio obtaining routine" shown in FIG. 21 in place of the routine shown in FIG. 12 every elapse of a predetermined time. The routines shown in FIGS. 11, 13, and 15 have already been described. Accordingly, the routine shown in FIG. 21 will next be described.

At an appropriate timing, the CPU starts the process from step 2100 to sequentially execute processes from step 2110 to step 2150 described below one after another, and then proceeds to step 2195 to end the present routine tentatively.

Step 2110: The CPU obtains the actual output value Vabyfs of the upstream air-fuel ratio sensor 56.

Step 2120: The CPU obtains the alcohol-concentration corrected output value VafsE by correcting the actual output value Vabyfs based on the actual alcohol concentration Et. More specifically, the CPU firstly reads out the actual alcohol concentration Et. Subsequently, the CPU calculates the alcohol-concentration corrected output value VafsE by applying the actual output value Vabyfs and the actual alcohol concentration Et to an "unillustrated first look-up table (or first function)." The first look-up table is a table, which is obtained by replacing the pressure corrected output value VafsP in step 1920 shown in FIG. 19 with (by) the output value Vabyfs, and has data that are products of each numerical value in the table of step 1920 and the corresponding output value Vabyfs in place of the each numerical value in the table of step 1920.

It should be noted that the CPU may obtain the alcohol concentration correction coefficient Ket based on the actual output value Vabyfs and the actual alcohol concentration Et, and calculates the alcohol-concentration corrected output value VafsE by multiplying the actual output value Vabyfs by the alcohol concentration correction coefficient Ket. The alcohol concentration correction coefficient Ket is calculated by applying "the actual alcohol concentration Et and the output value Vabyfs in place of the pressure corrected output value VafsP" to the look-up table shown in step 1920 in FIG. 19.

Step 2130: The CPU obtains the tentative detected air-fuel ratio abyfsvir (second air-fuel ratio correlated parameter) by applying the alcohol-concentration corrected output value VafsE to the air-fuel ratio conversion table Map1(Vabyfs).

Step 2140: The CPU obtains the alcohol-concentration•imbalance-ratio corrected output value VafsER by correcting the alcohol-concentration corrected output value VafsE based on the actual air-fuel ratio imbalance indicating value RIMB. More specifically, the CPU firstly reads out the actual air-fuel ratio imbalance indicating value RIMB. Subsequently, the CPU calculates the alcohol-concentration•imbalance-ratio corrected output value VafsER by applying the alcohol-concentration corrected output value VafsE and the actual air-fuel ratio imbalance indicating value RIMB to an "unillustrated second look-up table (or second function)." The second look-up table is a table, which is obtained by replacing the pressure•alcohol-concentration corrected output value VafsPE in step 2020 shown in FIG. 20 with (by) the alcohol-concentration corrected output value VafsE, and has data that are "products of each numerical value in the table of step 2020 and the alcohol-concentration corrected output value VafsE" in place of the each numerical value in the table of step 2020.

It should be noted that the CPU may obtain the imbalance ratio correction coefficient Kr based on the alcohol-concentration corrected output value VafsE and the actual air-fuel ratio imbalance indicating value RIMB, and calculates the alcohol-concentration•imbalance-ratio corrected output value VafsER by multiplying the alcohol-concentration corrected output value VafsE by the imbalance ratio correction coefficient Kr. The imbalance ratio correction coefficient Kr is calculated by applying "the actual air-fuel ratio imbalance indicating value RIMB and the alcohol-concentration corrected output value VafsE in place of the pressure•alcohol-concentration corrected output value VafsPE" to the look-up table shown in step 2020 in FIG. 20.

Step 2150: The CPU obtains the actual detected air-fuel ratio abyfsact (first air-fuel ratio correlated parameter) by applying the alcohol-concentration•imbalance-ratio corrected output value VafsER to the air-fuel ratio conversion table Map1(Vabyfs).

As described above, the first air-fuel ratio correlated parameter obtaining section of the fourth control apparatus is configured so as to store the first relationship as, the first look-up table or the first function for converting, based on the alcohol concentration, the output value of the air-fuel ratio sensor into an output value of the air-fuel ratio sensor in a case in which the alcohol concentration is equal to the predetermined base (reference) alcohol concentration (and the air-fuel ratio imbalance indicating value is equal to the predetermined base air-fuel ratio imbalance indicating value);

the second look-up table or the second function for converting, based on the air-fuel ratio imbalance indicating value, the output value of the air-fuel ratio sensor into an output value of the air-fuel ratio sensor in a case in which the air-fuel ratio imbalance indicating value is equal to the predetermined base (reference) air-fuel ratio imbalance indicating value (and the fuel whose alcohol concentration is equal to the base alcohol concentration is used); and the third look-up table or the third function for converting the output value of the air-fuel ratio sensor when the alcohol concentration is equal to the base alcohol concentration and the air-fuel ratio imbalance indicating value is equal to the base air-fuel ratio imbalance indicating value into an air-fuel ratio.

Further, the first air-fuel ratio correlated parameter obtaining section of the fourth control apparatus is configured so as to:

obtain, as the "alcohol concentration corrected output value VafsE", an output value of the air-fuel ratio sensor which is obtained by inputting the actual output value Vabyfs of the air-fuel ratio sensor 56 and the actual alcohol concentration Et to the first look-up table or the first function (step 2120 shown in FIG. 21);

obtain, as the alcohol concentration•air-fuel ratio imbalance indicating value corrected output value VafsER, an output value of the air-fuel ratio sensor which is obtained by inputting the alcohol concentration corrected output value VafsE and the actual air-fuel ratio imbalance indicating value RIMB to the second look-up table or the second function (step 2140 shown in FIG. 21); and obtain, as the actual first air-fuel ratio correlated parameter (actual detected air-fuel ratio abyfsact), an air-fuel ratio which is obtained by inputting the alcohol concentration•air-fuel ratio imbalance indicating value VafsER corrected output value to the third look-up table or the third function (step 2150 shown in FIG. 21).

Fifth Embodiment

Next, there will be described a control apparatus according to a fifth embodiment of the present invention (hereinafter, simply referred to as a "fifth control apparatus"). The fifth control apparatus is different from the first control apparatus in that the fifth control apparatus uses an "electro-motive-force-type oxygen concentration sensor (well-known concentration-cell-type oxygen concentration sensor using the solid electrolyte such as stabilized zirconia) which is the same as the downstream air-fuel ratio sensor 57", as the upstream air-fuel ratio sensor 56.

Figure 22:
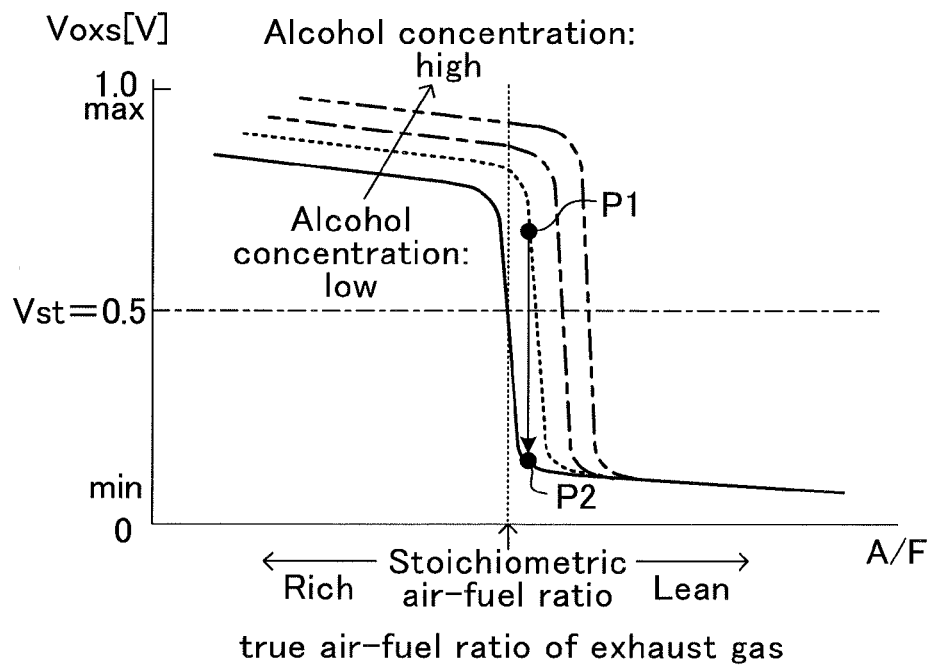
FIG. 22 is a graph showing a relationship between the alcohol concentration, the true air-fuel ratio of the exhaust gas, and the output value of the air-fuel ratio sensor which is an "electro-motive-force-type oxygen concentration sensor."
Figure 23:
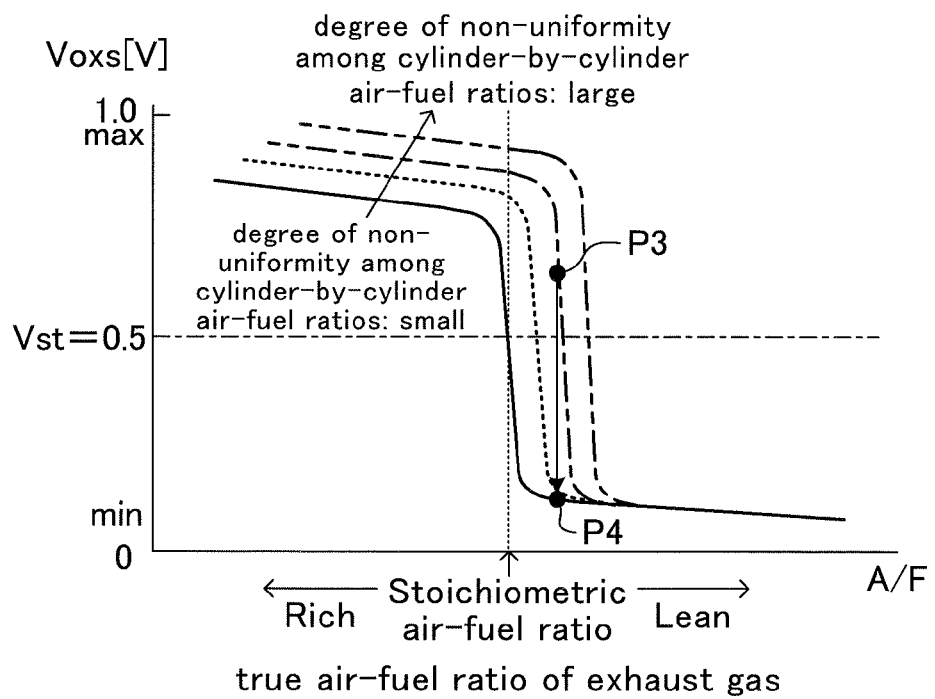
FIG. 23 is a graph showing a relationship between the degree of the non-uniformity among the cylinder-by-cylinder air-fuel ratios, the true air-fuel ratio of the exhaust gas, and the output value of the air-fuel ratio sensor which is an "electro-motive-force-type oxygen concentration sensor."

As described above, the electro-motive-force-type oxygen concentration sensor also includes the porous layer. Accordingly, when the electro-motive-force-type oxygen concentration sensor is disposed between the exhaust gas aggregated portion HK and the upstream catalyst 43, the output value Voxs of the electro-motive-force-type oxygen concentration sensor is affected by the preferential diffusion of hydrogen. This causes the output value Voxs with respect to the true air-fuel ratio of the exhaust gas to vary depending on the alcohol concentration, as shown in FIG. 22. Further, as shown in FIG. 23, the output value Voxs with respect to the true air-fuel ratio of the exhaust gas changes depending on the degree of the non-uniformity among the cylinder-by-cylinder air-fuel ratios.

Generally, when the electro-motive-force-type oxygen concentration sensor is used as the "upstream air-fuel ratio sensor for the main feedback control", the air-fuel ratio feedback control is carried out in such a manner that the output value Voxs coincides with a "target value Vref which is set at the value Vst corresponding to the base air-fuel ratio (e.g., stoichiometric air-fuel ratio)." Accordingly, if no correction is made on the output value Voxs, an average of the true air-fuel ratio obtained as a result of the feedback control shifts toward the air-fuel ratio which becomes leaner with respect to the stoichiometric air-fuel ratio as the alcohol concentration and/or the degree of the non-uniformity among the cylinder-by-cylinder air-fuel ratios become(s) larger. That is, the erroneous lean control occurs.

In view of the above, the fifth control apparatus corrects the actual output value Voxs by converting the actual output value Voxs into an output value when "the alcohol concentration Et is equal to "0" which is the base value, and the air-fuel ratio imbalance indicating value RIMB is equal to "0" which is the base value, and carries out the main feedback control using the "output value VoxsER which is the corrected value based on the alcohol concentration and the air-fuel ratio imbalance indicating value." Further, the fifth control apparatus corrects the actual output value Voxs by converting the actual output value Voxs into an output value when the alcohol concentration Et is equal to "0" which is the base value, and obtains the air-fuel ratio imbalance indicating value RIMB using the "output value VoxsE which is the corrected value based on the alcohol concentration."

The CPU of the fifth control apparatus performs the main feedback control as follows. That is, the fifth control apparatus stores, as a first look-up table (or a first function), in the ROM, a "relationship between (among) "the alcohol concentration, the output value Voxs, and the true air-fuel ratio of the exhaust gas (refer to FIG. 22)" when the non-uniformity among the cylinder-by-cylinder air-fuel ratios is not occurring. The solid line shown in FIG. 22 indicates the relationship between (among) "the alcohol concentration, the output value Voxs, and the true air-fuel ratio of the exhaust gas" when the alcohol concentration Et is equal to "0" which is the base value.

Further, the CPU of the fifth control apparatus obtains an alcohol-concentration corrected output value VoxsE serving as the second air-fuel ratio correlated parameter by applying "the actual output value Voxs and the actual alcohol concentration Et" to that look-up table. For example, according to the look-up table, the output value Voxs at a point P1 is converted into the alcohol-concentration corrected output value VoxsE at a point P2.

Furthermore, the CPU of the fifth control apparatus calculates the air-fuel ratio imbalance indicating value RIMB based on a differential value of the alcohol-concentration corrected output value VoxsE, using a method similar to one shown in the routine in FIG. 15. That is, the CPU replaces the tentative detected air-fuel ratio abyfsvir at step 1510 shown in FIG. 15 with (by) the alcohol-concentration corrected output value VoxsE so as to obtain the air-fuel ratio imbalance indicating value RIMB.

In addition, the fifth control apparatus stores, as a second look-up table (or a second function), in the ROM, a "relationship between (among) "the air-fuel ratio imbalance indicating value RIMB, the output value Voxs, and the true air-fuel ratio of the exhaust gas (refer to FIG. 23)" when the alcohol concentration Et is equal to "0" which is the base value. The solid line shown in FIG. 23 indicates the relationship between (among) "the air-fuel ratio imbalance indicating value RIMB, the output value Voxs, and the true air-fuel ratio of the exhaust gas" when the air-fuel ratio imbalance indicating value RIMB is equal to "0" which is the base air-fuel ratio imbalance indicating value. The first relationship is expressed (represented) based on the relationships shown in FIGS. 23 and 22.

Further, the CPU of the fifth control apparatus obtains an alcohol-concentration•imbalance-ratio corrected output value VoxsER serving as the first air-fuel ratio correlated parameter by applying "the actual alcohol-concentration corrected output value VoxsE and the actual air-fuel ratio imbalance indicating value RIMB" to the look-up table shown in FIG. 23. For example, according to the look-up table, the alcohol-concentration corrected output value VoxsE at a point P3 is converted into the alcohol-concentration•imbalance-ratio corrected output value VoxsER at a point P4.

Thereafter, the CPU performs a feedback control on a fuel amount based on the obtained alcohol-concentration•imbalance-ratio corrected output value VoxsER, in such a manner that the obtained alcohol-concentration•imbalance-ratio corrected output value VoxsER coincides with the target value Vref (e.g., Vst=0.5 V). The target value Vref is set at a "value which is equal to the output value of the air-fuel ratio sensor for a predetermined air-fuel ratio which is within the window of the three way catalyst 43" when the alcohol concentration Et is equal to the base alcohol concentration and the air-fuel ratio imbalance indicating value RIMB is equal to the base air-fuel ratio imbalance indicating value.

The CPU executes steps described below every elapse of a predetermined time.
(1) The CPU obtains an "output error amount Ds" by subtracting the "alcohol-concentration•imbalance-ratio corrected output value VoxsER" from the "target value Vref."
(2) The CPU obtains the main feedback amount DFi, according to a formula (16) described below. In the formula (16) below, Kpp is a predetermined proportion gain (proportion constant), Kii is a predetermined integration gain (integration constant), and Kdd is a predetermined differential gain (differential constant). The SDs is an integrated value of the output error amount Ds, and the DDs is a differential value of the output error amount Ds.

$$DFi=Kpp \cdot Ds+Kii \cdot SDs+Kdd \cdot DDs \tag{16}$$

(3) The CPU obtains a new integrated value SDs of the output error amount by adding the "output error amount Ds which is newly obtained" to the "current integrated value SDs of the output error amount."
(4) The CPU obtains a new differential value DDs by subtracting a "previous output error amount Dsold which is the output error amount Ds calculated the predetermined time before" from the "calculated output error amount Ds".
(5) The CPU stores the "calculated output error amount Ds" as the "previous output error amount Dsold."

In this way, the CPU calculate the "main feedback amount DFi" according to a proportional-integral-differential (PID) control to have/make the output value Voxs of the electro-motive-force-type oxygen concentration sensor which is disposed at the position at which the upstream air-fuel ratio sensor 56 is disposed coincide with the target value Vref. This feedback amount DFi is used at step 1140 shown in FIG. 11.

As described above, the first air-fuel ratio correlated parameter obtaining section of the fifth control apparatus is configured so as to obtain, using the first relationship, as the first air-fuel ratio correlated parameter, a value (that is, alcohol-concentration•imbalance-ratio corrected output value VoxsER) into which the actual output value Voxs of the air-fuel ratio sensor is converted based on the actual alcohol concentration and the actual air-fuel ratio imbalance indicating value, so that the actual output value Voxs of the air-fuel ratio sensor changes to the output value when (on the assumption that) the alcohol concentration is equal to the predetermined base alcohol concentration and the actual air-fuel ratio imbalance indicating value is equal to the predetermined base air-fuel ratio imbalance indicating value.

Further, the first air-fuel ratio correlated parameter obtaining section is configured so as to:
store the first relationship as,
a first look-up table (FIG. 22, or the first function expressing the relationship for the conversion using FIG. 22) for converting, based on the alcohol concentration, the output value of the air-fuel ratio sensor into an output value of the air-fuel ratio sensor in a case in which the alcohol concentration is equal to the predetermined base alcohol concentration; and
a second look-up table (FIG. 23, or the second function expressing the relationship for the conversion using FIG. 23) for converting, based on the air-fuel ratio imbalance indicating value, the output value of the air-fuel ratio sensor into an output value of the air-fuel ratio sensor in a case in which the air-fuel ratio imbalance indicating value is equal to the predetermined base air-fuel ratio imbalance indicating value;
obtain, as an alcohol concentration corrected output value VoxsE, an output value of the air-fuel ratio sensor obtained by inputting the actual output value of the air-fuel ratio sensor and the actual alcohol concentration to the first look-up table or the first function; and
obtain, as the first air-fuel ratio correlated parameter, an output value (that is, alcohol-concentration•imbalance-ratio corrected output value VoxsER) of the air-fuel ratio sensor obtained by inputting the obtained alcohol concentration corrected output value VoxsE and the actual air-fuel ratio imbalance indicating value RIMB to the second look-up table or the second function.

Furthermore, the fifth control apparatus carries out the main feedback control in such a manner that the alcohol-concentration imbalance-ratio corrected output value VoxsER coincides with the target value Vref. Accordingly, even when the electro-motive-force-type oxygen concentration sensor is used as the air-fuel ratio sensor, the air-fuel ratio can be controlled so as to be an air-fuel ratio corresponding to the target value Vref, regardless of the alcohol concentration Et and the degree of the non-uniformity among the cylinder-by-cylinder air-fuel ratios.

Moreover, the fifth control apparatus obtains the air-fuel ratio imbalance indicating value RIMB based on the differential value dVoxsE/dt of the alcohol-concentration corrected output value VoxsE. Accordingly, the air-fuel ratio imbalance indicating value RIMB which represents the degree of the non-uniformity among the cylinder-by-cylinder air-fuel ratios with high accuracy can be obtained.

As described above, each of the fuel injection amount control apparatuses according to the embodiments of the present invention can prevent the erroneous lean control caused by the high alcohol concentration and a large degree of the non-uniformity among the cylinder-by-cylinder air-fuel ratios from occurring. Accordingly, the air-fuel ratio of the exhaust gas can be made to come closer to the target air-fuel ratio, and thus, the amount of discharged substances such as NOx can be decreased.

The present invention is not limited to the above-described embodiments, and may be modified in various manners without departing from the scope of the present invention. For example, the air-fuel ratio imbalance indicating value obtaining section of each of the embodiments may obtain the air-fuel ratio imbalance indicating value RIMB as follows.

(A) As described above, the imbalance indicating value obtaining section is configured so as to obtain, as the air-fuel ratio imbalance indicating value RIMB, the value which becomes larger as the variation (amplitude of the fluctuation) of the air-fuel ratio of the exhaust gas passing through the position at which the upstream air-fuel ratio sensor 56 is disposed becomes larger, based on the second air-fuel ratio correlated parameter.

The second air-fuel ratio correlated parameter is the value obtained by eliminating the effect on the output value of the air-fuel ratio sensor which at least the alcohol concentration has, and may include the tentative detected air-fuel ratio abyfsvir, the pressure•alcohol-concentration corrected output value VafsPE, the alcohol-concentration corrected output value VafsE, and the alcohol-concentration corrected output value VoxE. Hereinafter, the second air-fuel ratio correlated parameter is expressed as V2. It should be noted that a value correlated to a value X may mean a value varying depending on the value X, such as an average of absolute values of a plurality of the values X obtained in a predetermined period (e.g., the unit combustion cycle period, or the time period having an integral (natural number) multiple of the unit combustion cycle period), and a difference between a maximum value and a minimum value of the value X in the predetermined period.

The imbalance indicating value obtaining section may be configured so as to obtain a differential value $d(V2)/dt$ of the second air-fuel ratio correlated parameter V2, and obtain, as the air-fuel ratio imbalance indicating value RIMB, a value which is correlated to the obtained differential value $d(V2)/dt$.

The imbalance indicating value obtaining section is configured so as to obtain a second order differential value $d^2(V2)/dt^2$ with respect to time of the second air-fuel ratio correlated parameter V2, and obtain, as the air-fuel ratio imbalance indicating value RIMB, a value correlated to the obtained second order differential value $d^2(V2)/dt^2$. As shown in (D) of FIG. 9 which shows the second order differential value $d^2(abyfsvir)/dt^2$ as an example, the second order differential value $d^2(V2)/dt^2$ becomes a relatively small value when the degree of the non-uniformity among the cylinder-by-cylinder air-fuel ratios is small as shown by the broken line C5 in (D) of FIG. 9, and becomes a relatively large value when the degree of the non-uniformity among the cylinder-by-cylinder air-fuel ratios is large as shown by the solid line C6 in (D) of FIG. 9.

The second order differential value $d^2(V2)/dt^2$ may be obtained by obtaining the differential value $d(V2)/dt$ every elapse of a constant time by subtracting the second air-fuel ratio correlated parameter V2 the constant time before from the current second air-fuel ratio correlated parameter V2, and by subtracting the differential values $d(V2)/dt$ the constant time before from the newly obtained differential values $d(V2)/dt$.

It should be noted that each of the values correlated to "the differential values $d(V2)/dt$, and the second order differential value $d^2(V2)/dt^2$" is affected by the intake air amount Ga, but is unlikely to be affected by the engine rotational speed NE. This is because, as described above, a flow rate of the exhaust gas inside of the protective cover of the air-fuel ratio sensor 56 varies depending on a flow rate of the exhaust gas EX flowing in the vicinity of the through holes of the protective cover (and thus, the intake air amount (flow rate) Ga). Accordingly, those values are preferable parameters for the base indicating value of the air-fuel ratio imbalance indicating value RIMB, since they can indicate/represent the degree of the non-uniformity among the cylinder-by-cylinder air-fuel ratios without being affected by the engine rotational speed NE.

The imbalance indicating value obtaining section may be configured so as to obtain, as the air-fuel ratio imbalance indicating value RIMB, a value correlated to a difference ΔX between a maximum value and a minimum value of the second air-fuel ratio correlated parameter V2 in a predetermined period (e.g., period having a time length of an integral (natural number) multiple of the unit combustion cycle period). As is clear from the solid line C2 and the broken line C1 shown in (B) of FIG. 9, the difference ΔX becomes larger as the degree of the non-uniformity among the cylinder-by-cylinder air-fuel ratios becomes larger.

The imbalance indicating value obtaining section may be configured so as to obtain, as the air-fuel ratio imbalance indicating value RIMB, a value correlated to a trace/trajectory length of the second air-fuel ratio correlated parameter V2 in a predetermined period. As is apparent from (B) of FIG. 9, the trace/trajectory length becomes larger as the difference among the cylinder-by-cylinder air-fuel ratios becomes larger. For example, the value correlated to the trace/trajectory length is an average of absolute values of a plurality of the trace/trajectory lengths obtained in the unit combustion cycle period or a period having a time length of an integral (natural number) multiple of the unit combustion cycle period.

It should be noted that the trace/trajectory length of the second air-fuel ratio correlated parameter V2 may be obtained by obtaining the second air-fuel ratio correlated parameter V2 every elapse of a constant sampling time ts, and accumulating an absolute value of a difference between the second air-fuel ratio correlated parameter V2 and the second air-fuel ratio correlated parameter V2 which was obtained the constant sampling time ts before, for example.

(B) The imbalance indicating value obtaining section may be configured so as to obtain, as the air-fuel ratio imbalance indicating value, a value (rotational speed fluctuation correlated value) which becomes larger as a variation of the rotational speed of the engine 10 becomes larger. The rotational speed fluctuation correlated value may be obtained by obtaining an absolute value of a change amount ΔNE of the engine rotational speed NE every elapse of a constant sampling time, and averaging a plurality of the absolute values of the change amounts ΔNE in the unit combustion cycle period, for example.

Further, each of the fuel injection amount control apparatuses for an internal combustion engine of the embodiments according to the present invention may additionally performs an air-fuel ratio feedback control (sub feedback control) based on the output value Voxs of the downstream air-fuel ratio sensor 57. In this case, the control apparatus may obtain a sub feedback amount KSFB according to a PID control in such a manner that the output value Voxs coincides with a value corresponding to the base air-fuel ratio (e.g., value Vst corresponding to the stoichiometric air-fuel ratio), and correct the target air-fuel ratio abyfr based on the sub feedback amount KSFB.

In this case, the imbalance indicating value obtaining section may obtain, as the air-fuel ratio imbalance indicating value, a value varying based on the sub feedback amount KSFB. That is, as disclosed in the patent literature No. 2 described above, a parameter indicating a state of a difference between the air-fuel ratio detected by the upstream air-fuel ratio sensor (56) and the air-fuel ratio detected by the downstream air-fuel ratio sensor (57) may be adopted as a parameter for obtaining the air-fuel ratio imbalance indicating value RIMB.

Furthermore, each of the control apparatuses described above may be applied to a V-type engine. In such a case, the V-type engine may comprise right bank upstream catalyst disposed at a position downstream of an exhaust gas merging (aggregated) portion of two or more of cylinders belonging to a right bank. In addition, the V-type engine may comprise a left bank upstream catalyst disposed at a position downstream of an exhaust gas merging portion of two or more of cylinders belonging to a left bank.

Further, the V-type engine may comprise an upstream air-fuel ratio sensor for the right bank and a downstream air-fuel ratio sensor for the right bank disposed upstream and downstream of the right bank upstream catalyst, respectively, and may comprise upstream air-fuel ratio sensor for the left bank and a downstream air-fuel ratio sensor for the left bank disposed upstream and downstream of the left bank upstream catalyst, respectively.

Each of the upstream air-fuel ratio sensors, similarly to the air-fuel ratio sensor 56, is disposed between the exhaust gas merging portion of each of the banks and the upstream catalyst of each of the banks. In this case, a main feedback control for the right bank and a sub feedback for the right bank are performed. A main feedback control for the left bank and a sub feedback for the left bank are independently performed.

In this case, the control apparatus may obtain a tentative detected air-fuel ratio abyfsvir for the right bank based on the output value of the upstream air-fuel ratio sensor of the right bank, obtain an air-fuel ratio imbalance indicating value RIMB based on the tentative detected air-fuel ratio abyfsvir, and obtain an actual detected air-fuel ratio abyfsact for the right bank using the air-fuel ratio imbalance indicating value RIMB. Similarly, the control apparatus may obtain a tentative detected air-fuel ratio abyfsvir for the left bank based on the output value of the upstream air-fuel ratio sensor of the left bank, obtain an air-fuel ratio imbalance indicating value RIMB based on the tentative detected air-fuel ratio abyfsvir, and obtain an actual detected air-fuel ratio abyfsact for the left bank air-fuel ratio imbalance indicating value RIMB.

In addition, the control apparatus according to each of the embodiments described above obtains the actual detected air-fuel ratio abyfsact, without discriminating between a case in which the air-fuel ratio of the imbalanced cylinder deviates toward the rich side with respect to the stoichiometric air-fuel ratio stoich and a case in which the air-fuel ratio of the imbalanced cylinder deviates toward the lean side with respect to the stoichiometric air-fuel ratio stoich. This is because, the degrees of the excessive lean correction due to the erroneous lean control in those cases are the same as each other, if the absolute values of the imbalance ratios are the same as each other in those cases (i.e., the air-fuel ratio imbalance indicating value RIMB are the same as each other in those cases).

In contrast, even when the air-fuel ratio imbalance indicating value RIMB is a "certain same value", the first control apparatus may be configured so as to select a different "look-up table shown in FIG. 1 or FIG. 3" between when the air-fuel ratio of the imbalanced cylinder deviates toward the rich side with respect to the stoichiometric air-fuel ratio stoich and when the air-fuel ratio of the imbalanced cylinder deviates toward the lean side with respect to the stoichiometric air-fuel ratio stoich, and may obtain the actual detected air-fuel ratio abyfsact based on the selected air-fuel ratio conversion table.

It should be noted that it can be determined whether the air-fuel ratio of the imbalanced cylinder deviates toward the rich side or the lean side with respect to the stoichiometric air-fuel ratio stoich, based on the fluctuation of the engine rotational speed (the fluctuation becomes larger when the air-fuel ratio of the imbalanced cylinder deviates toward the lean side with respect to the stoichiometric air-fuel ratio stoich than when air-fuel ratio of the imbalanced cylinder deviates toward the rich side with respect to the stoichiometric air-fuel ratio stoich), or based on the following method.

The CPU obtains an average PAF of the "differential values d(abyfsvir)/dt, each of which is positive" among the differential values d(abyfsvir)/dt in the unit combustion cycle.

The CPU obtains an average NAF of absolute values of the "differential values d(abyfsvir)/dt, each of which is negative" among the differential values d(abyfsvir)/dt in the unit combustion cycle.

The CPU determines that the air-fuel ratio of the imbalanced cylinder deviates toward the rich side with respect to the stoichiometric air-fuel ratio stoich when the average NAF is larger than the average PAF.

The CPU determines that the air-fuel ratio of the imbalanced cylinder deviates toward the lean side with respect to the stoichiometric air-fuel ratio stoich when the average NAF is smaller than the average PAF.

Further, in the embodiments, the base alcohol concentration is "0", however, the base alcohol concentration may be a value other than "0." Similarly, the air-fuel ratio imbalance indicating value is "0", however, the air-fuel ratio imbalance indicating value may be a value other than "0."

The invention claimed is:

1. A fuel injection amount control apparatus comprising:
    a three way catalyst which is disposed in an exhaust passage of a multi cylinder internal combustion engine and at a position downstream of an exhaust gas aggregated portion into which exhaust gases discharged from a plurality of cylinders of said engine merge;
    an air-fuel ratio sensor, which is disposed at a position between said exhaust gas aggregated portion and said three way catalyst, which includes an air-fuel ratio detection element, an exhaust-gas-side electrode layer and a reference-gas-side electrode layer that are formed so as to face to each other across said air-fuel ratio detection element, and a porous layer which covers said exhaust-gas-side electrode layer, and which outputs an output value corresponding to an amount of oxygen and an amount of unburnt substances that are contained in an exhaust gas that has reached said exhaust-gas-side electrode layer via said porous layer, said exhaust gas being included in an exhaust gas passing through said position at which said air-fuel ratio sensor is disposed;
    a plurality of fuel injection valves, each of which is configured so as to inject a fuel to be contained in a mixture supplied to each of combustion chambers of a plurality of said cylinders;
    an alcohol concentration obtaining section configured so as to obtain an alcohol concentration of said fuel;
    an air-fuel ratio imbalance indicating value obtaining section configured so as to obtain, based on a specific parameter, an air-fuel ratio imbalance indicating value which becomes larger as a degree of a non-uniformity among a plurality of said cylinders of cylinder-by-cylinder air-fuel ratios, each of which is an air-fuel ratio of said mixture supplied to each of said combustion chambers of a plurality of said cylinders;
    a first air-fuel ratio correlated parameter obtaining section configured so as to convert an actual output value of said air-fuel ratio sensor into an actual first air-fuel ratio correlated parameter based on said obtained actual alcohol concentration and said obtained actual air-fuel ratio imbalance indicating value, using a predetermined first relationship among an output value of said air-fuel ratio sensor, an alcohol concentration, an air-fuel ratio imbalance indicating value, and a first air-fuel ratio correlated parameter correlated to a true air-fuel ratio of an exhaust gas;
    an instructed fuel injection amount determining section configured so as to determine an instructed fuel injection amount which is an instruction value of an amount of said fuel to be injected from each of a plurality of said fuel injection valves, by performing a feedback correction on said amount of said fuel to be injected from each of said fuel injection valves in such a manner that said obtained actual first air-fuel ratio correlated parameter coincides with a predetermined target value; and
    an injection instruction signal supplying section configured so as to send an injection instruction signal to a plurality of said fuel injection valves in such a manner that each of a plurality of said fuel injection valves injects said fuel in an amount corresponding to said instructed fuel injection amount.

2. The fuel injection amount control apparatus according to claim 1, wherein,
    said air-fuel ratio imbalance indicating value obtaining section is configured so as to:
    convert said actual output value of said air-fuel ratio sensor into an actual second air-fuel ratio correlated parameter based on said obtained actual alcohol concentration, using a predetermined second relationship among an output value of said air-fuel ratio sensor, an alcohol concentration, and a second air-fuel ratio correlated parameter correlated to said true air-fuel ratio of said exhaust gas in a case in which said non-uniformity of said cylinder-by-cylinder air-fuel ratios among a plurality of said cylinders is not occurring;
    adopt, as said specific parameter, said actual second air-fuel ratio correlated parameter; and
    obtain, as said air-fuel ratio imbalance indicating value, a value which becomes larger as a variation of said second air-fuel ratio correlated parameter becomes larger.

3. The fuel injection amount control apparatus according to claim 2, further comprising:
    an exhaust gas pressure obtaining section configured so as to obtain an actual pressure of said exhaust gas reaching said air-fuel ratio sensor,
    and wherein,
    said first relationship is a relationship among said output value of said air-fuel ratio sensor, said alcohol concentration, said air-fuel ratio imbalance indicating value, said pressure of said exhaust gas reaching said air-fuel ratio sensor, and said first air-fuel ratio correlated parameter; and
    said first air-fuel ratio correlated parameter obtaining section is configured so as to convert said actual output value of said air-fuel ratio sensor into said actual first air-fuel ratio correlated parameter based on not only said obtained actual alcohol concentration and said obtained actual air-fuel ratio imbalance indicating value but also said obtained actual pressure.

4. The fuel injection amount control apparatus according to claim 3, wherein,
    said second relationship is a relationship among said output value of said air-fuel ratio sensor, said alcohol concentration, said pressure of said exhaust gas reaching said air-fuel ratio sensor, and said second air-fuel ratio correlated parameter, and said air-fuel ratio imbalance indicating value obtaining section is configured so as to convert said actual output value of said air-fuel ratio sensor into said actual second air-fuel ratio correlated parameter based on not only said obtained actual alcohol concentration but also said obtained actual pressure.

5. The fuel injection amount control apparatus according to claim 1, wherein,
said first air-fuel ratio correlated parameter obtaining section is configured so as to obtain, as said first air-fuel ratio correlated parameter, a value which is an air-fuel ratio into which said actual output value of said air-fuel ratio sensor is converted using said first relationship, said converted air-fuel ratio being an air-fuel ratio which becomes larger as said actual alcohol concentration becomes higher and as said actual air-fuel ratio imbalance indicating value becomes larger; and
said instructed fuel injection amount determining section is configured so as to use, as said target value, a target air-fuel ratio which is set at a predetermined air-fuel ratio which is within a window of said three way catalyst.

6. The fuel injection amount control apparatus according to claim 5, wherein,
said first air-fuel ratio correlated parameter obtaining section is configured so as to:
store said first relationship in a form of a look-up table or a function, which inputs said output value of said air-fuel ratio sensor, said alcohol concentration, and said air-fuel ratio imbalance indicating value, and which outputs said first air-fuel ratio correlated parameter; and
obtain said actual first air-fuel ratio correlated parameter by inputting said actual output value of said air-fuel ratio sensor, said actual alcohol concentration, and said actual air-fuel ratio imbalance indicating value to said look-up table or said function.

7. The fuel injection amount control apparatus according to claim 5, wherein,
said first air-fuel ratio correlated parameter obtaining section is configured so as to store said first relationship as,
a first look-up table or a first function for converting, based on said alcohol concentration, said output value of said air-fuel ratio sensor into an output value of said air-fuel ratio sensor in a case in which said alcohol concentration is equal to a predetermined base alcohol concentration;
a second look-up table or a second function for converting, based on said air-fuel ratio imbalance indicating value, said output value of said air-fuel ratio sensor into an output value of said air-fuel ratio sensor in a case in which said air-fuel ratio imbalance indicating value is equal to a predetermined base air-fuel ratio imbalance indicating value; and
a third look-up table or a third function for converting into an air-fuel ratio, said output value of said air-fuel ratio sensor when said alcohol concentration is equal to said base alcohol concentration and said air-fuel ratio imbalance indicating value is equal to said base air-fuel ratio imbalance indicating value;
so as to obtain, as an alcohol concentration corrected output value, an output value of said air-fuel ratio sensor which is obtained by inputting said actual output value of said air-fuel ratio sensor and said actual alcohol concentration to said first look-up table or said first function;
so as to obtain, as an alcohol concentration•air-fuel ratio imbalance indicating value corrected output value, an output value of said air-fuel ratio sensor which is obtained by inputting said alcohol concentration corrected output value and said actual air-fuel ratio imbalance indicating value to said second look-up table or said second function; and
so as to obtain, as said actual first air-fuel ratio correlated parameter, an air-fuel ratio which is obtained by inputting said alcohol concentration•air-fuel ratio imbalance indicating value corrected output value to said third look-up table or said third function.

8. The fuel injection amount control apparatus according to claim 1, wherein,
said first air-fuel ratio correlated parameter obtaining section is configured so as to obtain, as said first air-fuel ratio correlated parameter, a value into which said actual output value of said air-fuel ratio sensor is converted based on said actual alcohol concentration and said actual air-fuel ratio imbalance indicating value using said first relationship, so that said actual output value of said air-fuel ratio sensor becomes equal to an output value when said alcohol concentration is equal to said predetermined base alcohol concentration and said actual air-fuel ratio imbalance indicating value is equal to said predetermined base air-fuel ratio imbalance indicating value; and
said instructed fuel injection amount determining section is configured so as to use, as said target value, a value which is equal to said output value of said air-fuel ratio sensor for a predetermined air-fuel ratio which is within said window of said three way catalyst when said alcohol concentration is equal to said predetermined base alcohol concentration and said actual air-fuel ratio imbalance indicating value is equal to said predetermined base air-fuel ratio imbalance indicating value.

9. The fuel injection amount control apparatus according to claim 8, wherein,
said first air-fuel ratio correlated parameter obtaining section is configured so as to:
store said first relationship as,
a first look-up table or a first function for converting, based on said alcohol concentration, said output value of said air-fuel ratio sensor into an output value of said air-fuel ratio sensor in a case in which said alcohol concentration is equal to said predetermined base alcohol concentration; and
a second look-up table or a second function for converting, based on said air-fuel ratio imbalance indicating value, said output value of said air-fuel ratio sensor into an output value of said air-fuel ratio sensor in a case in which said air-fuel ratio imbalance indicating value is equal to said predetermined base air-fuel ratio imbalance indicating value;
obtain, as an alcohol concentration corrected output value, an output value of said air-fuel ratio sensor obtained by inputting said actual output value of said air-fuel ratio sensor and said actual alcohol concentration to said first look-up table or said first function; and
obtain, as said first air-fuel ratio correlated parameter, an output value of said air-fuel ratio sensor obtained by inputting said obtained alcohol concentration corrected output value and said actual air-fuel ratio imbalance indicating value to said second look-up table or said second function.

10. The fuel injection amount control apparatus according to claim 2, wherein,
said air-fuel ratio imbalance indicating value obtaining section is configured so as to:
store said second relationship in a form of a look-up table or a function, which inputs said output value of said air-fuel ratio sensor and said alcohol concentration and outputs said second air-fuel ratio correlated parameter; and obtain said actual second air-fuel ratio correlated parameter by inputting said actual output value of said air-fuel ratio sensor and said actual alcohol concentration to said look-up table or said function.

11. The fuel injection amount control apparatus according to claim 4, wherein,
said air-fuel ratio imbalance indicating value obtaining section is configured so as to:
store said second relationship in a form of a look-up table or a function, which inputs said output value of said air-fuel ratio sensor, said alcohol concentration, and said pressure of said exhaust gas reaching said air-fuel ratio sensor, and outputs said second air-fuel ratio correlated parameter; and
obtain said actual second air-fuel ratio correlated parameter by inputting said actual output value of said air-fuel ratio sensor, said actual alcohol concentration, and said obtained actual pressure to said look-up table or said function.

12. The fuel injection amount control apparatus according to claim 2, wherein,
said air-fuel ratio imbalance indicating value obtaining section is configured so as to obtain said air-fuel ratio imbalance indicating value based on one of:
a differential value of said second air-fuel ratio correlated parameter with respect to time;
a second order differential value of said second air-fuel ratio correlated parameter with respect to time; and
a trace length of said second air-fuel ratio correlated parameter in a predetermined period.

13. The fuel injection amount control apparatus according to claim 1, wherein,
said instructed fuel injection amount determining section is configured so as to:
calculate a main feedback correction amount by multiplying a value correlated to a difference between said obtained actual first air-fuel ratio correlated parameter and said target value by a predetermined gain, and carry out said feedback correction using said main feedback correction amount; and
set said gain to a value in a period after rich-lean inversion time point larger than a value in a period after lean-rich inversion time point, said period after rich-lean inversion time point being a time period until a predetermined time elapses from a rich-lean inversion time point at which said actual output value of said air-fuel ratio sensor has changed from a value indicating an air-fuel ratio smaller than said stoichiometric air-fuel ratio to a value indicating an air-fuel ratio larger than said stoichiometric air-fuel ratio, and said period after lean-rich inversion time point being a time period until a predetermined time elapses from a lean-rich inversion time point at which said actual output value of said air-fuel ratio sensor has changed from a value indicating an air-fuel ratio larger than said stoichiometric air-fuel ratio to a value indicating an air-fuel ratio smaller than said stoichiometric air-fuel ratio.

14. The fuel injection amount control apparatus according to claim 13, wherein,
said instructed fuel injection amount determining section is configured so as to set said gain in such a manner that a difference between said gain which is set in said period after rich-lean inversion time point and said gain which is set in said period after lean-rich inversion time point becomes larger as said obtained actual alcohol concentration becomes higher.

15. The fuel injection amount control apparatus according to claim 13, wherein,
said instructed fuel injection amount determining section is configured so as to set said gain in such a manner that a difference between said gain which is set in said period after rich-lean inversion time point and said gain which is set in said period after lean-rich inversion time point becomes larger as said obtained actual air-fuel ratio imbalance indicating value becomes larger.

* * * * *